United States Patent
Yong et al.

(10) Patent No.: US 12,134,626 B2
(45) Date of Patent: Nov. 5, 2024

(54) FERROCENE DERIVATIVE, PREPARATION METHOD THEREFOR AND USE THEREOF

(71) Applicant: XIAMEN INSTITUTE OF RARE-EARTH MATERIALS, Fujian (CN)

(72) Inventors: Jianping Yong, Fujian (CN); Canzhong Lu, Fujian (CN)

(73) Assignee: XIAMEN INSTITUTE OF RARE EARTH MATERIALS, Xiamen (CN)

( * ) Notice: Subject to any disclaimer, the term of this patent is extended or adjusted under 35 U.S.C. 154(b) by 801 days.

(21) Appl. No.: 17/289,714

(22) PCT Filed: Feb. 24, 2021

(86) PCT No.: PCT/CN2021/077608
§ 371 (c)(1),
(2) Date: Apr. 28, 2021

(87) PCT Pub. No.: WO2022/178701
PCT Pub. Date: Sep. 1, 2022

(65) Prior Publication Data
US 2022/0356199 A1 Nov. 10, 2022

(51) Int. Cl.
C07F 17/02 (2006.01)
A61P 35/00 (2006.01)

(52) U.S. Cl.
CPC ............. *C07F 17/02* (2013.01); *A61P 35/00* (2018.01)

(58) Field of Classification Search
CPC ......... C07F 17/02; C07B 41/08; C07B 43/00; A61P 35/00
See application file for complete search history.

(56) References Cited

U.S. PATENT DOCUMENTS 8,426,462 B2  4/2013  Jaouen et al.
9,738,673 B1 *  8/2017  Yong ................ C07F 17/02

FOREIGN PATENT DOCUMENTS

| CN | 103319543 A | 9/2013 |
| CN | 103360382 A | 10/2013 |
| CN | 103601762 A | 2/2014 |
| CN | 104230912 A | 12/2014 |
| CN | 106518933 A | 3/2017 |
| CN | 106905379 A | 6/2017 |

OTHER PUBLICATIONS

Chong et al. Nature Medicine, vol. 19. No. 11: 1389-1400, Nov. 2013 (Year: 2013).*
Smith (March's Advanced Organic Chemistry—Part 1, 2013 John Wiley & Sons, Inc., p. 1-30 (Year: 2013).*
Mikhaylov, Alexander et al.; "Spontaneous Symmetry Breaking Facilitates Metal-to-Ligand Charge Transfer: A Quantitative Two-Photon Absorption Study of Ferrocene-Phenyleneethynylene Oligomers", The Journal of Physical Chemistry Letters; vol. 9, Mar. 27, 2018; pp. 1893-1899.
Bobula, Tomas et al.; "Sonogashira reactions of a- and b-1-ethynyl-2-deoxyribosides: synthesis of acetylene-extended C-nucleosides", Tetrahedron, vol. 66, Oct. 10, 2009, pp. 530-536.
Rosenfeld, Ayelet et al.; "Preparation, characterization and antileukemic properties of diaminemalonatoplatinum (II) complexes tethered to ferrocene"; Inorganica Chimica Acat; vol. 201; 1992; 219-221.
Neuse, Eberhard W.; "Macromolecular Ferrocene Compounds as Cancer Drug Models"; Journal of Inorganic and Organometallic Polymers and Materials; vol. 15, No. 1; Mar. 2005; pp. 3-32.
Huang, Xian-Feng et al.; "Synthesis, characterization and antitumor activity of novel amide derivatives containing ferrocenyl pyrazol-moiety"; Journal of Organometallic Chemistry; vol. 706-707; 2012; pp. 113-123.
Liu, Wei et al.; "Synthesis, characterization and bioactivity determination of ferrocenyl urea derivatives"; Applied Organometallic Chemistry; vol. 26; 2012; pp. 189-193.
Braga, Susana S. et al.; "A New Age for Iron: Antitumoral Ferrocenes"; Organometallics; vol. 32; Jul. 24, 2013; pp. 5626-5639.
Harry, Andy G. et al.; "The synthesis, structural characterization and biological evaluation of novel N-{para-(ferrocenyl) ethynyl benzoyl} amino acid and dipeptide methyl and ethyl esters as anticancer agents"; Journal of Organometallic Chemistry; vol. 846; Oct. 1, 2017; pp. 379-388.

* cited by examiner

Primary Examiner — Kortney L. Klinkel
Assistant Examiner — Richard Grant Peckham
(74) Attorney, Agent, or Firm — NKL Law; Allen Xue

(57) ABSTRACT

A ferrocene derivative of formula (I). In formula (I), Z is selected from O, NH and S; $R_1$ is selected from hydrogen, methyl and halogen; each $R_2$ is independently selected from hydrogen, halogen, $C_1$-$C_6$ alkyl, $C_1$-$C_6$ alkoxy, $C_1$-$C_6$ haloalkyl, $C_1$-$C_6$ haloalkoxy and nitro; and n is an integer from 0 to 5. The ferrocene derivative, a salt thereof, as well as a solvate thereof have anti-tumor activity, and can be used as candidate drugs or lead compounds for treating diseases such as tumors and cancer.

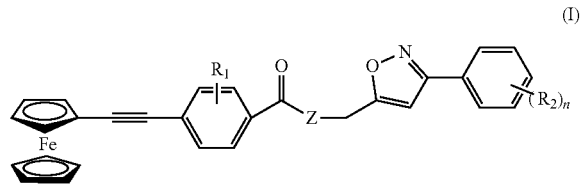

(I)

18 Claims, No Drawings

FERROCENE DERIVATIVE, PREPARATION METHOD THEREFOR AND USE THEREOF

TECHNICAL FIELD

The present invention belongs to the field of compounds, and in particular relates to a ferrocene derivative, a preparation method therefor and use thereof.

BACKGROUND

Cancer has become the leading lethal disease worldwide. Cancer may occur in various organs and tissues at any age. The main types of cancer that lead to death include lung cancer, stomach cancer, liver cancer, colon cancer, breast cancer and the like. Some small-molecule anti-cancer drugs have been used clinically, and some compounds are under pre-clinical trials. However, most cancer patients are not aware of this disease until the cancer has been in the middle or the late stage, and the overall effect of clinical treatment is poor. In particular, it so difficult to cure the cancer patients for the continuous emergence of multidrug resistance. Therefore, it is extremely urgent to develop novel anti-cancer drugs with high activity and low side effects to meet clinical needs.

Ferrocene is a potential pharmacophore for drug design and drug discovery, for it is a neutral, chemically stable and nontoxic molecule. Ferrocene and its derivatives have some special properties including: (1) aromaticity, which makes the core of ferrocene easily to be modified with different functional groups; (2) lipophicity, which enables the core of ferrocene to penetrate the cell membrane and react with various enzymes in the cell; (3) low toxicity with the ability to be easily metabolized in vivo. Ferrocene derivatives show a wide spectrum of pharmacological activities in the field of medicine, especially in the field of development of anti-tumor drugs. A study by A. Rosenefeld et al. showed that ferrocene-modified cis-platin derivatives exhibited a considerably stronger activity in inhibiting leukemia and were much less nephrotoxic than cis-DDP (A. Rosenefeld, et al. *Inorg. Chim. Acat.* 1992, 201:219); another study by E. W. Neuse et al. showed that ferrocene derivatives exhibited unique anti-tumor and anti-cancer activities (E. W. Neuse. *J. Inorga. Organoment.* Polymers and Materials. 2005, 15(1): 3-32); a series of ferrocene derivatives containing pyrazole rings were synthesized by X. F. Huang et al., and the biological evaluation showed that part of ferrocene derivatives exhibited stronger anti-cancer activity than 5-fluorouracil (X. F. Huang, et al. *J. Organomet. Chem.* 2012, 706-707: 113-123); a series of ferrocenylurea derivatives were synthesized by W. Liu et al., and their biological evaluation showed that part of ferrocenylureas possessed stronger inhibition against HIV-1 protease (W. Liu, et al. *Appl. Organomet. Chem.* 2012, 26:189-193); U.S. Pat. No. 8,426,462B2 disclosed that aromatic ring-containing ferrocene derivatives possessed strong inhibitory activity against human breast cancer cell line MDA-MB-231 and prostate cancer cell line PC-3.

Ferrocene is used as a lead compound for designing and synthesizing of anti-tumor drugs (E. W. Neuse. *J. Inorg. Organoment. P.,* 2005, 15(1):3-32; S. S. Braga, et al. *Organometallics,* 2013, 32:5626-5639). Isoxazole heterocycle is a potentially biologically active pharmacophore that is often introduced into drug molecules to enhance their activities. In the previous study of the applicant, a series of novel isoxazole heterocycle-contained ferrocene derivatives were synthesized and their preliminary in vitro inhibitory activities against lung adenocarcinoma cell line A549, colorectal cancer cell line HCT-116 and breast cancer cell MCF-7 were investigated. The results showed that most of the synthesized compounds had stronger inhibitory activity against A549, HCT-116 and MCF-7 cell lines (Yong Jianping, et al. China Patent No. CN103601762A). In order to enrich the library of such compounds, the applicant continues to design and synthesize such isoxazole heterocycle-containing ferrocene derivatives based on the previous good research foundation, to find new anti-cancer lead compounds or candidates.

SUMMARY

The present invention provides a ferrocene derivative of formula (I), a pharmaceutically acceptable salt thereof or a solvate thereof:

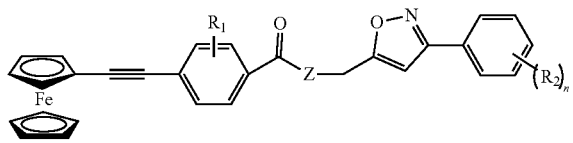

(I)

wherein Z is selected from NH, O and S;
$R_1$ is selected from hydrogen, $C_1$-$C_6$ alkyl and halogen;
$R_2$ is independently selected from hydrogen, halogen, $C_1$-$C_6$ alkyl, $C_1$-$C_6$ alkoxy, $C_1$-$C_6$ haloalkoxy, $C_1$-$C_6$ haloalkyl and nitro; and
n is an integer from 0 to 5, and when n is greater than 1, $R_2$ may be selected from the same or different groups.

According to an embodiment of the present invention, $R_1$ is selected from hydrogen, methyl, chloro and fluoro.

According to an embodiment of the present invention, $R_2$ is independently selected from at least one of the following groups: hydrogen, fluoro, chloro, bromo, methyl, ethyl, methoxy, trifluoromethyl, tert-butyl, cyano and nitro.

According to an embodiment of the present invention, n is 1, 2 or 3.

According to an embodiment of the present invention, "$C_1$-$C_6$ alkyl" may be selected from alkyl having 1, 2, 3, 4, 5 and 6 carbon atoms, and the $C_1$-$C_6$ alkyl moieties in other terms (e.g., $C_1$-$C_6$ alkoxy) are defined as herein.

According to an embodiment of the present invention, the ferrocene derivative of formula (I) is any one of the following compounds:

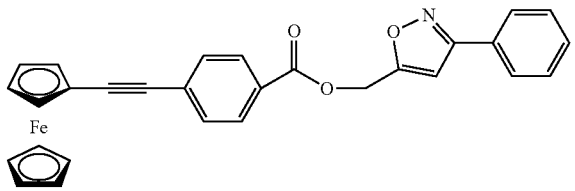

YJP-1

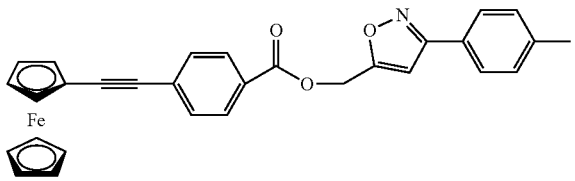

YJP-2

YJP-3
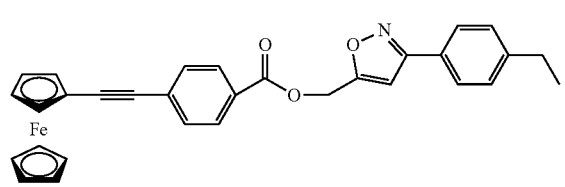
YJP-10
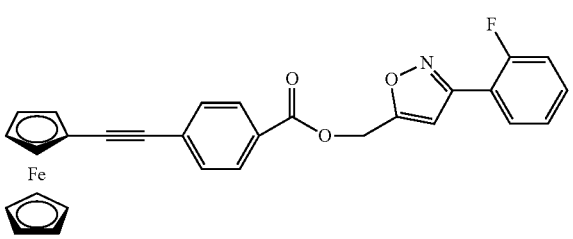
YJP-4
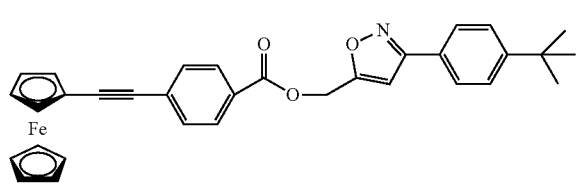
YJP-11
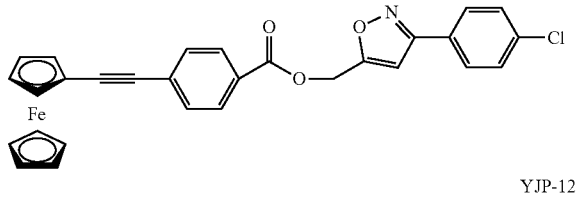
YJP-5
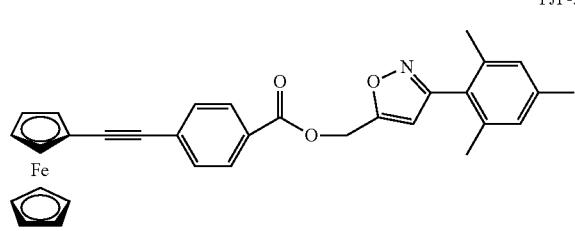
YJP-12
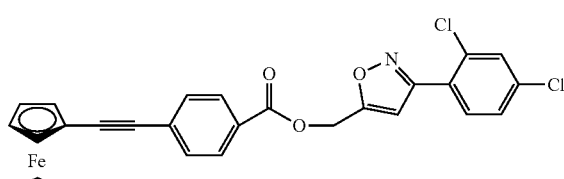
YJP-6
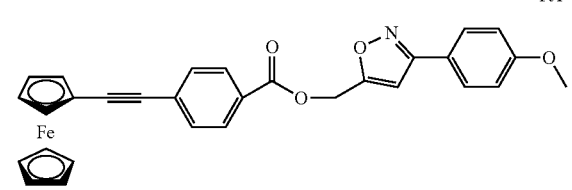
YJP-13
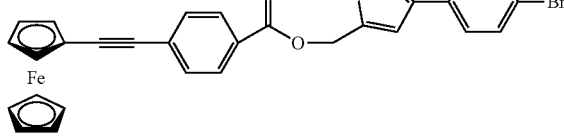
YJP-7
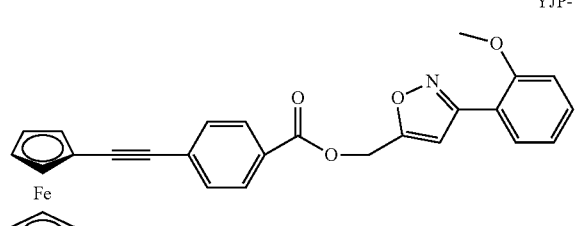
YJP-14
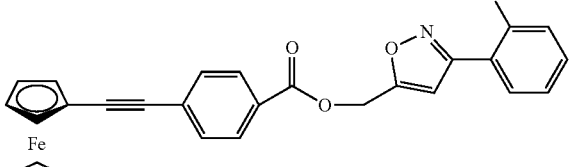
YJP-8
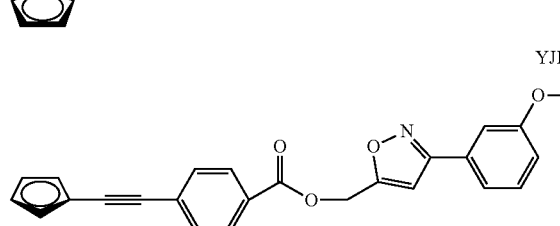
YJP-15
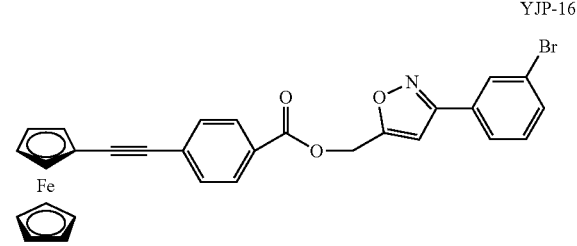
YJP-9
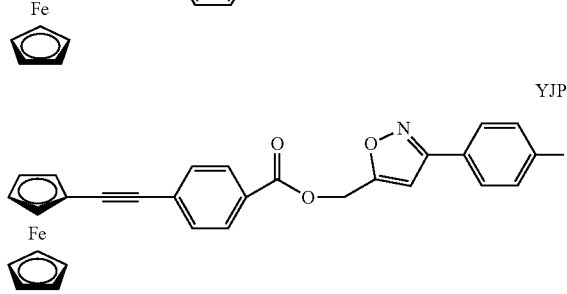
YJP-16

YJP-17
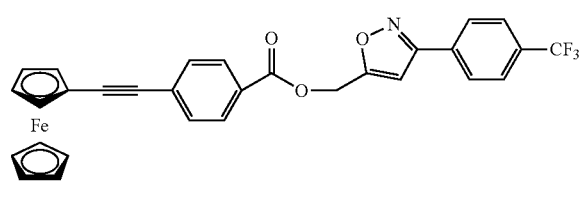
YJP-18
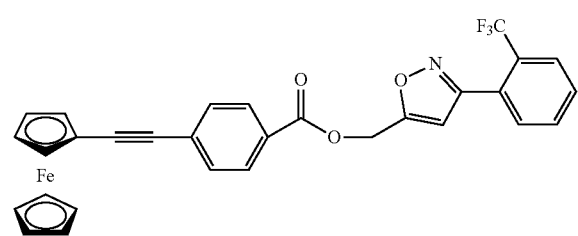
YJP-19
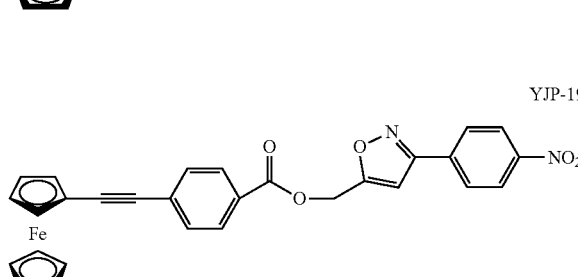
YJP-20
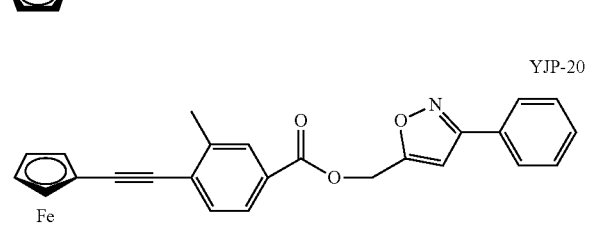
YJP-21
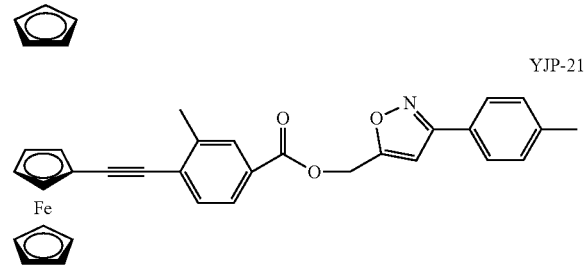
YJP-22
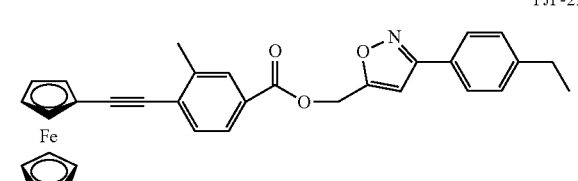
YJP-23
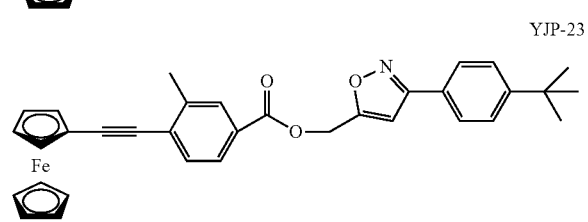
YJP-24
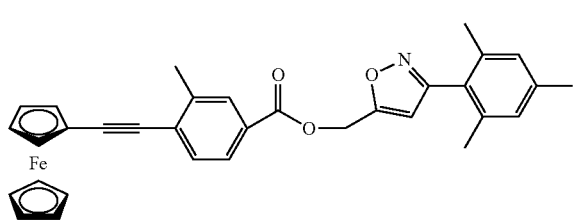
YJP-25
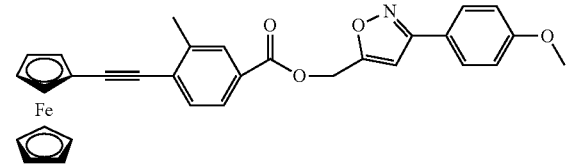
YJP-26
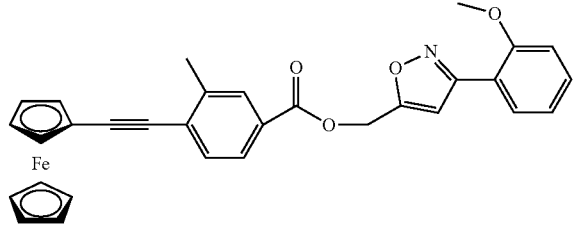
YJP-27
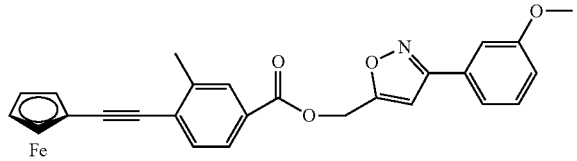
YJP-28
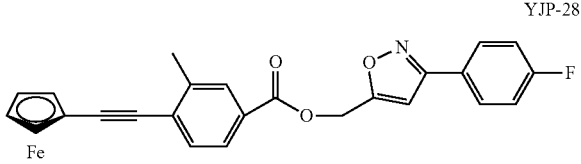
YJP-29
YJP-30
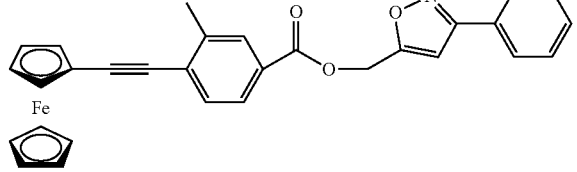

-continued
YJP-31
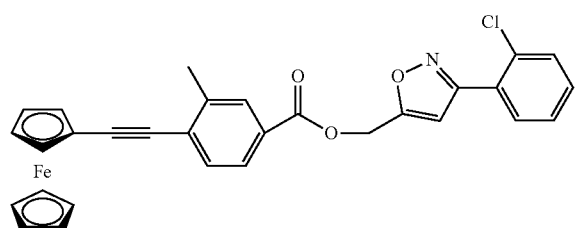
YJP-32
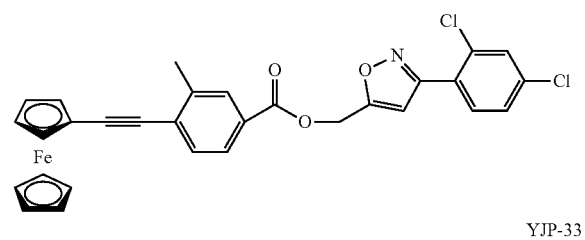
YJP-33
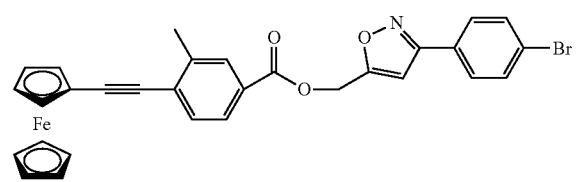
YJP-34
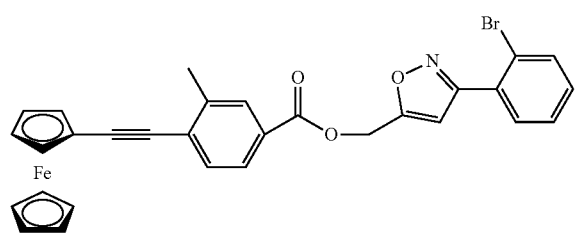
YJP-35
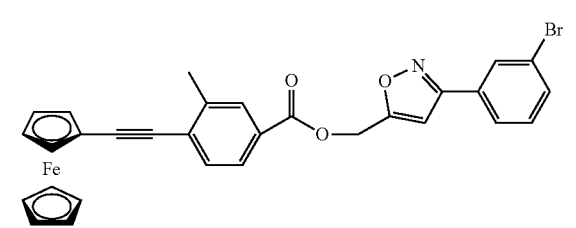
YJP-36
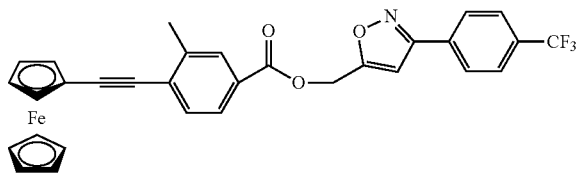
YJP-37
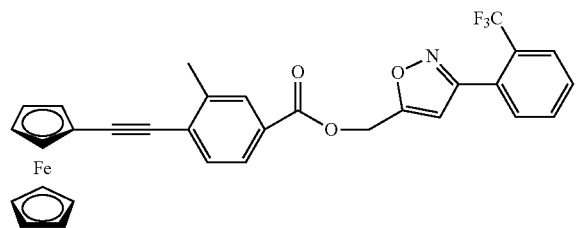
-continued
YJP-38
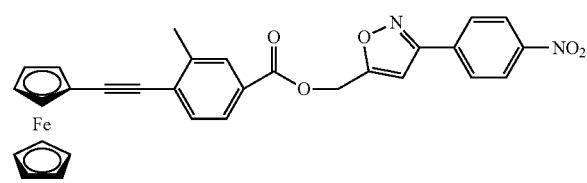
YJP-39
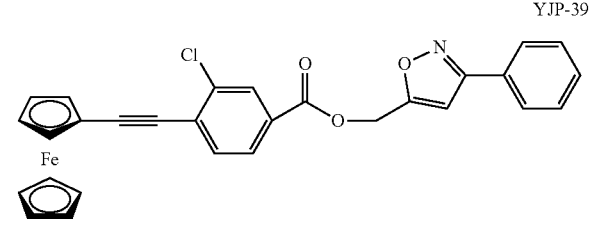
YJP-40
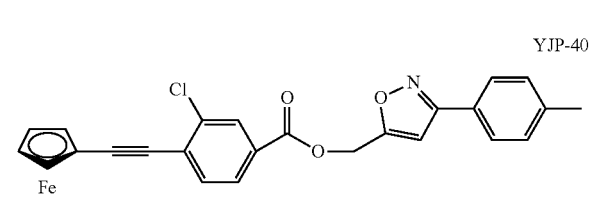
YJP-41
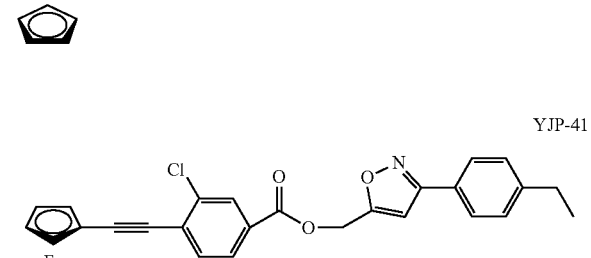
YJP-42
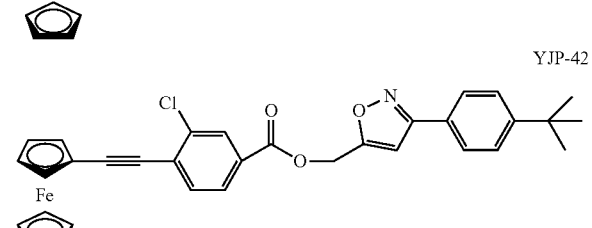
YJP-43
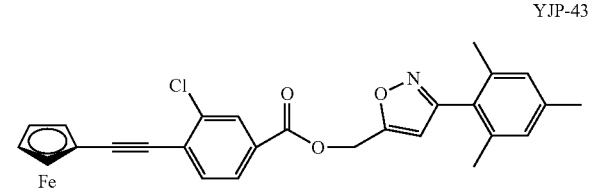
YJP-44
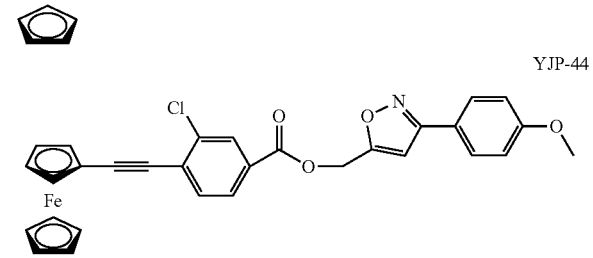

YJP-45
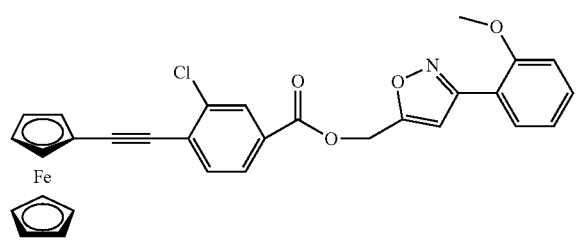
YJP-52
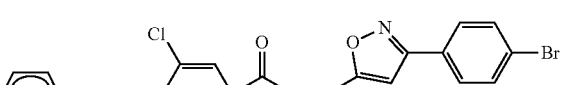
YJP-46
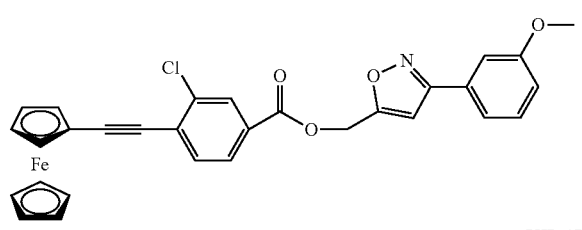
YJP-53
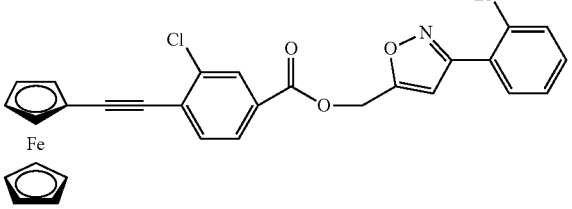
YJP-47
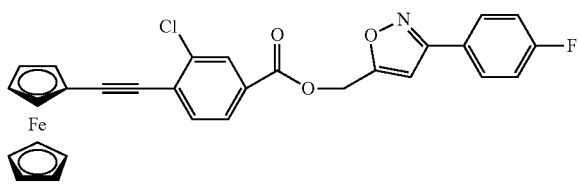
YJP-54
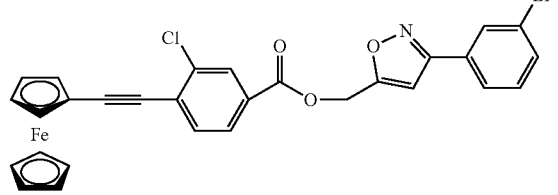
YJP-48
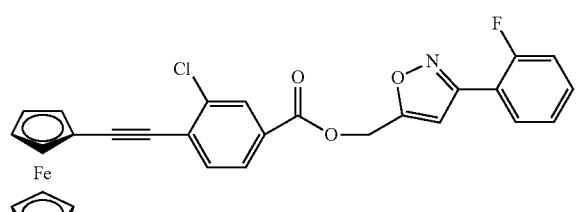
YJP-55
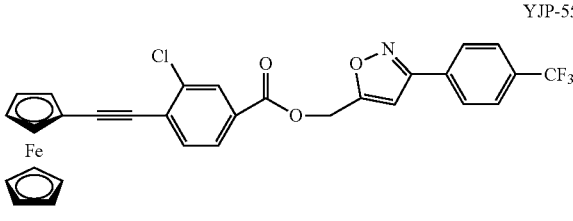
YJP-49
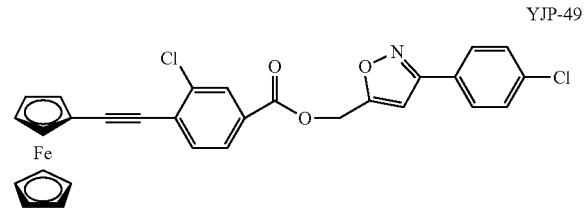
YJP-56
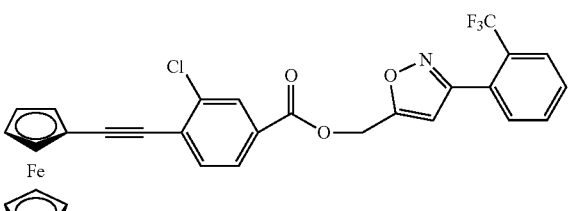
YJP-50
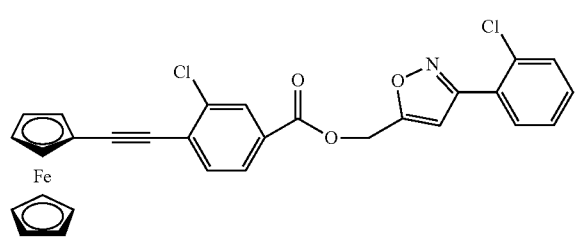
YJP-57
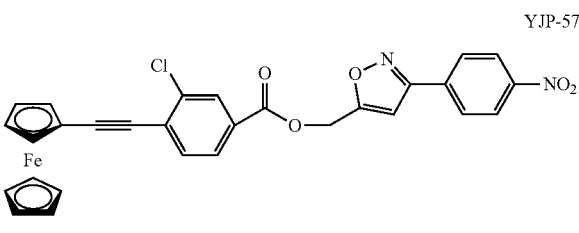
YJP-51
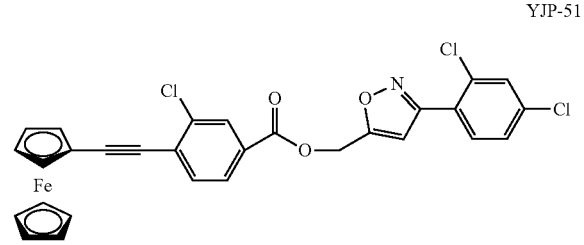
YJP-58
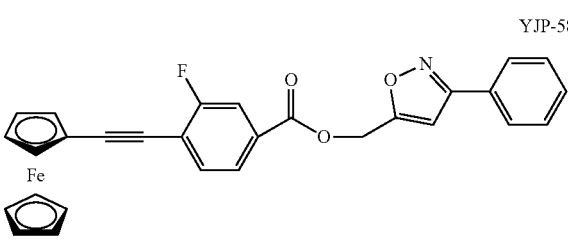

11
-continued
YJP-59
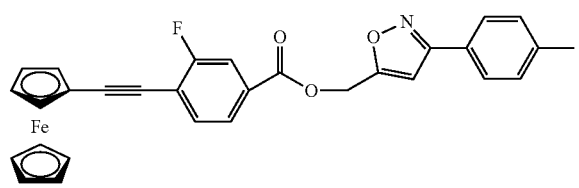
YJP-60
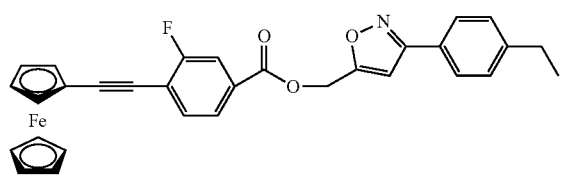
YJP-61
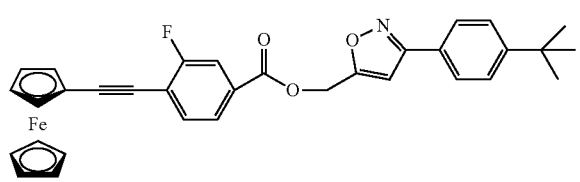
YJP-62
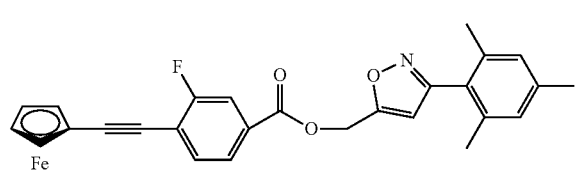
YJP-63
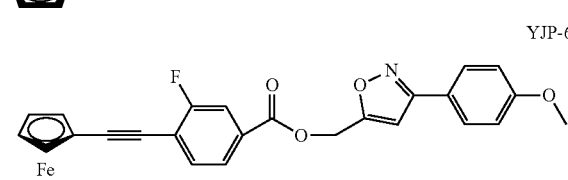
YJP-64
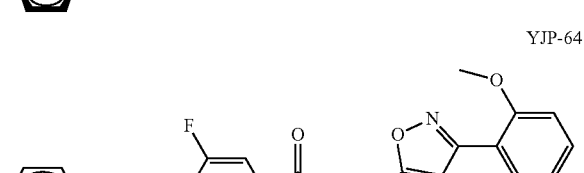
YJP-65
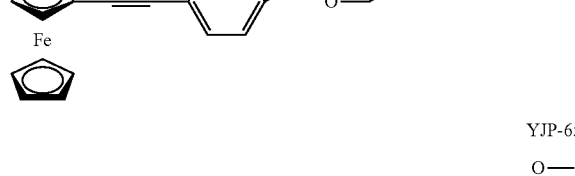
12
-continued
YJP-66
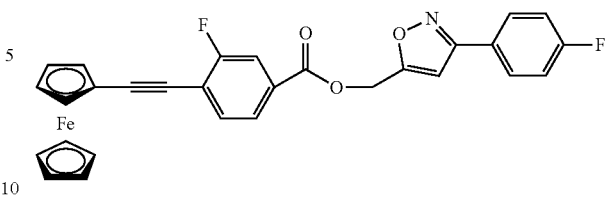
YJP-67
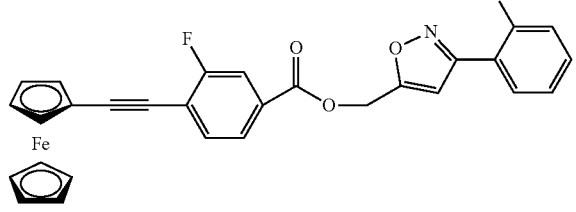
YJP-68
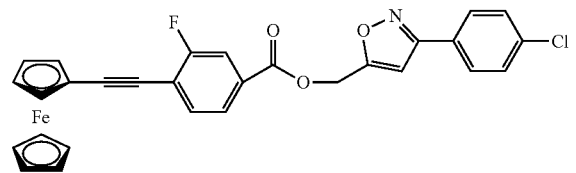
YJP-69
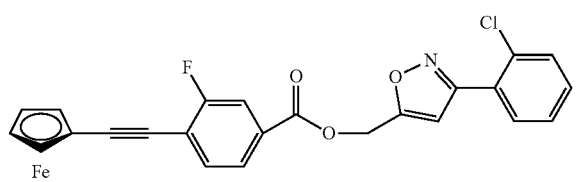
YJP-70
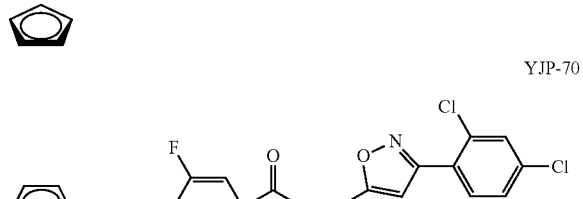
YJP-71
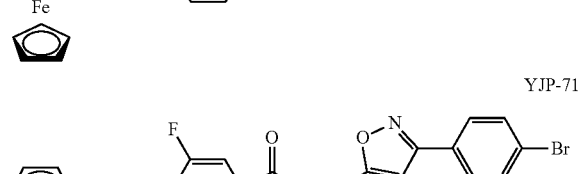
YJP-72
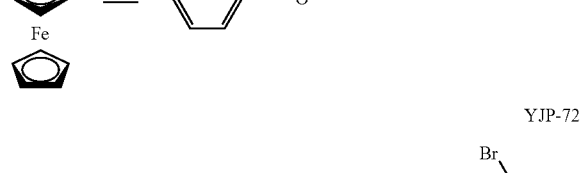

-continued
YJP-73
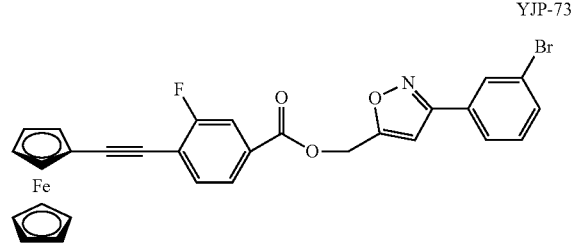
YJP-74
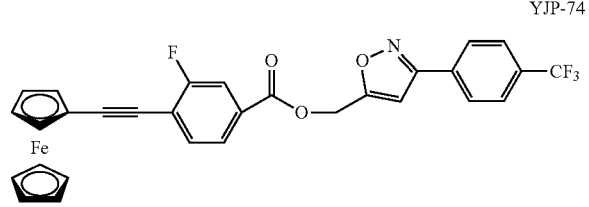
YJP-75
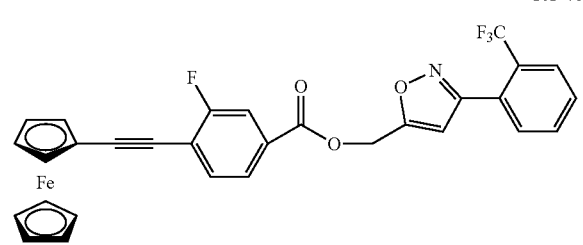
YJP-76
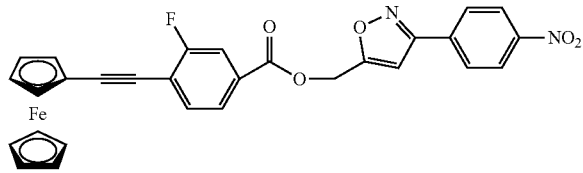
YJP-77
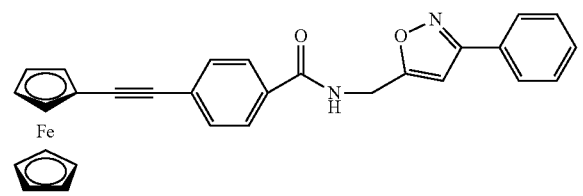
YJP-78
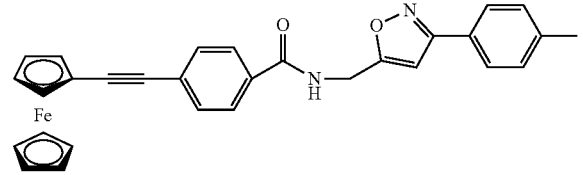
YJP-79
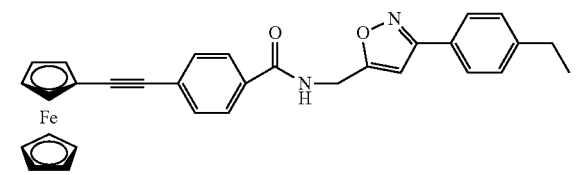
-continued
YJP-80
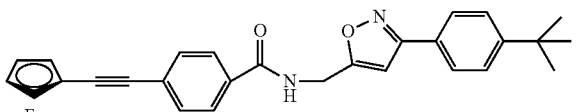
YJP-81
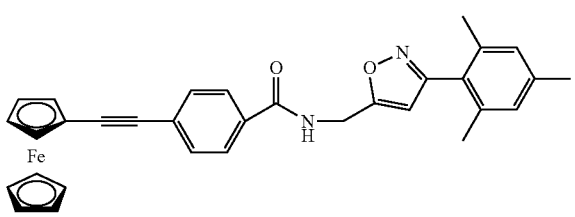
YJP-82
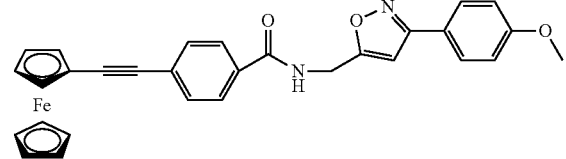
YJP-83
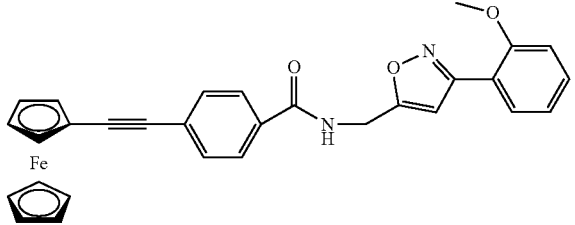
YJP-84
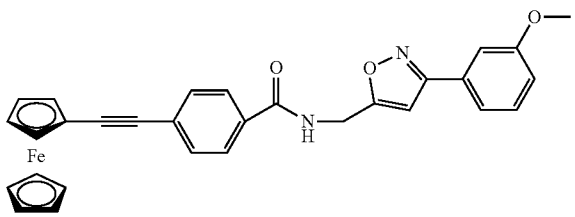
YJP-85
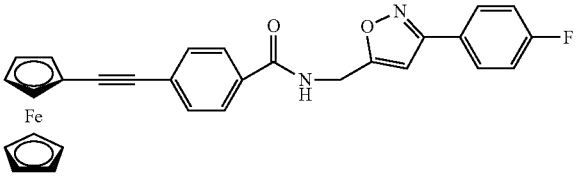
YJP-86

-continued
YJP-87
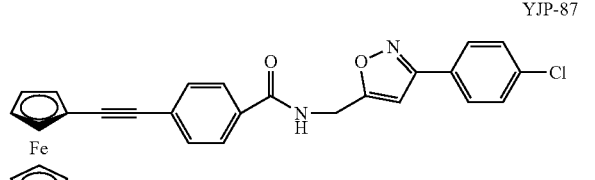
YJP-88
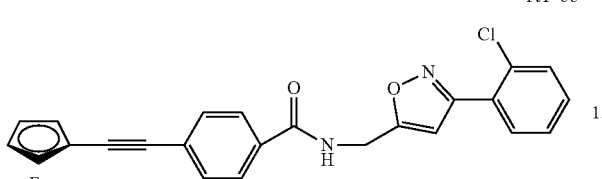
YJP-89
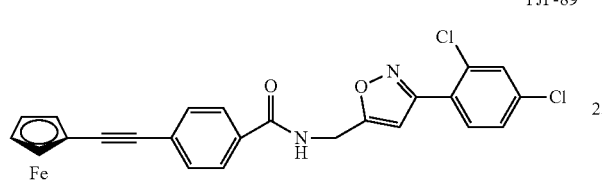
YJP-90
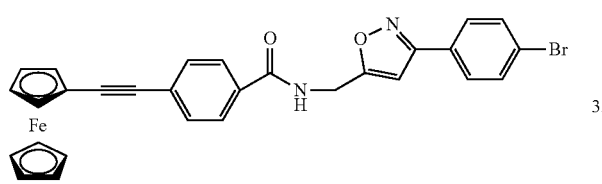
YJP-91
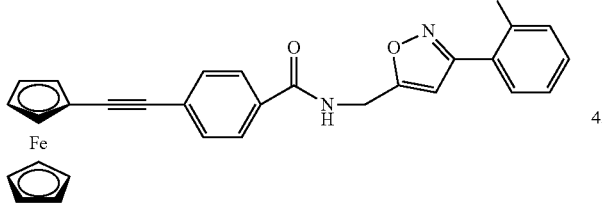
YJP-92
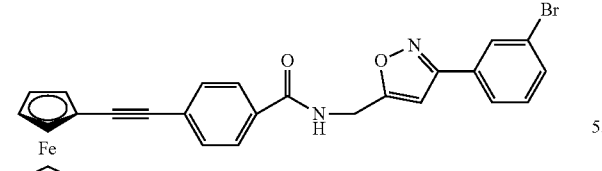
YJP-93
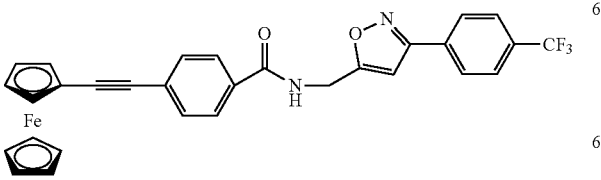
-continued
YJP-94
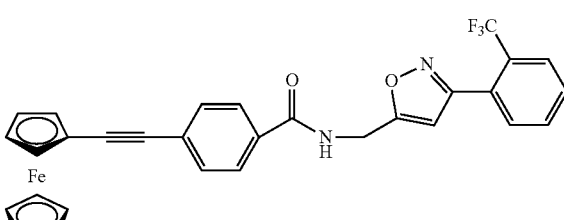
YJP-95
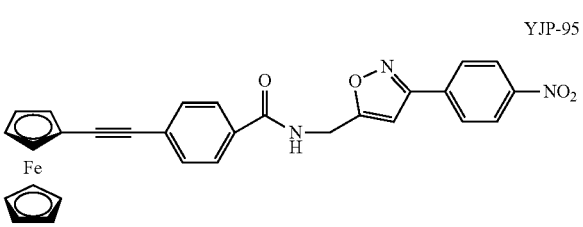
YJP-96
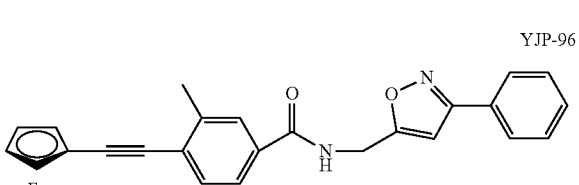
YJP-97
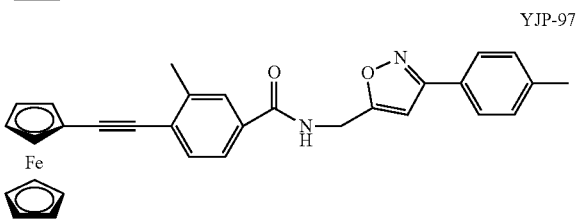
YJP-98
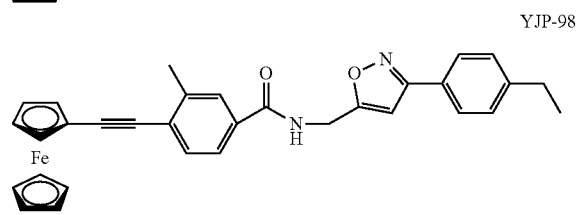
YJP-99
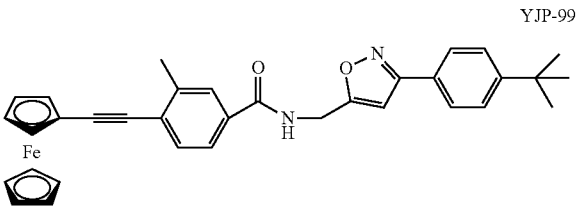
YJP-100
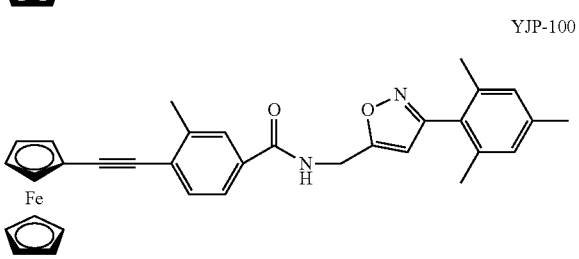

YJP-101
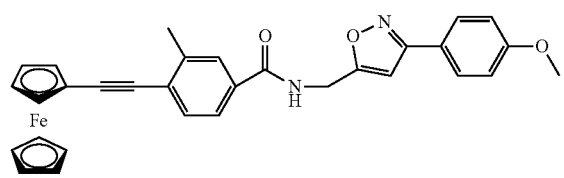
YJP-102
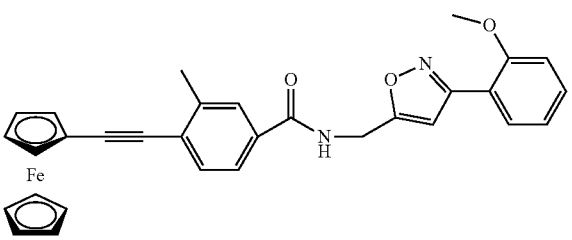
YJP-103
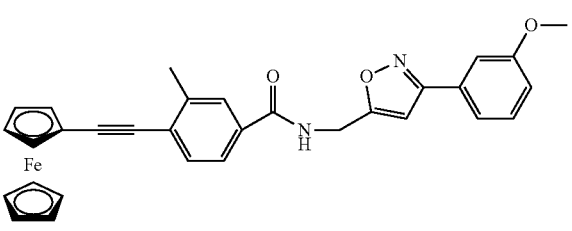
YJP-104
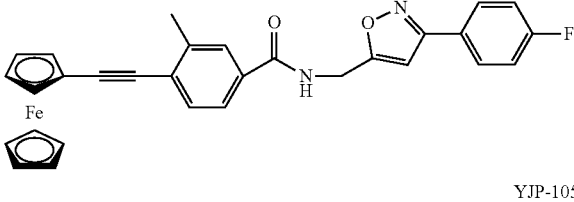
YJP-105
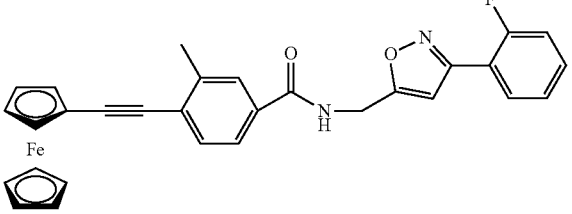
YJP-106
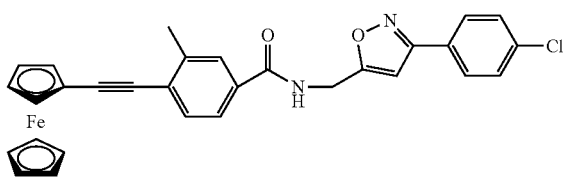
YJP-107
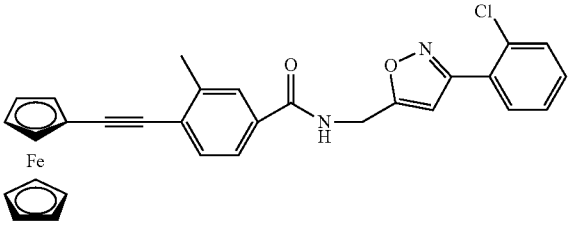
YJP-108
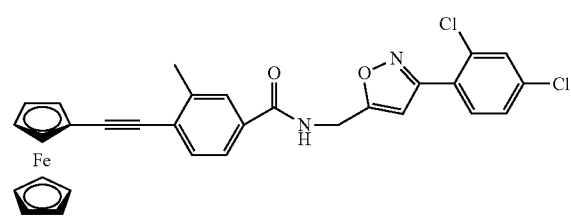
YJP-109
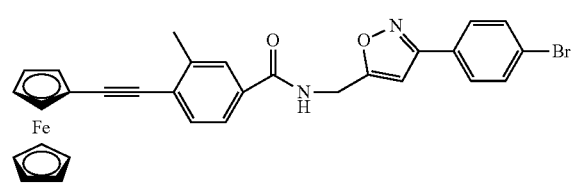
YJP-110
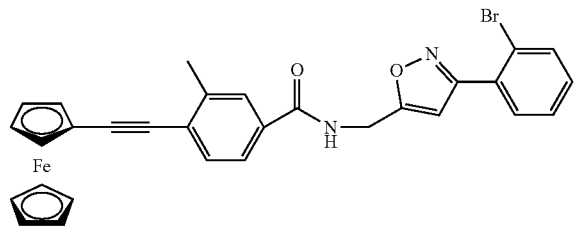
YJP-111
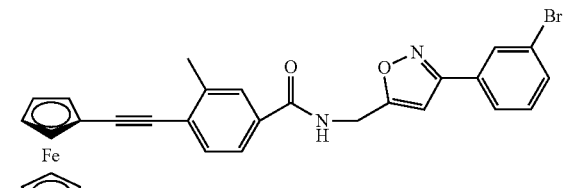
YJP-112
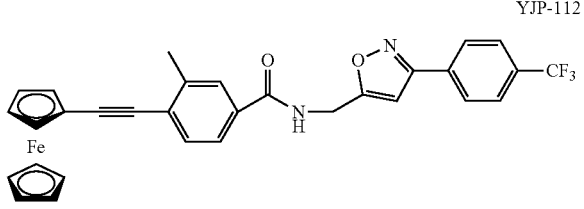
YJP-113
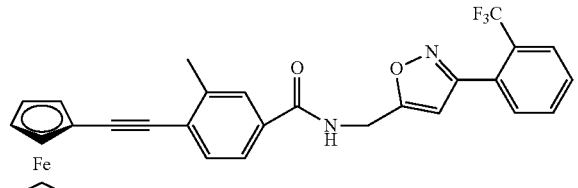
YJP-114
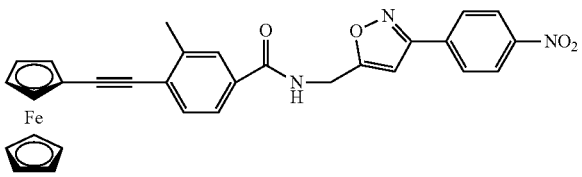

-continued
YJP-115
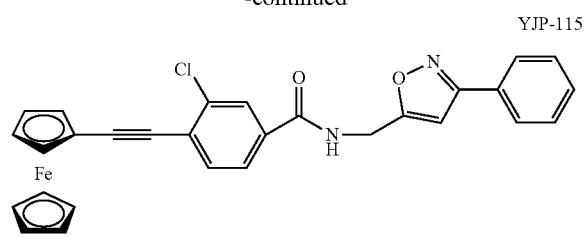
YJP-116
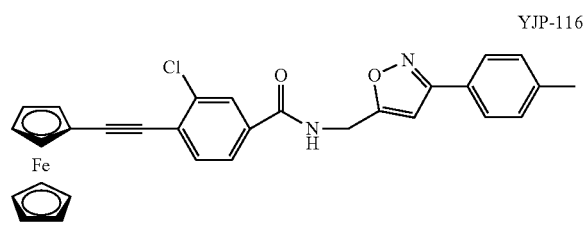
YJP-117
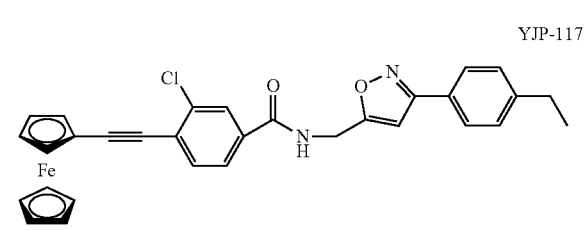
YJP-118
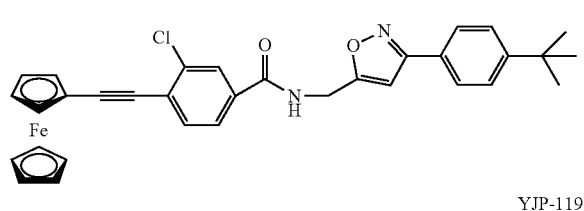
YJP-119
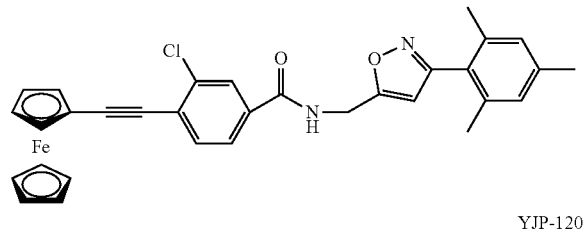
YJP-120
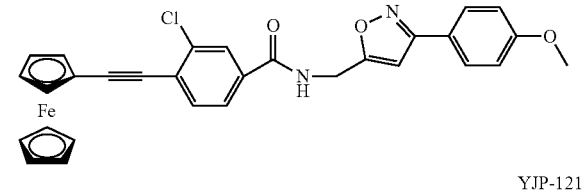
YJP-121
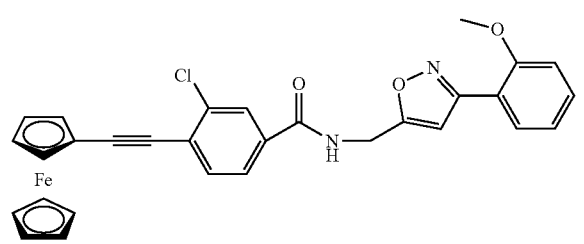
-continued
YJP-122
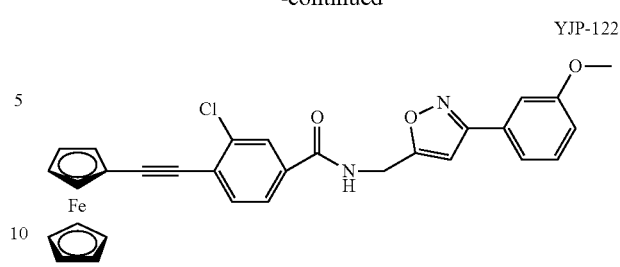
YJP-123
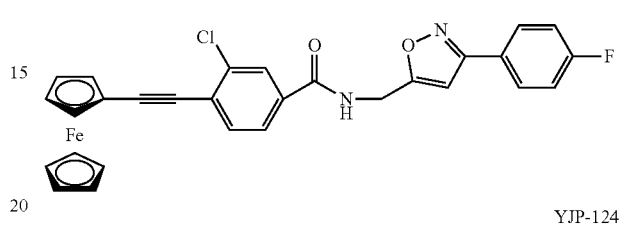
YJP-124
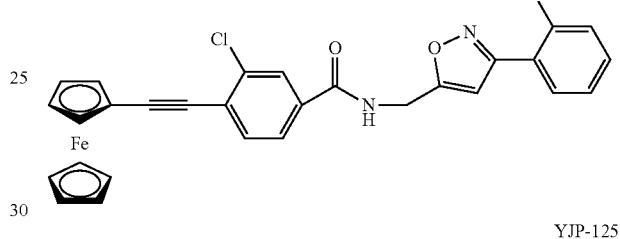
YJP-125
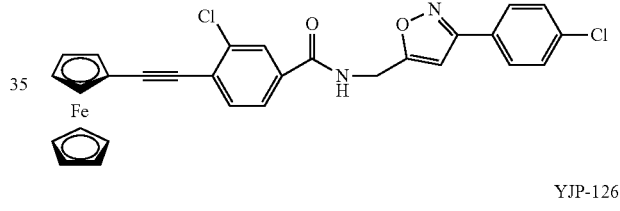
YJP-126
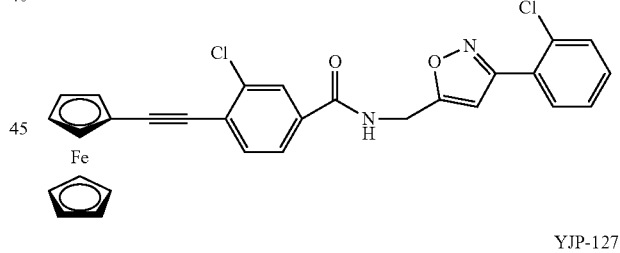
YJP-127
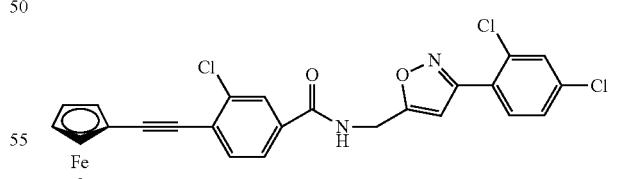
YJP-128
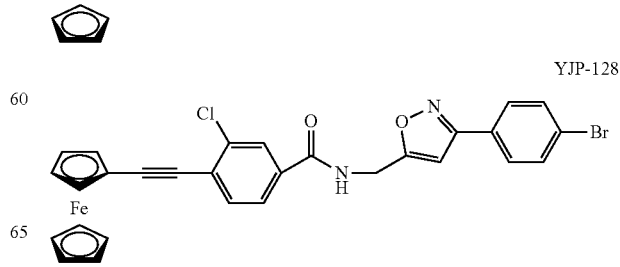

YJP-129
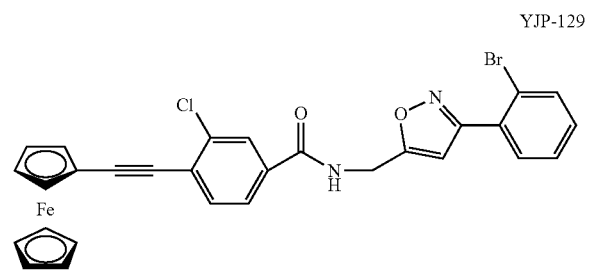
YJP-130
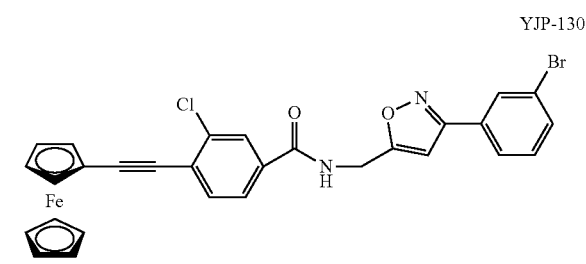
YJP-131
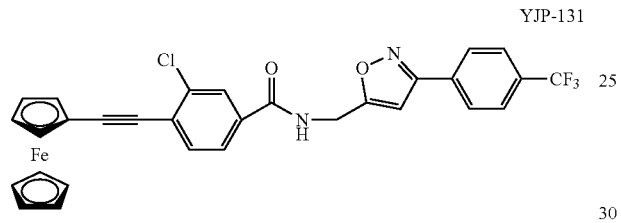
YJP-132
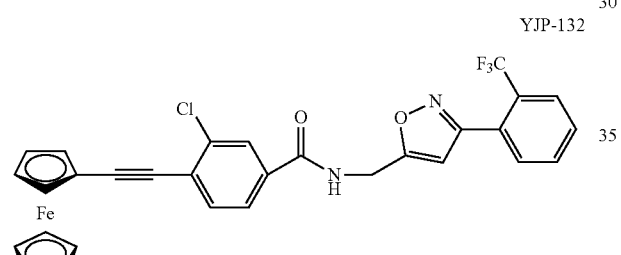
YJP-133
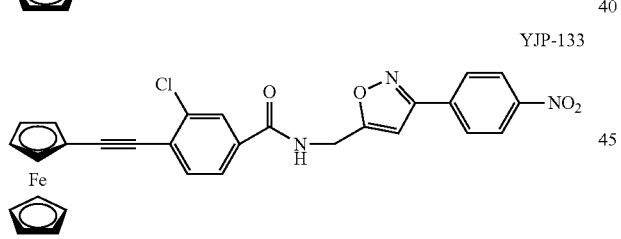
YJP-134
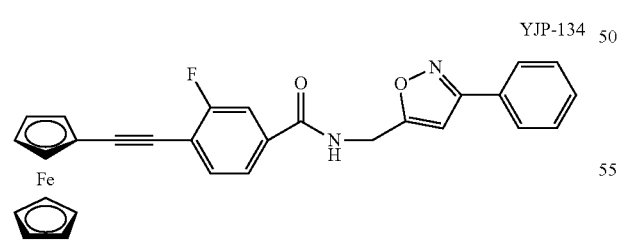
YJP-135
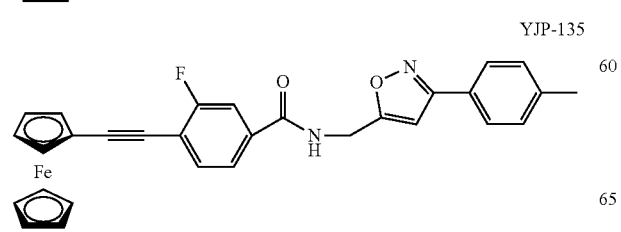
YJP-136
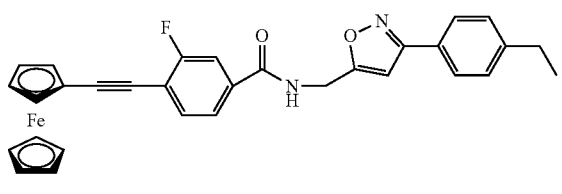
YJP-137
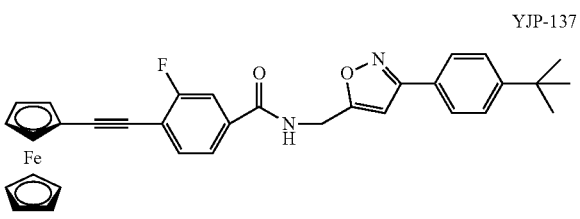
YJP-138
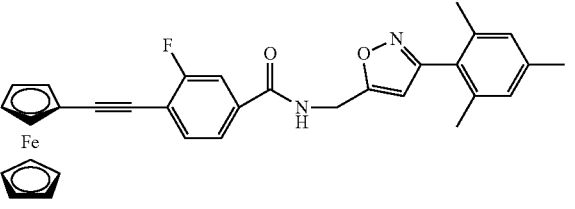
YJP-139
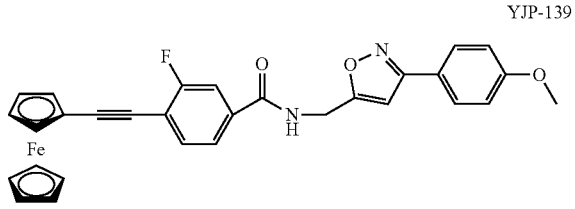
YJP-140
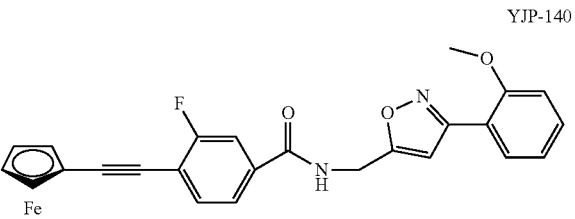
YJP-141
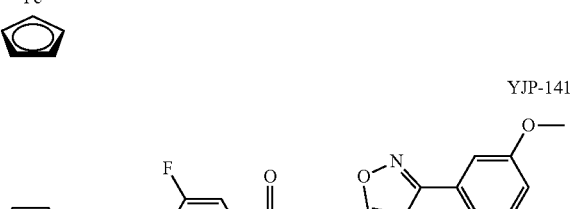
YJP-142
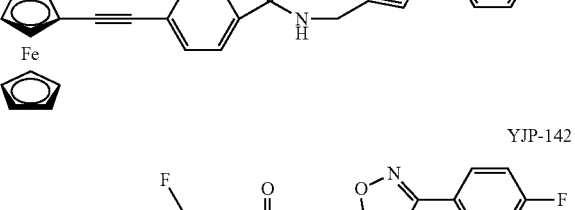

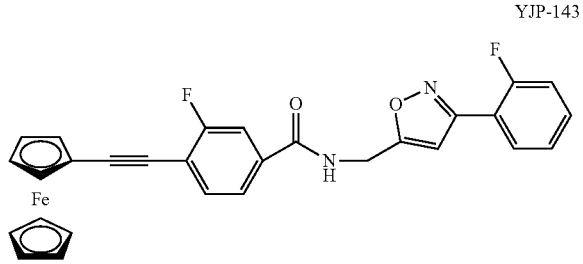
YJP-143

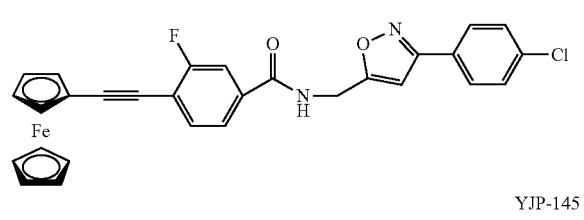
YJP-144

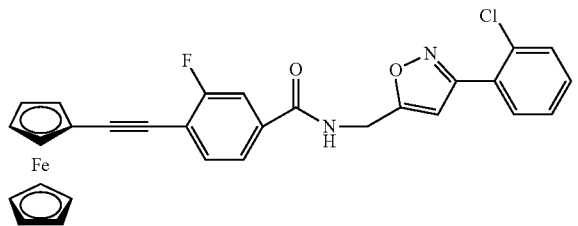
YJP-145

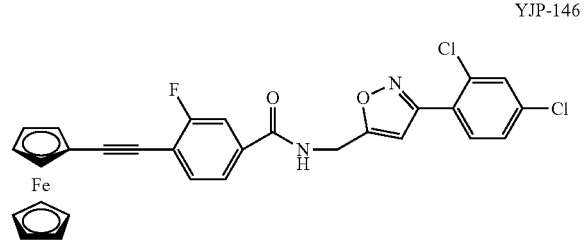
YJP-146

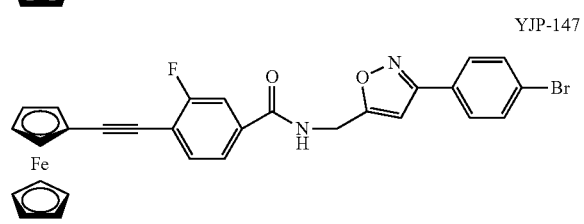
YJP-147

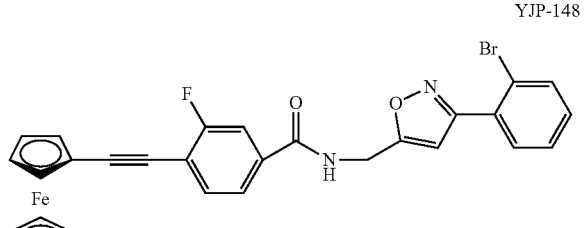
YJP-148

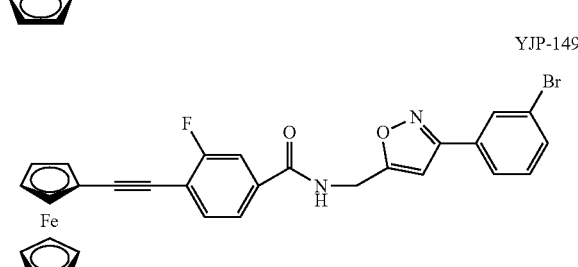
YJP-149

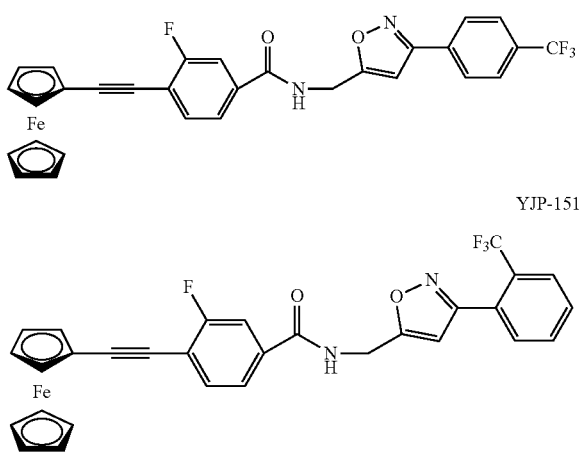

YJP-150

YJP-151

YJP-152

According to an embodiment of the present invention, the pharmaceutically acceptable salt of the ferrocene derivative of formula (I) may be a pharmaceutically acceptable salt formed by the compound of formula (I) and a pharmaceutically acceptable acid or a pharmaceutically acceptable cation. The pharmaceutically acceptable salt includes, but is not limited to, salts of inorganic acids such as hydrochloride, phosphate, diphosphate, hydrobromide, sulfate, sulfinate, nitrate and the like; and salts of organic acids such as lactate, oxalate, malate, maleate, fumarate, tartrate, succinate, citrate, sulfonate, tosilate, 2-hydroxyethyl sulfonate, benzoate, salicylate, stearate, trifluoroacetate or salts of amino acids and alkanoic acids (e.g., acetate, salts of HOOC—(CH$_2$)n-COOH (where n is an integer from 1 to 4)), and the like. The pharmaceutically acceptable cation includes, but is not limited to, sodium, potassium, calcium, aluminum, lithium and ammonium.

According to an embodiment of the present invention, the solvate includes hydrates and alcoholates.

The present invention also provides a preparation method for the ferrocene derivative of formula (I), comprising the following steps:

(1) reacting ferrocenylethyne with a compound of formula A to give a ferrocene-containing intermediate B;

wherein the compound of formula A is 3-(R$_1$)-4-bromobenzoic acid with a structural formula of

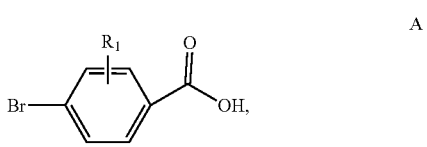

A and the compound of formula B has a structural formula of

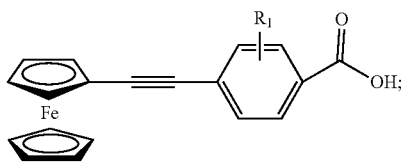

wherein $R_1$ is defined as above;

(2) reacting the intermediate B with a compound of formula C to give the ferrocene derivative of formula (I);

wherein the compound of formula C has a structural formula of

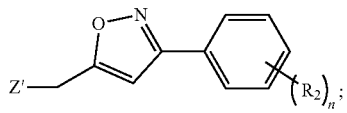

wherein $R_2$ and n are defined as above, and Z' represents $NH_2$, OH or SH;

preferably, the compound of formula C is 3-substituted phenyl-5-hydroxymethyl-isoxazole (II), 3-substituted phenyl-5-mercaptomethyl-isoxazole, or 3-substituted phenyl-5-aminomethyl-isoxazole (III).

According to an embodiment of the present invention, the reaction in step (1) is performed in the presence of a palladium(II) compound, an organophosphorus compound and a copper(I) compound. For example, the palladium(II) compound may be selected from palladium(II) compounds known in the art, such as bis(triphenylphosphine)palladium chloride, tetrakis(triphenylphosphine)palladium and [1,1'-bis(diphenylphosphino) ferrocene]dichloropalladium; for example, the organophosphorus compound may be selected from organophosphorus compounds known in the art, such as triphenylphosphorus; for example, the copper(I) compound may be selected from copper(I) compounds known in the art, such as copper(I) iodide.

According to an embodiment of the present invention, the reactions in step (1) and step (2) are performed in a dried organic solvent. For example, the dried organic solvent may be selected from aromatic hydrocarbons, halohydrocarbons, tetrahydrofuran (THF), dimethylsulfoxide (DMSO), dioxane, acetonitrile, pyridine, DMF and ionic liquids; preferably, the dried organic solvent is selected from tetrahydrofuran, chloroform, 1,2-dichloromethane, benzene, toluene, xylene, acetonitrile, pyridine, DMF and ionic liquids; and more preferably, the dried organic solvent is tetrahydrofuran. According to an embodiment of the present invention, the reaction in step (1) is also performed in the presence of an alkaline deacid reagent. Preferably, the alkaline deacid reagent is selected from organic bases and/or inorganic bases. For example, the organic base is selected from one, two or more of triethylamine, tripropylamine, DMAP, DMF, N-methylmorpholine and the like; for example, the inorganic base is selected from one, two or more of potassium carbonate, sodium hydride, sodium carbonate and the like. More preferably, the alkaline deacid reagent is triethylamine.

According to an embodiment of the present invention, the molar volume ratio (mmol/mL) of the ferrocenylethyne in step (1) to a mixture of a dried organic solvent and an alkaline deacid reagent is 0.5:6-5:6, for example, 0.952:6.

According to an embodiment of the present invention, step (1) comprises the following process: dispersing ferrocenylethyne and a compound of formula A in a mixture of a dried organic solvent and an alkaline deacid reagent, adding a palladium (II) compound, an organophosphorus compound and a copper (I) compound to the mixture while stirring, stirring the reaction system, refluxing the reaction system, filtering the reaction system, and concentrating the filtrate to give intermediate B.

According to an embodiment of the present invention, the reactions in step (1) and step (2) are performed under inert atmosphere, for example, under nitrogen atmosphere.

According to an embodiment of the present invention, the reaction in step (2) is performed in a dried organic solvent. The organic solvent is defined as above.

According to an embodiment of the invention, the reaction in step (2) is performed in the presence of a condensing agent. For example, the condensing agent may be selected from one, two or more of DCC, DMAP, NMM, HOBt and HATU; for example, the condensing agent may be selected from a combination of DCC and DMAP, a combination of DCC, HOBt and NMM, a combination of DCC and NMM, and a combination of DCC and HATU.

According to an embodiment of the present invention, the 3-substituted phenyl-5-hydroxymethyl-isoxazole (II) or 3-substituted phenyl-5-aminomethyl-isoxazole (III) in step (2) is a compound known in the art, and can be prepared by referring to the optimized process described in Chinese Patent No. CN103360382A. Specifically, the preparation route is shown in the figure below:

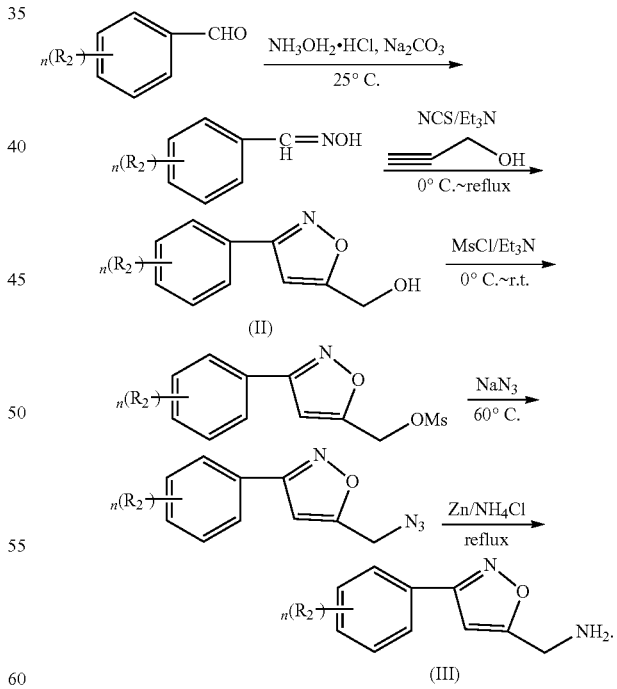

When Z' is SH, the compound of formula C is 3-substituted phenyl-5-mercaptomethyl-isoxazole prepared by referring to the synthesis process of the compound of formula (II) with propynethiol as the starting material.

According to an embodiment of the present invention, the temperature of the reaction in step (1) or step (2) is any temperature point within the range of −20° C. to a reflux temperature, preferably any temperature point within the range of 0° C. to a reflux temperature, and further preferably any temperature point within the range of room temperature to a reflux temperature.

According to an embodiment of the present invention, step (2) comprises the following process: adding the intermediate B to a dried organic solvent, then adding a condensing agent for reaction, followed by adding the compound of formula C for reaction to give the ferrocene derivative of formula (I).

Preferably, the reaction time after adding the condensing agent is 20-40 min, for example, 30 min.

Preferably, the reaction time after adding the compound of formula C is 20-40 min, for example, 30 min.

Preferably, the synthetic route for the compound of formula (I) is shown in the figure below:

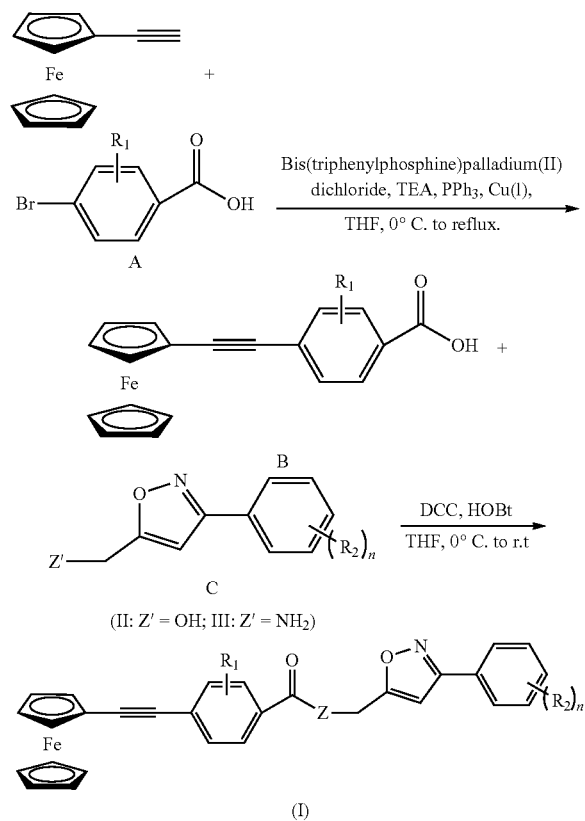

Any functional group in the compound of formula C may be protected if desired; and thereafter, if necessary (in any order):
(a) any protecting agent is removed, and
(b) a pharmaceutical composition of the compound of formula (I) is formed.

The present invention also provides a pharmaceutical composition comprising the ferrocene derivative of formula (I), the pharmaceutically acceptable salt thereof or the solvate thereof.

According to an embodiment of the present invention, the pharmaceutical composition also comprises at least one pharmaceutically acceptable pharmaceutical adjuvant; for example, at least one pharmaceutically acceptable, inert and non-toxic pharmaceutical excipient may be selected from excipients, carriers and/or diluents. The pharmaceutically acceptable pharmaceutic adjuvant refers to an inert and nontoxic pharmaceutic adjuvant.

According to an embodiment of the present invention, the pharmaceutical adjuvant may also be selected from one or more of fillers, disintegrants, lubricants, glidants, effervescent agents, flavoring agents, preservatives and pharmaceutically acceptable auxiliary materials for coating materials.

The present invention also provides a pharmaceutical preparation comprising the ferrocene derivative of formula (I), the pharmaceutically acceptable salt thereof or the solvate thereof.

According to an embodiment of the present invention, the pharmaceutical preparation comprises the pharmaceutical composition described above.

According to an embodiment of the present invention, the pharmaceutical preparation is a solid oral preparation, a liquid oral preparation or an injection.

Preferably, the preparation is selected from tablets, dispersible tablets, enteric-coated tablets, chewable tablets, orally disintegrating tablets, capsules, granules, oral solutions, water solution for injection, lyophilized powder for injection, large infusion solutions and small infusion solutions.

The present invention also provides the ferrocene derivative of formula (I) or the pharmaceutically acceptable salt thereof according to an embodiment of the present invention as a drug, in particular, a drug or a lead compound effective for treating tumors/cancers.

The present invention also provides use of the ferrocene derivative of formula (I), the pharmaceutically acceptable salt thereof, the solvate thereof, or the pharmaceutical composition comprising the same in the preparation of anti-tumor or anti-cancer drugs.

The present invention also provides use of the ferrocene derivative of formula (I), the pharmaceutically acceptable salt thereof or the solvate thereof as an anti-tumor/anti-cancer lead compound.

Preferably, the tumor or cancer is selected from at least one of bladder cancer, ovarian cancer, breast cancer, gastric cancer, esophageal cancer, lung cancer, head and neck cancer, colon cancer, pharyngeal cancer, pancreatic cancer and the like; preferably, the lung cancer is non-small cell lung cancer; and more preferably, the tumor or cancer is non-small cell lung cancer, gastric cancer, breast cancer and/or cervical cancer.

The present invention also provides a method for preventing and/or treating diseases related to the above tumors/cancers, comprising administering to a patient (such as a human) in need thereof an effective amount of the ferrocene derivative of formula (I), the pharmaceutically acceptable salt thereof, the solvate thereof, the pharmaceutical composition or the pharmaceutical preparation.

The term "effective amount" refers to an amount of the at least one compound and/or at least one pharmaceutically acceptable salt that is effective to "treat" a disease or disorder in a subject. In the case of cancer, the effective amount has the following effects: reducing the number of cancer or tumor cells; shrinking the size of tumor; inhibiting or preventing the invasion of tumor cells into peripheral organs, for example, the spread of tumor into soft tissues or bones; inhibiting or preventing the metastasis of tumor; inhibiting or preventing the growth of tumor; alleviating one or more symptoms associated with cancer to some extent; reducing morbidity and mortality; improving the quality of life; or a combination of the above effects. An effective amount may be an amount that reduces the symptoms of disease by inhibiting EGFR activity. In vivo efficacy of cancer treatments can be measured by assessing, for example, survival, time to disease progression (TTP), response rates (RR), duration of response, and/or quality of life. Those skilled in the art will understand that the effective amount may vary with the route of administration, the dosage of excipient, and the combined use with other drugs.

The term "effective amount" may also refer to a dosage of the at least one compound and/or at least one pharmaceutically acceptable salt thereof that is effective to inhibit overexpression and/or overactivity of EGFR.

Beneficial Effects of the Present Invention

The present invention provides a novel ferrocene derivative of formula (I). The ferrocene derivative has good inhibition effect on tumors or cancers. The results of research on the in vitro inhibition of human lung adenocarcinoma cell line (A549), breast cancer cell line (MCF-7) and cervical cancer cell line (Hela) show that: such compounds have strong inhibitory activity against human lung adenocarcinoma cell line (A549), breast cancer cell line (MCF-7) and cervical cancer cell line (Hela). Such compounds can be used as candidate compounds or lead compounds for anticancer drugs.

DETAILED DESCRIPTION

The present invention will be further illustrated with reference to the following examples. It should be noted that the following examples are not intended to limit the scope of the present invention, and any modifications made on the basis of the present invention do not depart from the spirit of the present invention.

Among them, the synthesis of the intermediates and target compounds are all described in representative examples, and other intermediates and target compounds are synthesized in the same way as the synthesis of the representative compounds.

Instruments and Reagents:

AVANCE III NMR spectrometer (400 MHz, DMSO-$d_6$, TMS as internal standard), ion trap liquid chromatography-mass spectrometer (DECAX-30000 LCQ Deca XP), Shimadzu FTIR-84005 (manufactured by Shimadzu corporation, Japan), XT5 digital micro melting point apparatus (manufactured by Beijing Keyi Electric Optical Instrument Factory), and wavelength-tunable microplate reader (Molecular Devices SPECTRAMAX190).

Example 1. Synthesis of Intermediates 3-substituted phenyl-5-hydroxymethyl-isoxazole (II) and 3-substituted phenyl-5-aminomethyl-isoxazole (III)

With substituted benzaldehyde as the starting material, the compounds were prepared by oxime synthesis, 1,3-dipolar cycloaddition, methylsulfonyl esterification, azidation and reduction ($R_2$ is selected from hydrogen, halogen, $C_1$-$C_6$ alkyl, $C_1$-$C_6$ alkoxy, $C_1$-$C_6$ haloalkyl and nitro; n is an integer from 0 to 5), and the specific route was shown in the following figure:

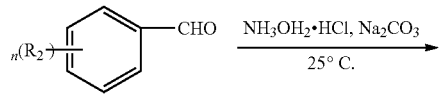

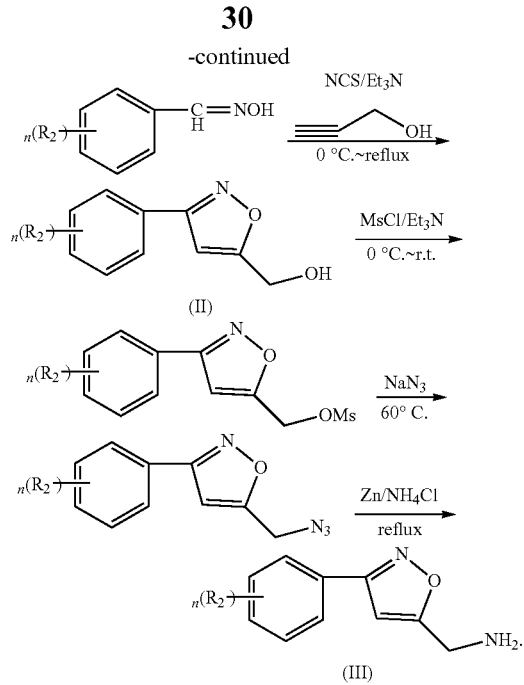

Specific synthetic processes of the intermediates 3-substituted phenyl-5-hydroxymethyl-isoxazole (II) and 3-substituted phenyl-5-aminomethyl-isoxazole (III) are detailed in previous Chinese Patent Nos. CN103360382A, CN103664991A and CN103601762A by the applicant.

Example 2. Synthesis of Ferrocene-Containing Intermediate B (Exemplified by the Synthesis with Ferrocenylethyne and p-bromobenzoic Acid)

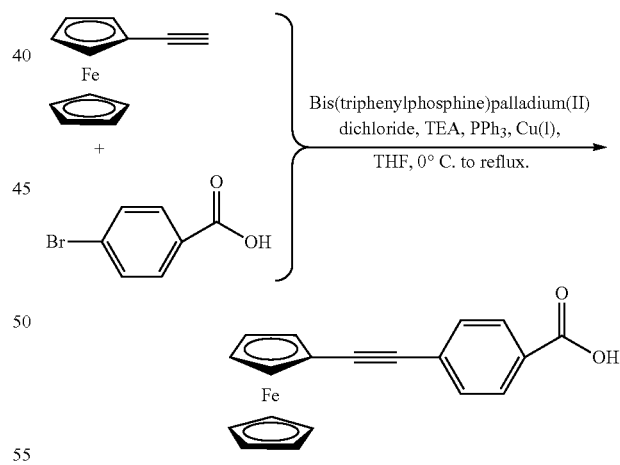

Ferrocenylethyne (2.00 g, 9.52 mmol) and 4-bromobenzoic acid (1.91 g, 9.52 mmol) were added into a 250 mL two-necked round-bottom flask, and then dried tetrahydrofuran and triethylamine (60 mL) were added. The reaction system was stirred at room temperature for 10 min under nitrogen atmosphere. Then the reaction system was added with triphenylphosphine (0.2 g, 0.76 mmol), bis(triphenylphosphine)palladium chloride (0.28 g, 0.38 mmol) and copper(I) iodide (0.07 g, 0.38 mmol), stirred at room temperature for 20 min, and refluxed. The whole reaction was performed under nitrogen atmosphere. After the reaction system was completed, as detected by TLC, the reaction mixture was filtered, and the filtrate was concentrated to give a crude product, which was separated by column chromatography ($V_{(petroleum\ ether)}:V_{(ethyl\ acetate)}$=5:1-1:1) to give 4-ferrocenylethynyl-benzoic acid (2.53 g, 81% yield) in the form of a light yellow solid. $^1$H NMR of 4-ferrocenylethynyl-benzoic acid (400 MHz, DMSO-d$_6$): 4.29 (s, 5H, $\eta^5$-C$_5$H$_5$), 4.38 (2H, t, J=2.0 Hz), 4.61 (2H, t, J=2.0 Hz), 7.58 (2H, d, J=9.2 Hz), 7.90 (2H, d, J=9.2 Hz), 12.83 (1H, brs, —COOH).

The other intermediates were prepared using 3-(R$_1$)-4-bromobenzoic acid with R$_1$ by referring to the reaction of ferrocenylethyne with 4-bromobenzoic acid.

Example 3. Synthesis of the Target Ester Compound of Formula (I) (YJP-1)

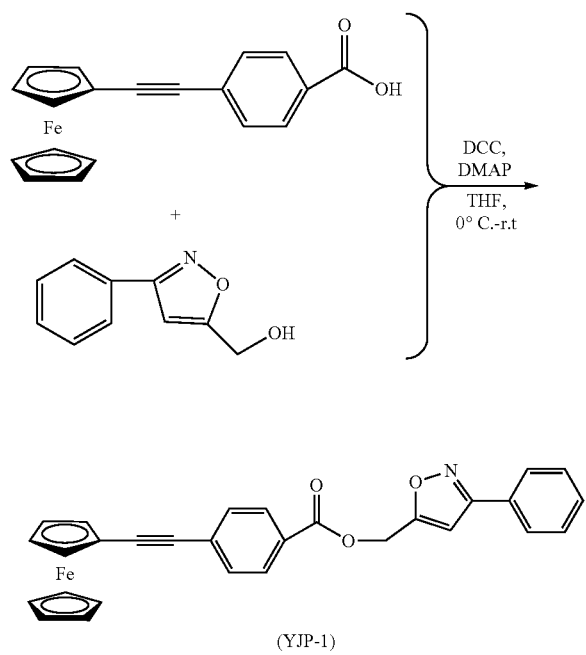

(YJP-1)

4-ferrocenylethynyl-benzoic acid prepared in Example 2 (0.165 g, 0.5 mmol) and dried THF (8 mL) were added to a 50 mL single-necked round-bottom flask, and then DCC (0.103 g, 0.5 mmol) and DMAP (0.061 g, 0.5 mmol) were added while stirring. The reaction system was reacted at 0° C. for 30 min. Then the reaction system was added with 3-phenyl-5-hydroxymethyl-isoxazole (0.088 g, 0.5 mmol), reacted at 0° C. for 30 min, and warmed to room temperature. The whole reaction was performed under nitrogen atmosphere. After the reaction was completed, as detected by TLC, the reaction solution was concentrated under reduced pressure, and the residue was separated by column chromatography ($V_{(petroleum\ ether)}:V_{(ethyl\ acetate)}$=5:1-2:1) to give the target compound (YJP-1). The remaining compounds YJP-2 to YJP-76 were synthesized by referring to the synthesis process of the target compound YJP-1.

Example 4. Synthesis of the Target Amide Compound of Formula (I) (YJP-77)

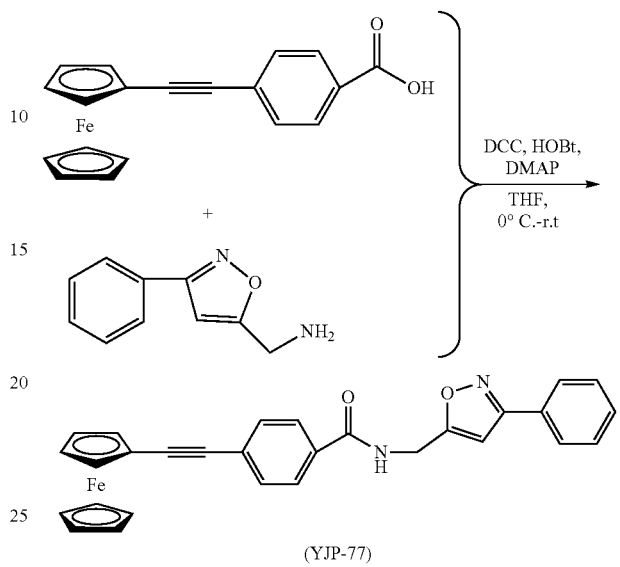

(YJP-77)

4-ferrocenyl-benzoic acid prepared in Example 2 (0.165 g, 0.5 mmol) and dried THF (8 mL) were added to a 50 mL single-necked round-bottom flask, and then DCC (0.103 g, 0.5 mmol), HOBT (0.068 g, 0.5 mmol) and DMAP (0.061 g, 0.5 mmol) were added while stirring. The reaction system was reacted at 0° C. for 30 min. Then the reaction system was added with 3-phenyl-5-aminomethyl-isoxazole (0.087 g, 0.5 mmol), reacted at 0° C. for 30 min, and warmed to room temperature. The whole reaction was performed under nitrogen atmosphere. After the reaction was completed, as detected by TLC, the reaction solution was concentrated under reduced pressure, and the residue was separated by column chromatography ($V_{(petroleum\ ether)}:V_{(ethyl\ acetate)}$=5:1-2:1) to give the target compound (YJP-77).

The remaining compounds YJP-78 to YJP-152 were synthesized by referring to the synthesis process of the target compound YJP-77.

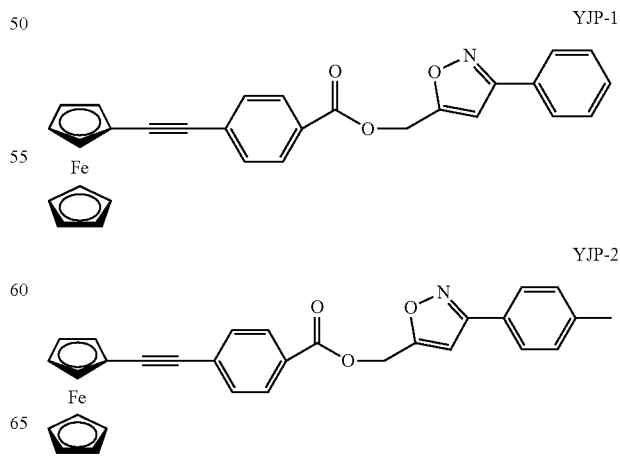

YJP-3
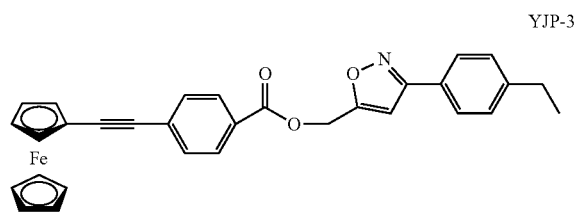
YJP-4
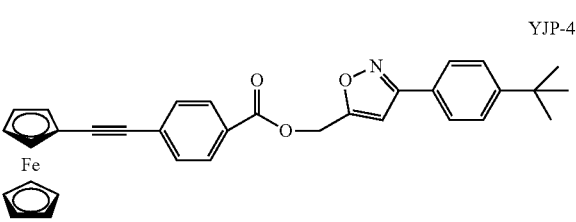
YJP-5
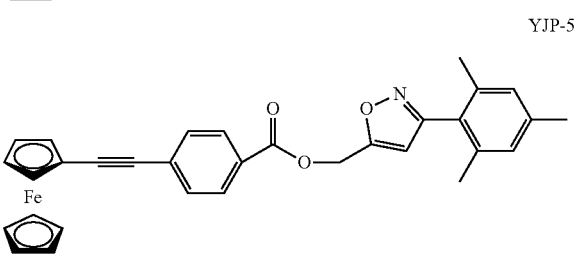
YJP-6
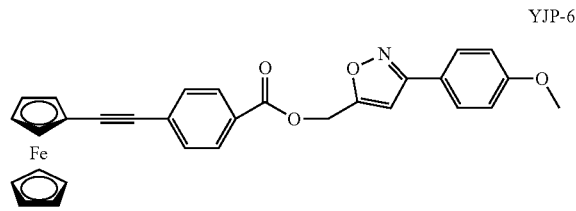
YJP-7
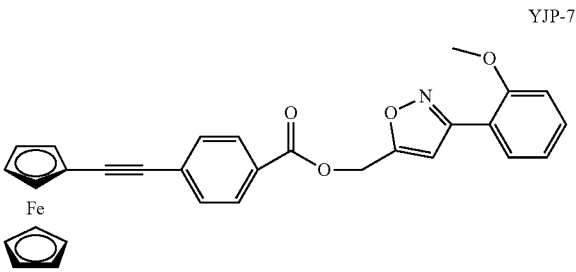
YJP-8
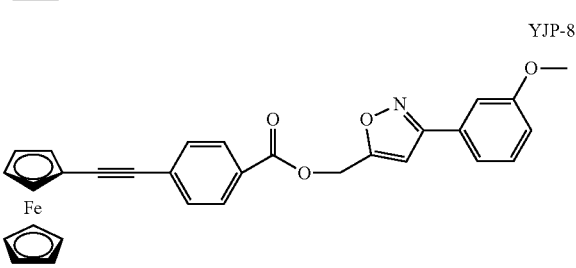
YJP-9
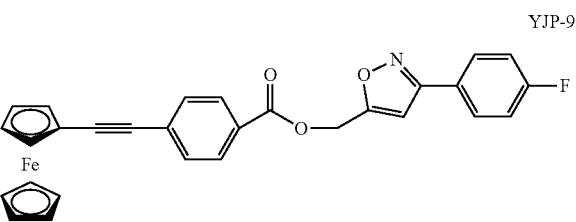
YJP-10
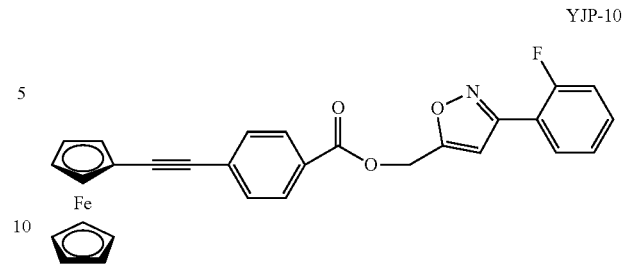
YJP-11
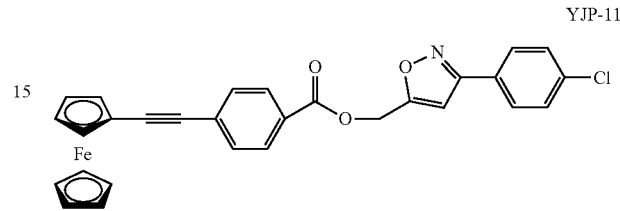
YJP-12
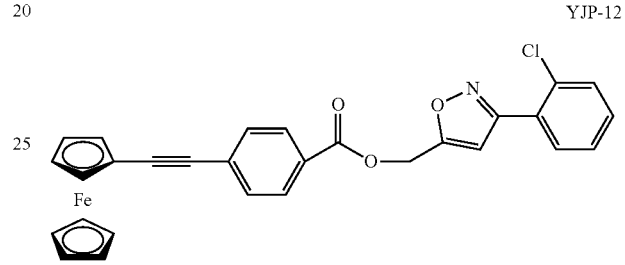
YJP-13
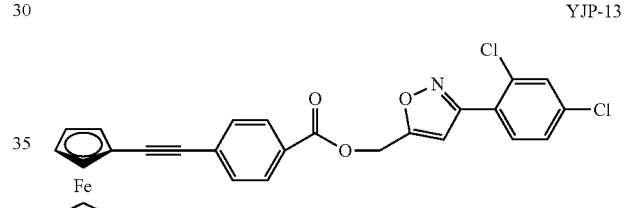
YJP-14
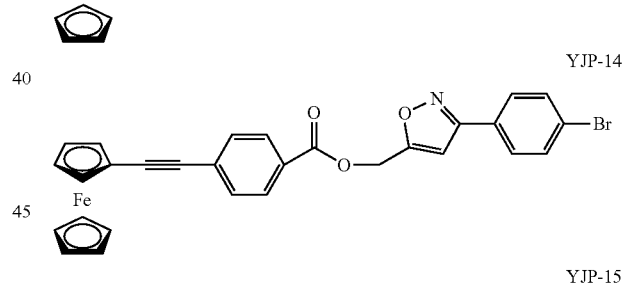
YJP-15
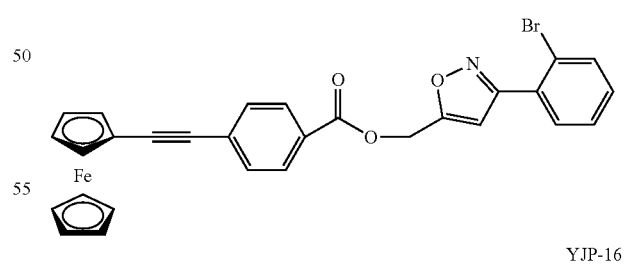
YJP-16
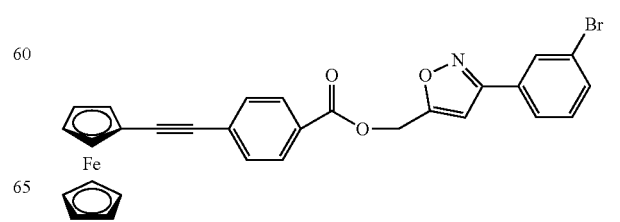

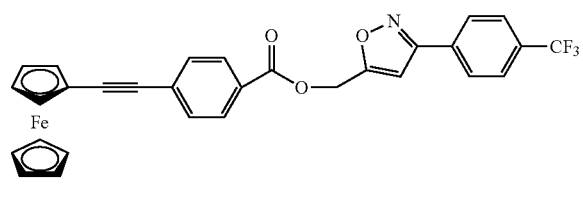
YJP-17
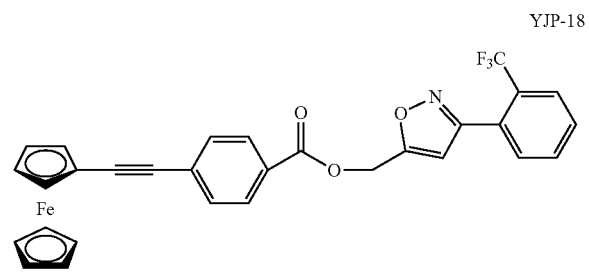
YJP-18
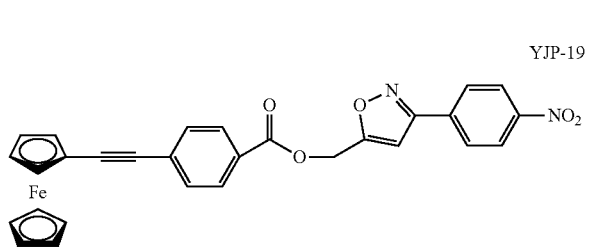
YJP-19
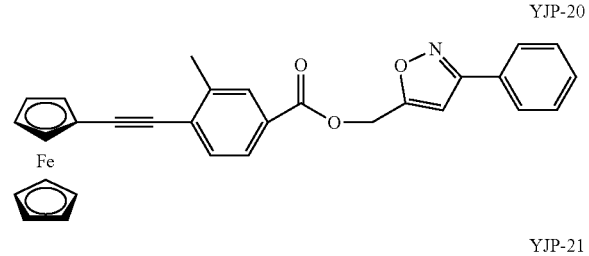
YJP-20
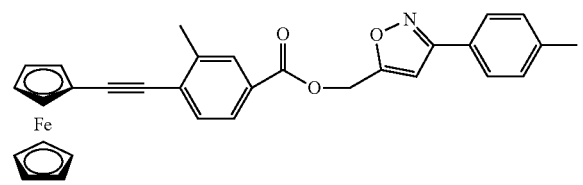
YJP-21
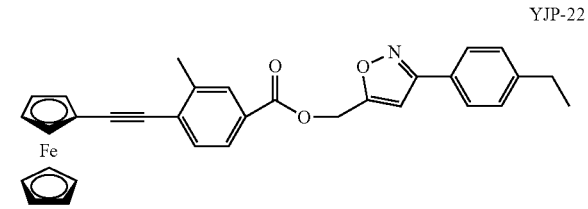
YJP-22
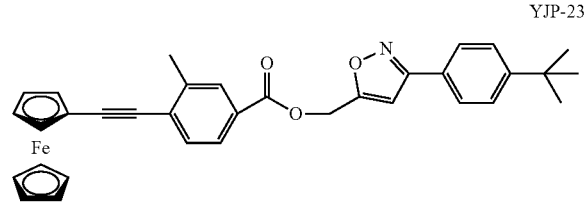
YJP-23
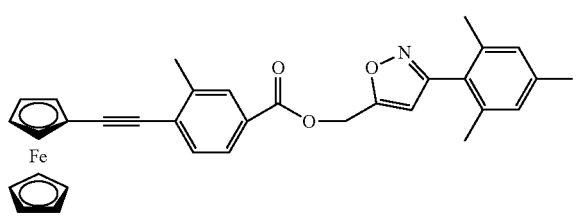
YJP-24
YJP-25
YJP-26
YJP-27
YJP-28
YJP-29
YJP-30

YJP-31
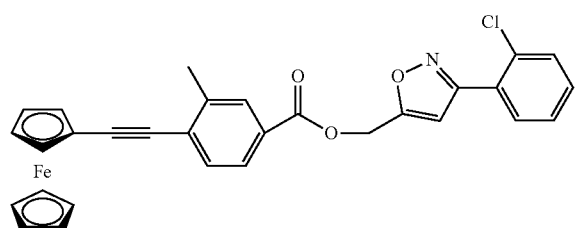
YJP-32
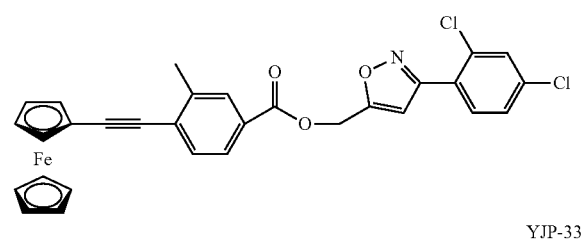
YJP-33
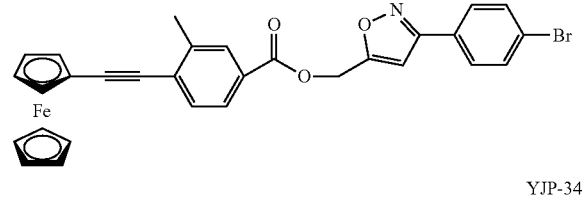
YJP-34
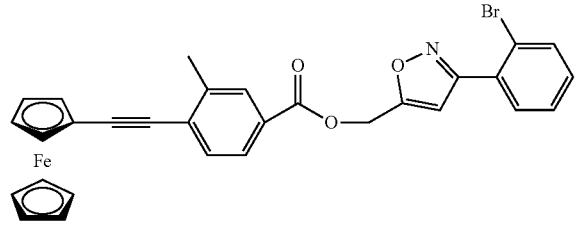
YJP-35
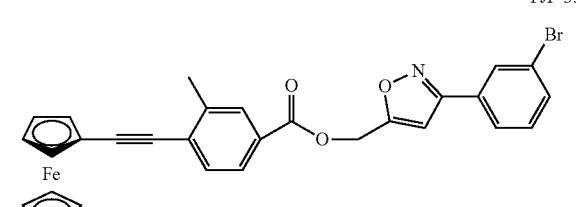
YJP-36
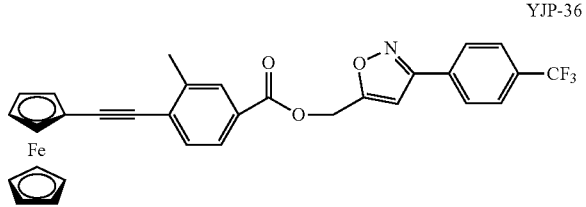
YJP-37
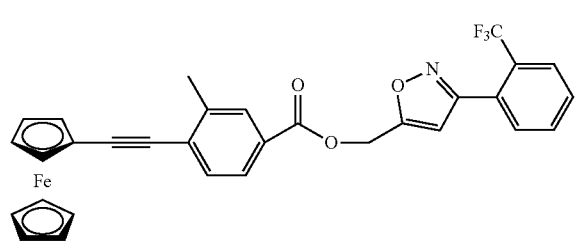
YJP-38
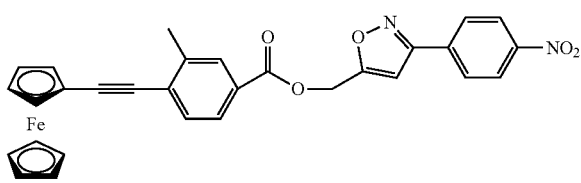
YJP-39
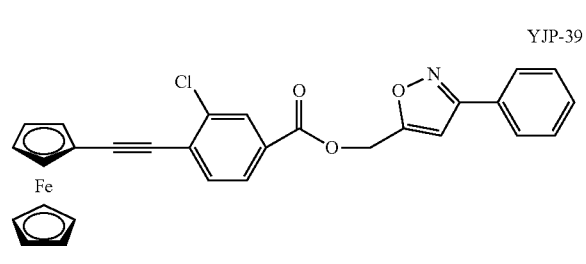
YJP-40
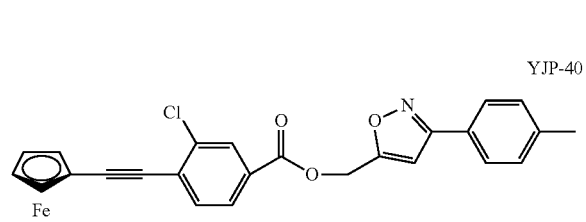
YJP-41
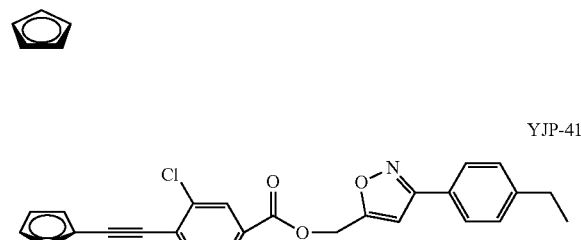
YJP-42
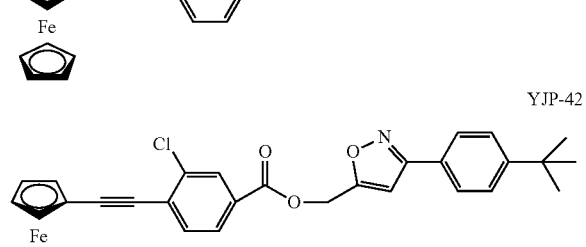
YJP-43
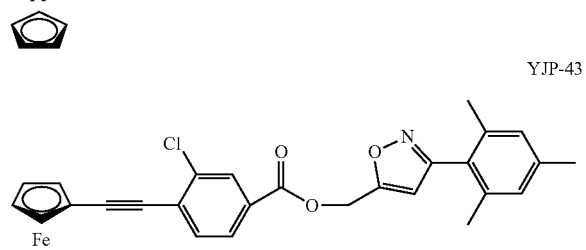
YJP-44
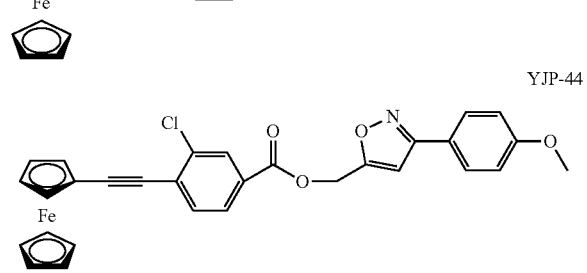

-continued
YJP-45
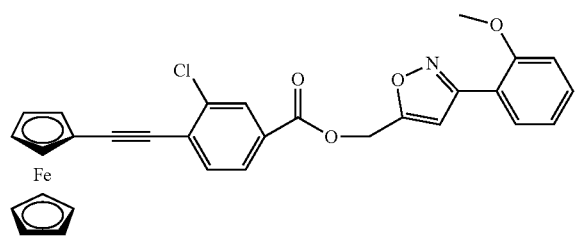
YJP-46
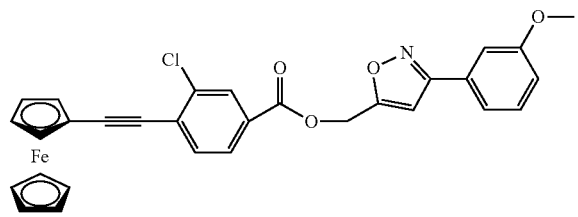
YJP-47
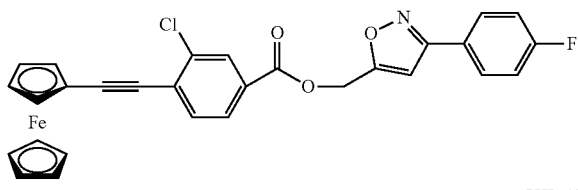
YJP-48
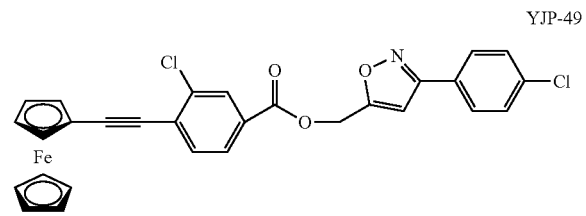
YJP-49
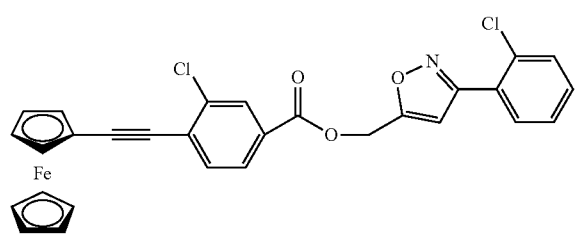
YJP-50
-continued
YJP-52
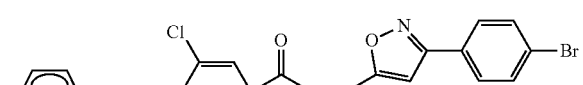
YJP-53
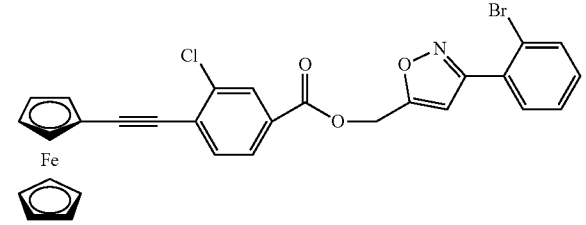
YJP-54
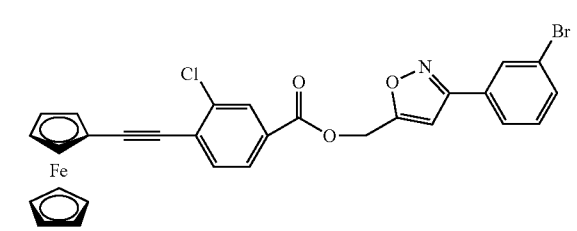
YJP-55
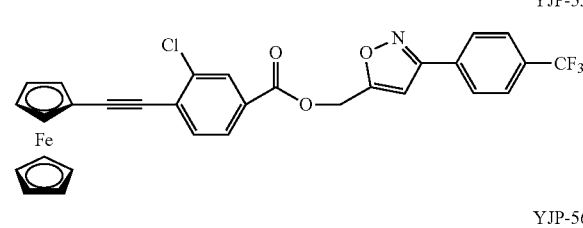
YJP-56
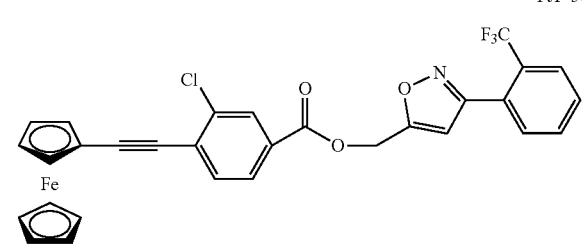
YJP-57
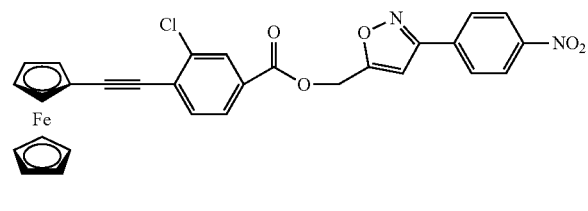
YJP-58
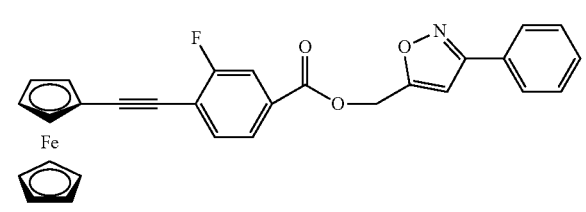
YJP-51

-continued
YJP-59
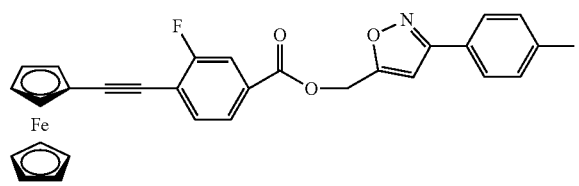
YJP-60
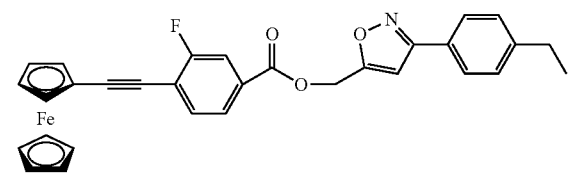
YJP-61
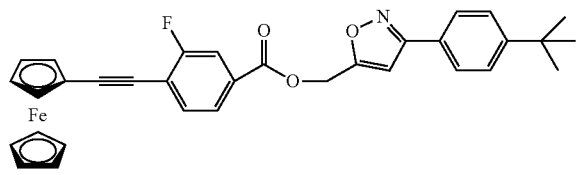
YJP-62
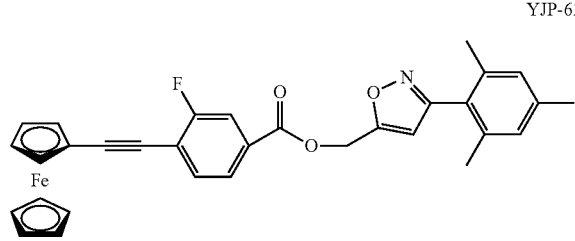
YJP-63
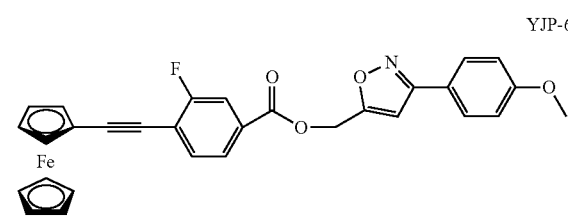
YJP-64
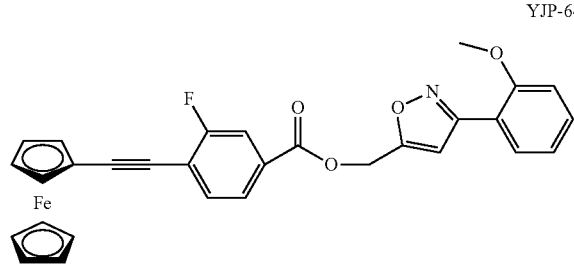
YJP-65
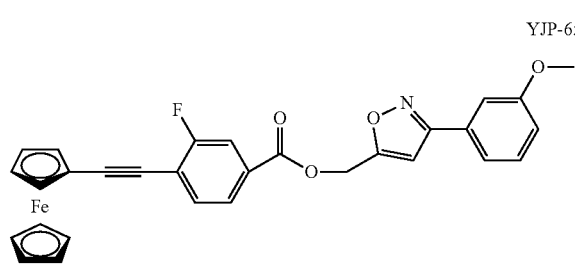
-continued
YJP-66
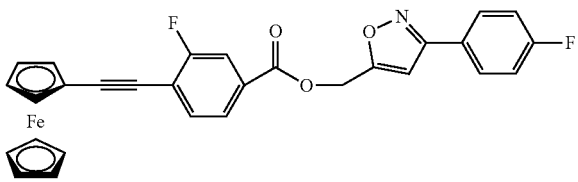
YJP-67
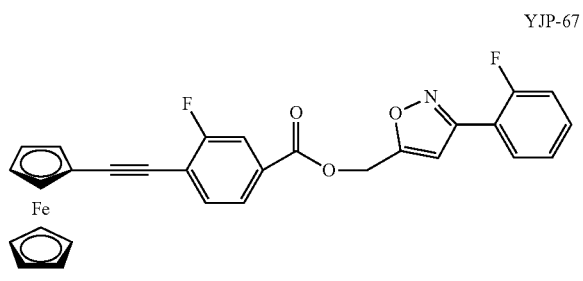
YJP-68
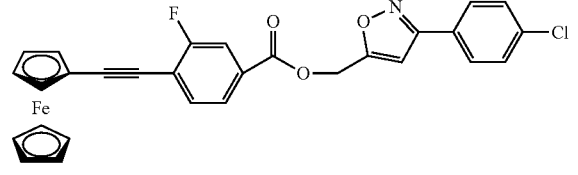
YJP-69
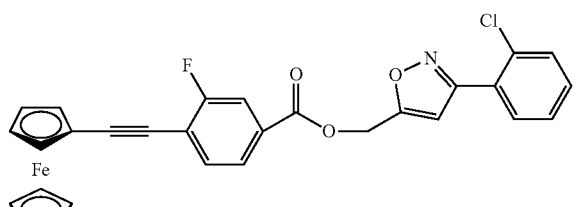
YJP-70
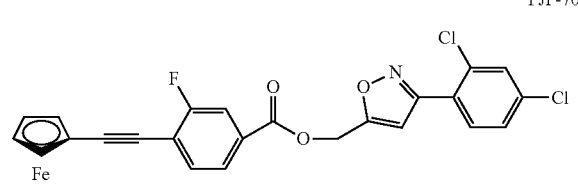
YJP-71
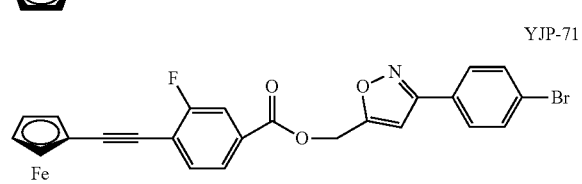
YJP-72
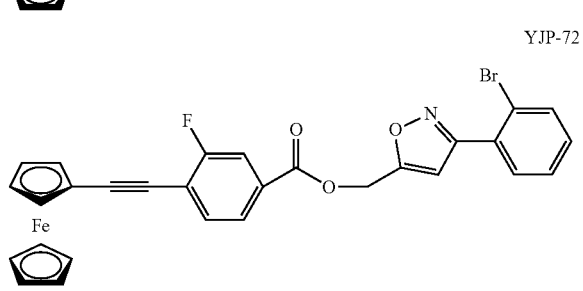

YJP-73
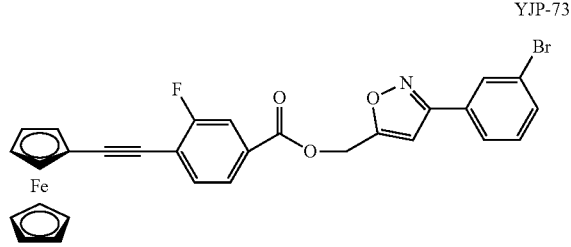
YJP-80
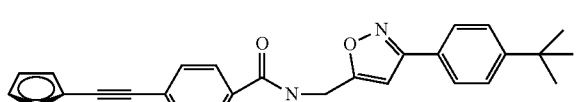
YJP-74
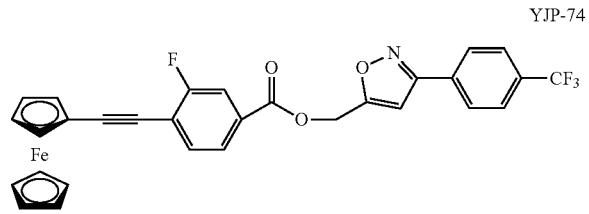
YJP-81
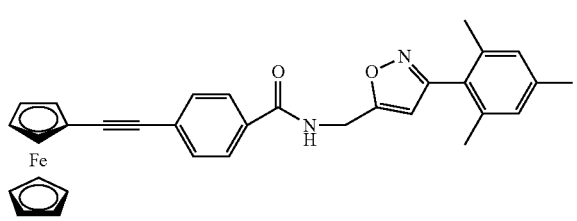
YJP-75
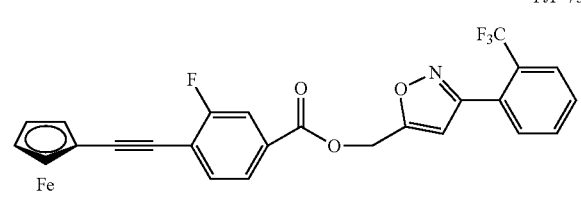
YJP-82
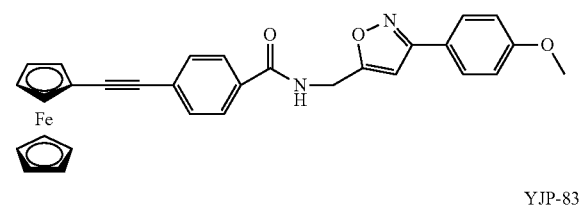
YJP-76
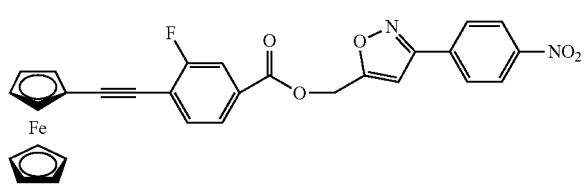
YJP-83
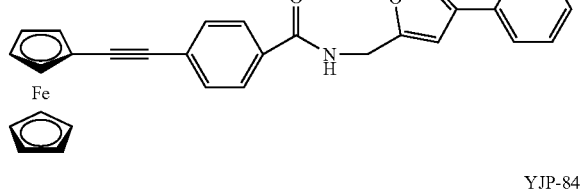
YJP-77
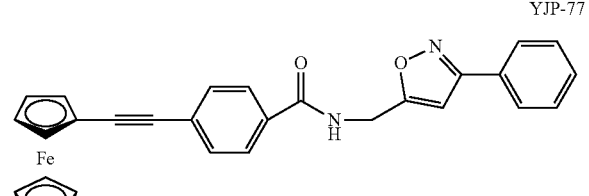
YJP-84
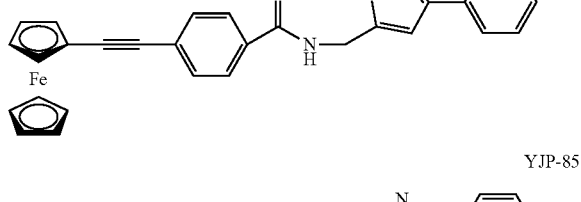
YJP-78
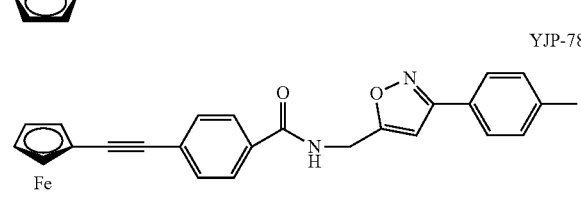
YJP-85
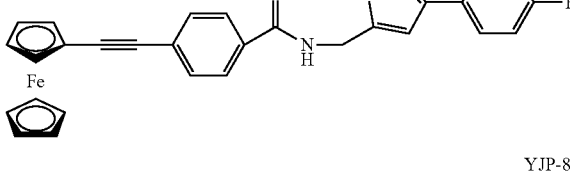
YJP-79
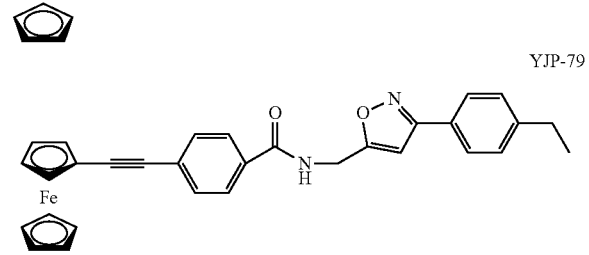
YJP-86
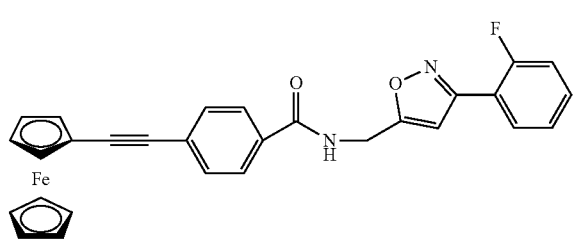

YJP-87
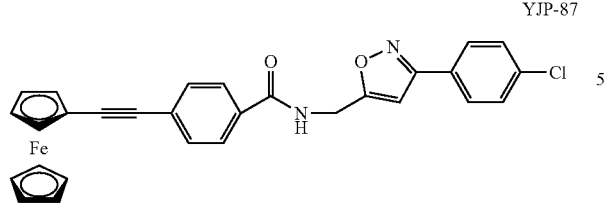
YJP-94
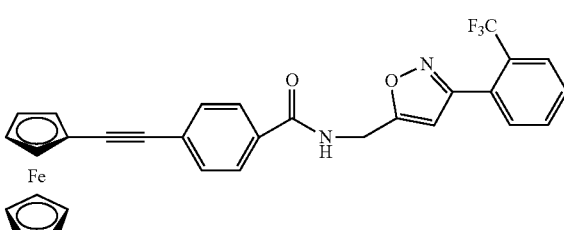
YJP-88
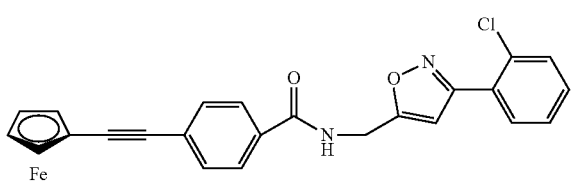
YJP-95
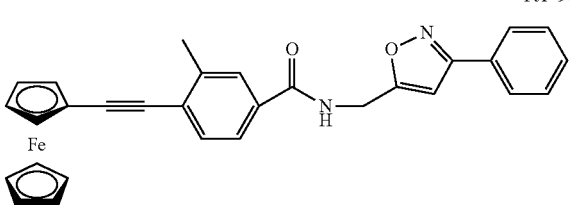
YJP-89
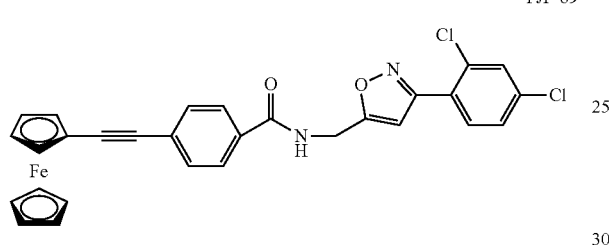
YJP-96
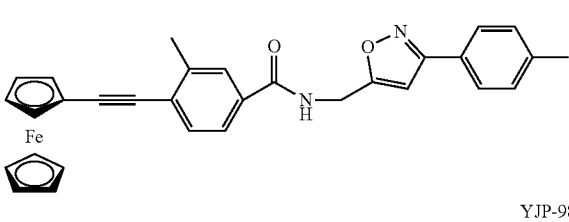
YJP-90
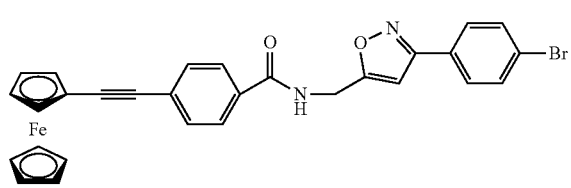
YJP-97
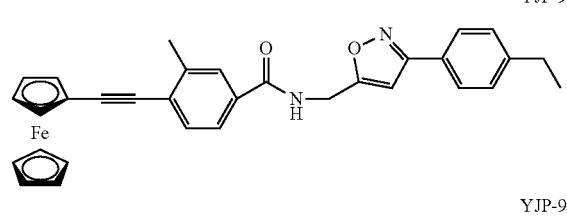
YJP-91
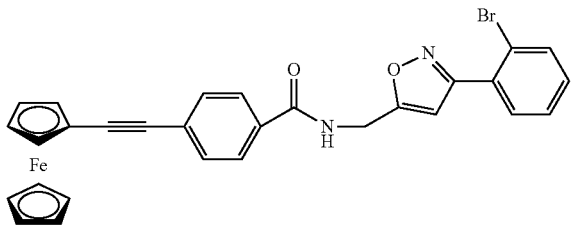
YJP-98
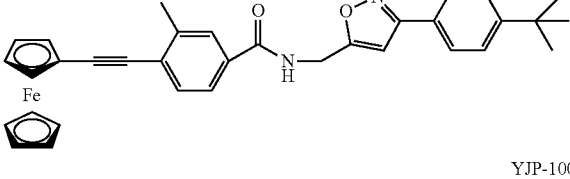
YJP-92
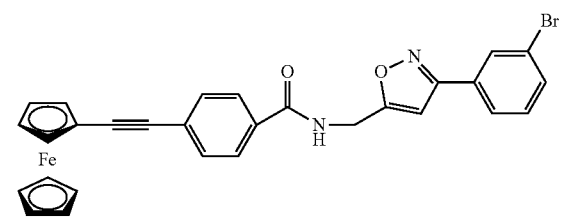
YJP-99
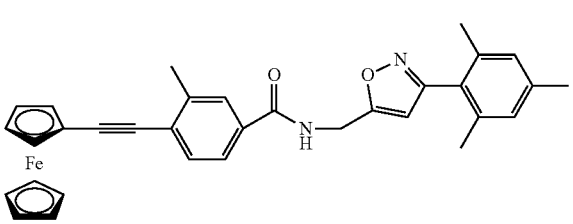
YJP-93
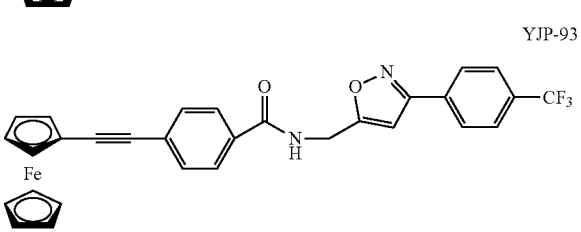
YJP-100

YJP-101
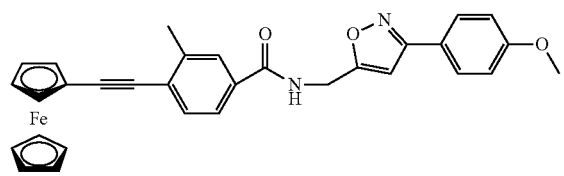
YJP-102
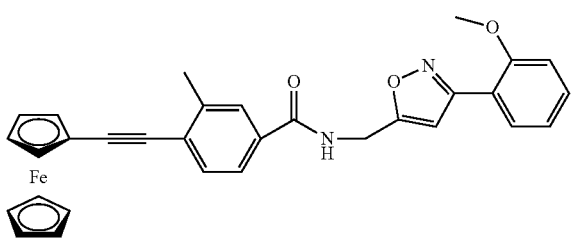
YJP-103
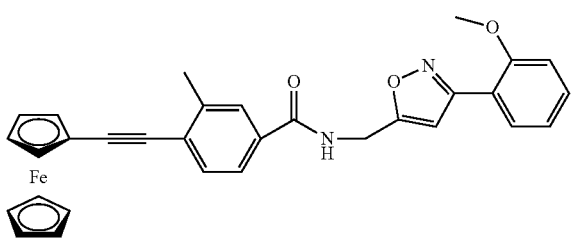
YJP-104
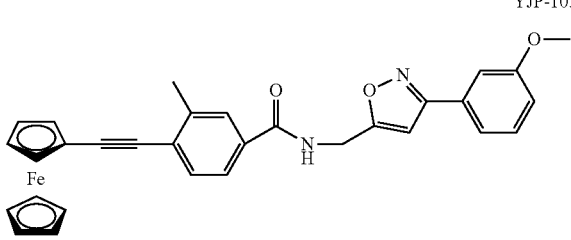
YJP-105
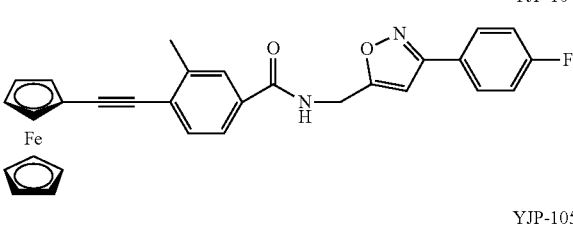
YJP-106
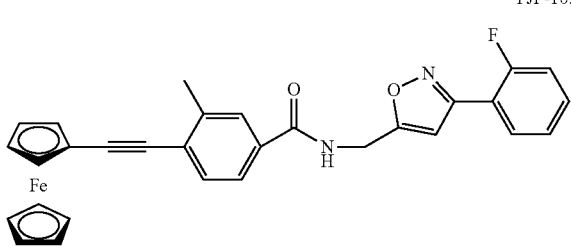
YJP-107
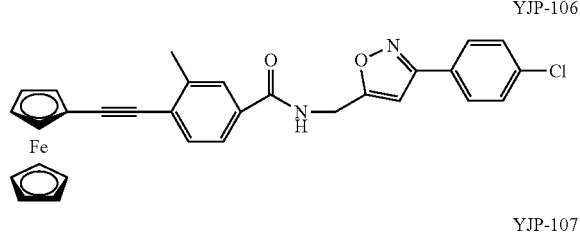
YJP-108
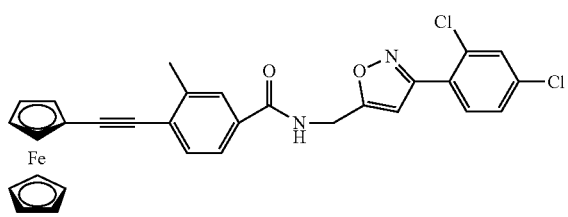
YJP-109
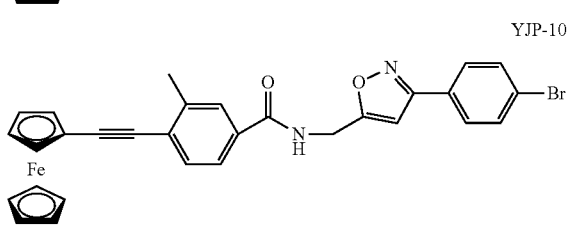
YJP-110
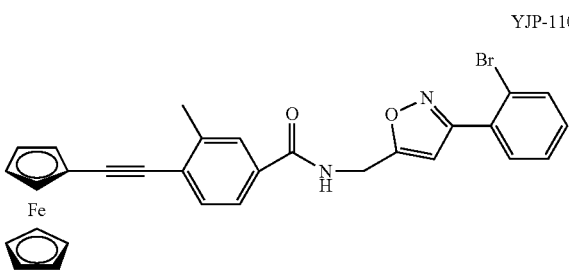
YJP-111
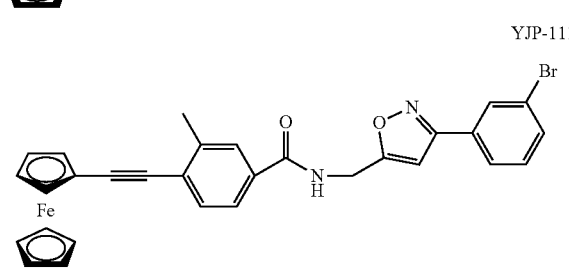
YJP-112
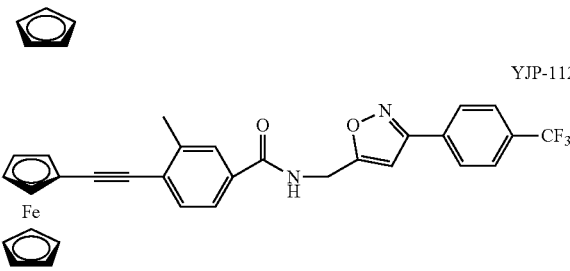
YJP-113
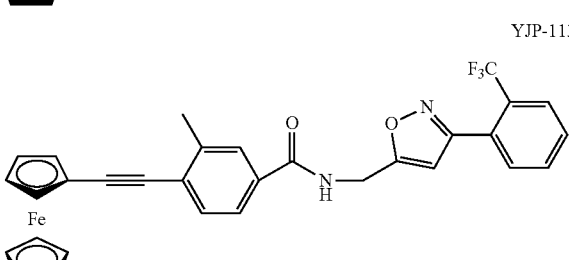
YJP-114
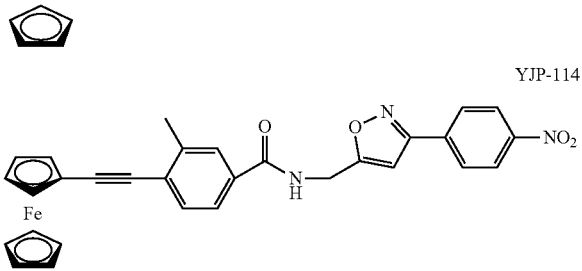

-continued
YJP-115
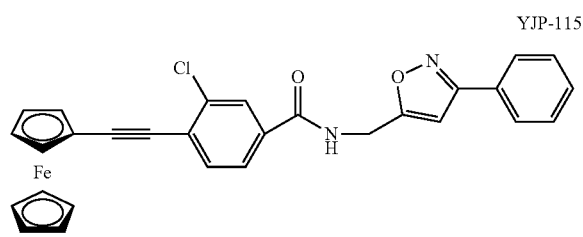
YJP-116
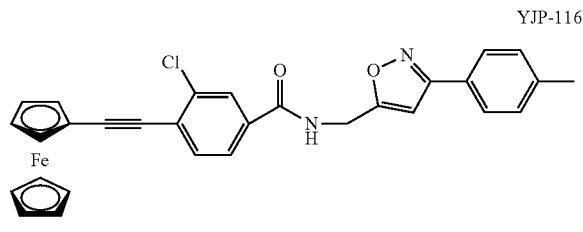
YJP-117
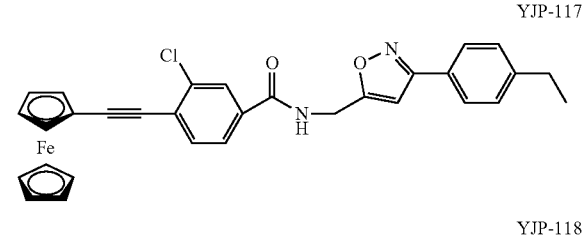
YJP-118
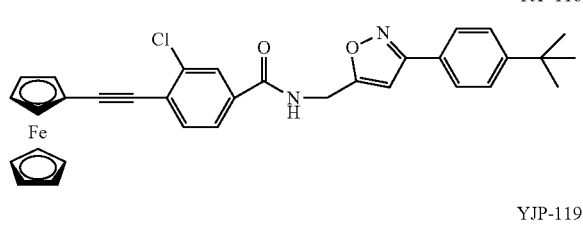
YJP-119
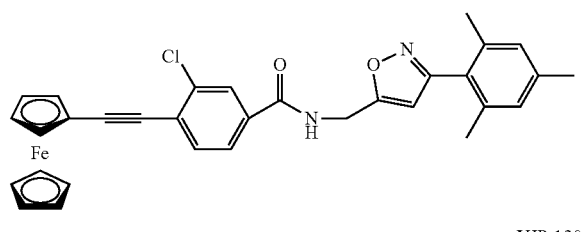
YJP-120
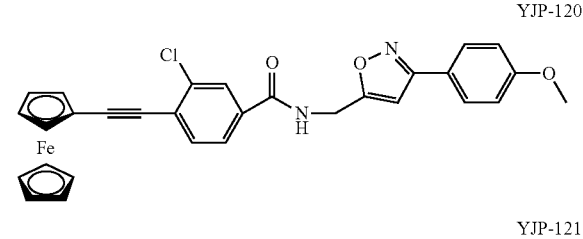
YJP-121
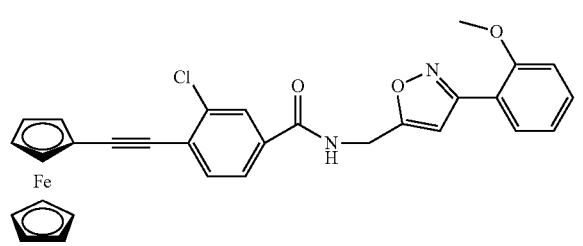
-continued
YJP-122
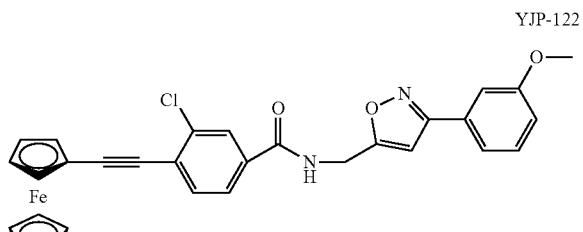
YJP-123
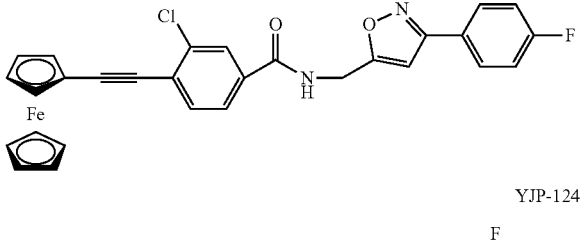
YJP-124
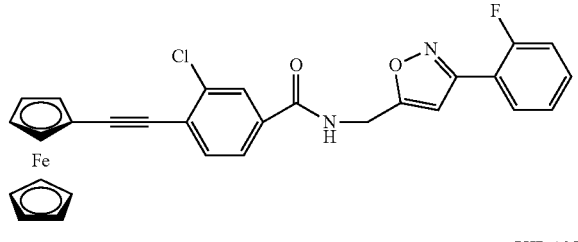
YJP-125
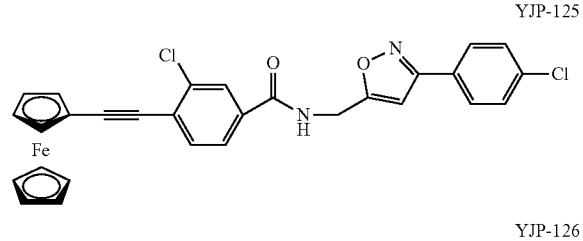
YJP-126
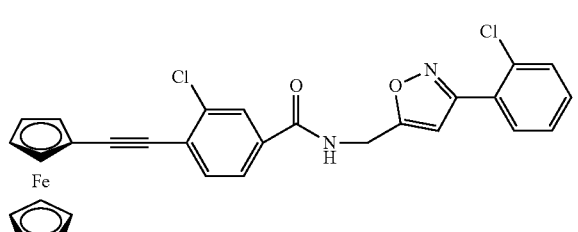
YJP-127
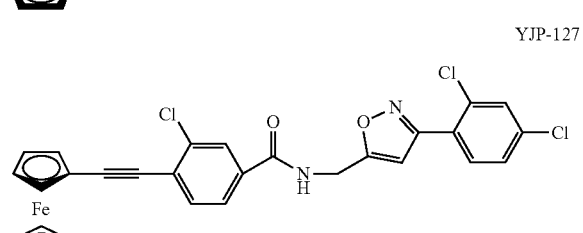
YJP-128
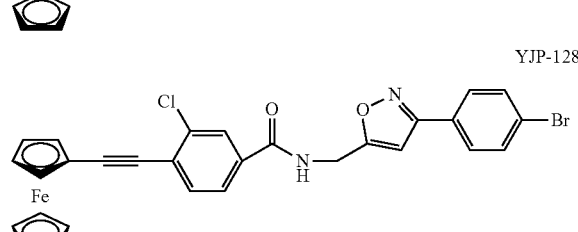

YJP-129
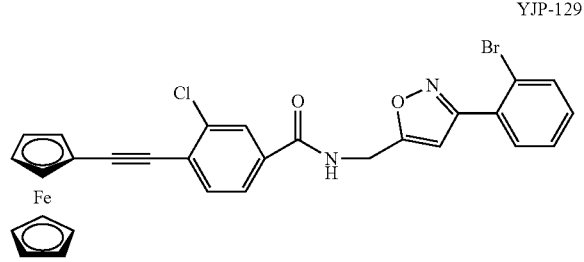
YJP-130
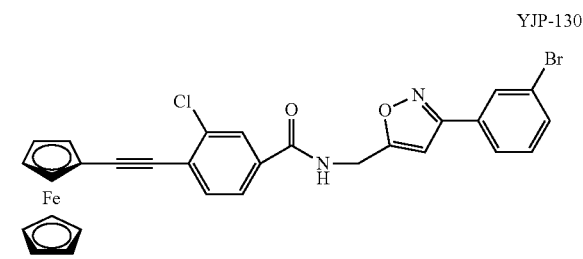
YJP-131
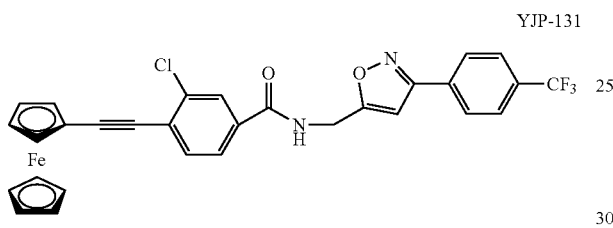
YJP-132
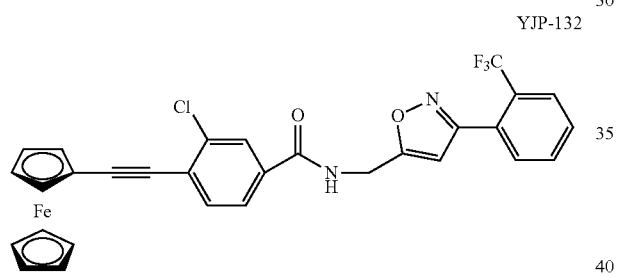
YJP-133
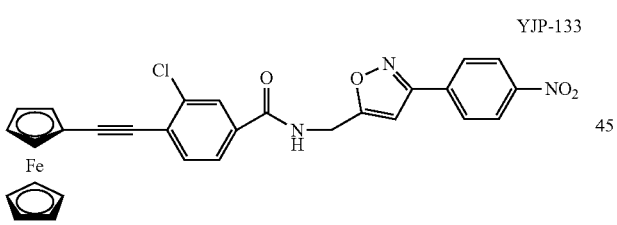
YJP-134
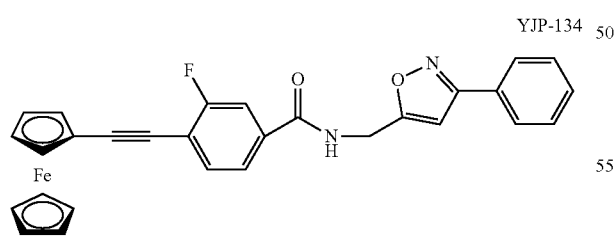
YJP-135
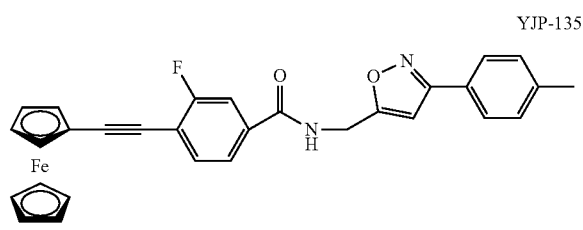
YJP-136
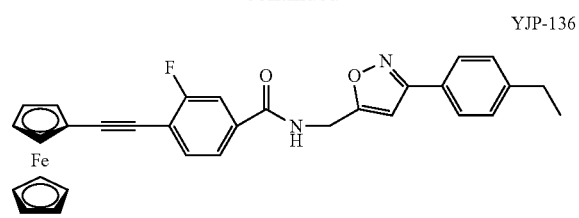
YJP-137
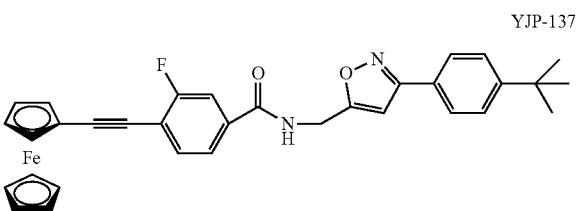
YJP-138
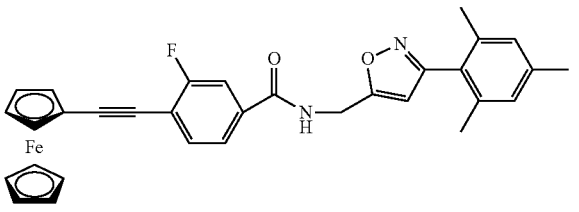
YJP-139
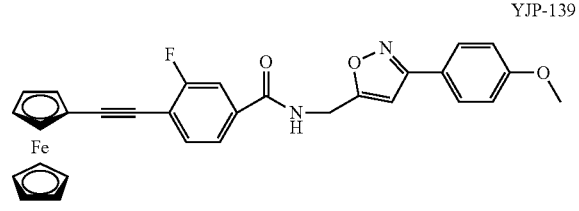
YJP-140
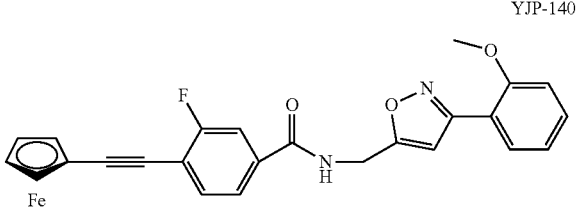
YJP-141
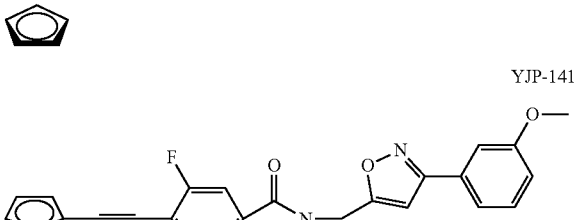
YJP-142
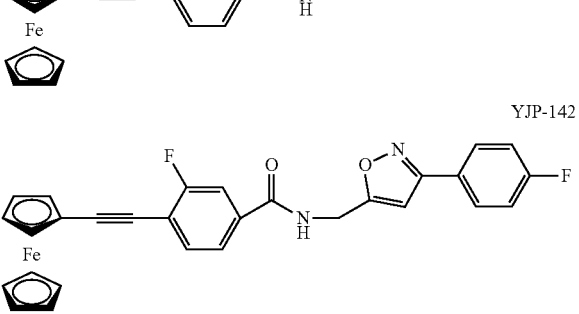

YJP-143
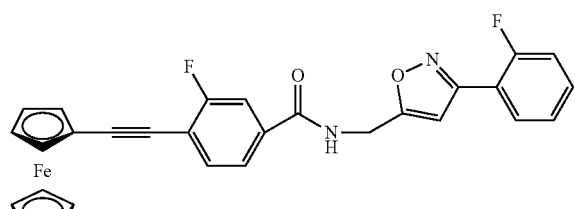
YJP-144
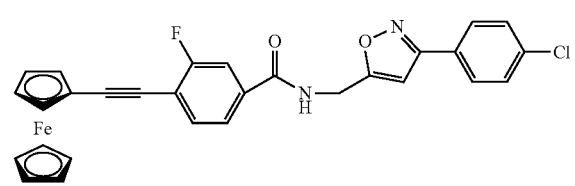
YJP-145
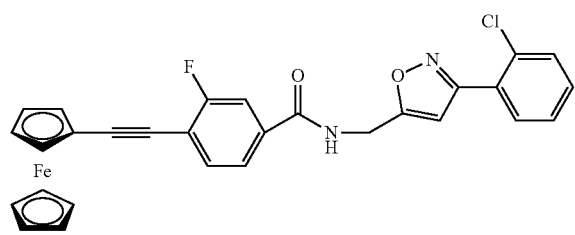
YJP-146
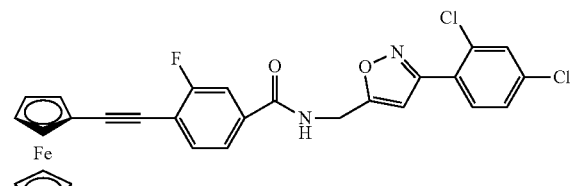
YJP-147
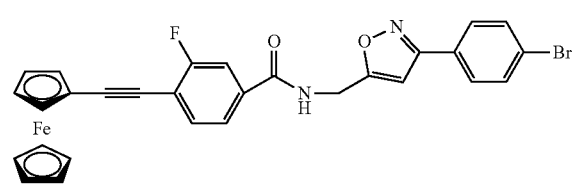
YJP-148
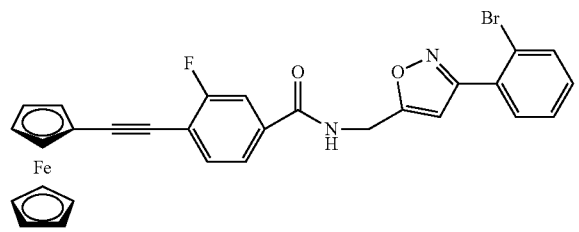
YJP-149
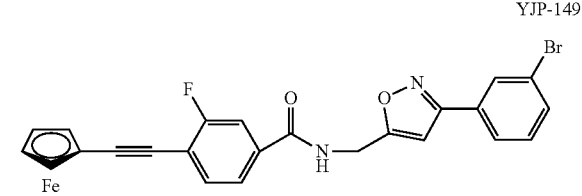
YJP-150
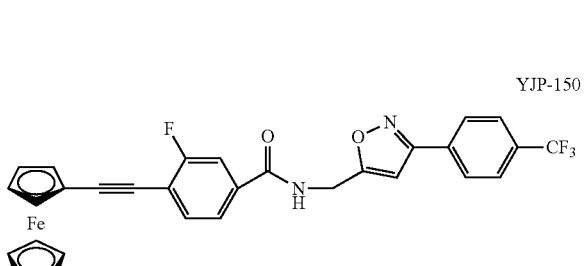
YJP-151
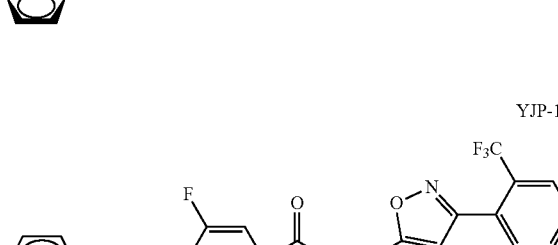
YJP-152
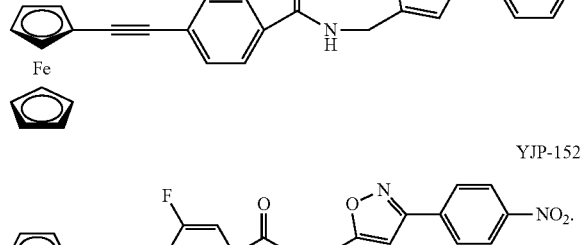
The structures of the compounds YJP-1 to YJP-152 were all characterized by $^1$H NMR analysis. The numbers and NMR data of the compounds YJP-1 to YJP-152 are shown in Table 1:
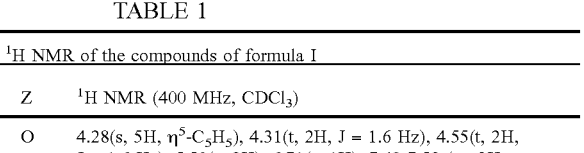
TABLE 1
$^1$H NMR of the compounds of formula I
| No. | R$_1$ | (R$_2$)$_n$ | Z | $^1$H NMR (400 MHz, CDCl$_3$) |
|---|---|---|---|---|
| YJP-1 | H | H | O | 4.28(s, 5H, η$^5$-C$_5$H$_5$), 4.31(t, 2H, J = 1.6 Hz), 4.55(t, 2H, J = 1.6 Hz), 5.50(s, 2H), 6.71(s, 1H), 7.48-7.52 (m, 3H, Ph—H), 7.83-7.85 (m, 2H, Ph—H), 7.59(d, 2H, J = 8.4 Hz), 8.09(d, 2H, J = 8.4 Hz). |

TABLE 1-continued $^1$H NMR of the compounds of formula I

| No. | $R_1$ | $(R_2)_n$ | Z | $^1$H NMR (400 MHz, CDCl$_3$) |
|---|---|---|---|---|
| YJP-2 | H | 4-CH$_3$ | O | 2.43(s, 3H, CH$_3$), 4.28(s, 5H, η$^5$-C5H5), 4.31(t, 2H, J = 1.6 Hz), 4.55(t, 2H, J = 1.6 Hz), 5.50(s, 2H), 6.71(s, 1H), 7.31(d, 2H, J = 6.4 Hz), 7.58(d, 2H, J = 8.4 Hz), 7.74(d, 2H, J = 8.0 Hz), 8.07(d, 2H, J = 8.4 Hz). |
| YJP-3 | H | 4-CH$_2$CH$_3$ | O | 1.30(t, 3H, CH$_3$, J = 7.6 Hz), 2.74(q, 2H, CH$_2$CH$_3$, J = 8.0 Hz), 4.28(s, 5H, η$^5$-C$_5$H$_5$), 4.31(t, 2H, J = 2.0 Hz), 4.55(t, 2H, J = 2.0 Hz), 5.48(s, 2H), 6.71(s, 1H), 7.32(d, 2H, J = 8.0 Hz), 7.58(d, 2H, J = 8.4 Hz), 7.76(d, 2H, J = 8.4 Hz), 8.07(d, 2H, J = 8.0 Hz). |
| YJP-4 | H | 4-C(CH$_3$)$_3$ | O | 1.38(s, 9H, 3CH$_3$), 4.28(s, 5H, η$^5$-C$_5$H$_5$), 4.31(t, 2H, J = 1.6 Hz), 4.55(t, 2H, J = 1.6 Hz), 5.50(s, 2H), 6.71(s, 1H), 7.51(d, 2H, J = 8.4 Hz), 7.58(d, 2H, J = 8.8 Hz), 7.79(d, 2H, J = 8.4 Hz), 8.07(d, 2H, J = 8.4 Hz). |
| YJP-5 | H | 2,4,6-triCH$_3$ | O | 2.18(s, 6H, 2CH$_3$), 2.35(s, 3H, CH$_3$), 4.28(s, 5H, η$^5$-C$_5$H$_5$), 4.31(t, 2H, J = 2.0 Hz), 4.56(t, 2H, J = 2.0 Hz), 5.54(s, 2H), 6.36(s, 1H), 6.97(s, 1H), 7.29(s, 1H), 7.59(d, 2H, J = 8.4 Hz), 8.07(d, 2H, J = 8.4 Hz). |
| YJP-6 | H | 4-OCH$_3$ | O | 3.88(s, 3H, OCH$_3$), 4.28(s, 5H, η$^5$-C$_5$H$_5$), 4.31(t, 2H, J = 2.0 Hz), 4.55(t, 2H, J = 1.6 Hz), 5.48(s, 2H), 6.68(s, 1H), 7.01(d, 2H, J = 7.2 Hz), 7.58(d, 2H, J = 8.4 Hz), 7.79(d, 2H, J = 8.8 Hz), 8.06(d, 2H, J = 8.4 Hz). |
| YJP-7 | H | 2-OCH$_3$ | O | 3.94(s, 3H, OCH$_3$), 4.28(s, 5H, η$^5$-C$_5$H$_5$), 4.31(t, 2H, J = 2.0 Hz), 4.56(t, 2H, J = 2.0 Hz), 5.50(s, 2H), 6.94(s, 1H), 7.02-7.09(m, 2H), 7.43-7.48(m, 1H), 7.57(d, 2H, J = 8.8 Hz), 7.93(dd, 1H, J = 1.6, 2.0 Hz), 8.06 (d, 2H, J = 8.4 Hz). |
| YJP-8 | H | 3-OCH$_3$ | O | 3.89(s, 3H, OCH$_3$), 4.28(s, 5H, η$^5$-C$_5$H$_5$), 4.31(t, 2H, J = 2.0 Hz), 4.55(t, 2H, J = 2.0 Hz), 5.51(s, 2H), 6.72(s, 1H), 7.01-7.04(m, 1H), 7.39-7.41(m, 1H), 7.58(d, 2H, J = 8.4 Hz), 8.06(d, 2H, J = 8.4 Hz). |
| YJP-9 | H | 4-F | O | 4.27(s, 5H, η$^5$-C$_5$H$_5$), 4.31(t, 2H, J = 2.0 Hz), 4.55(t, 2H, J = 2.0 Hz), 5.51(s, 2H), 6.70(s, 1H), 7.18(d, 2H, J = 8.4 Hz), 7.58(d, 2H, J = 8.8 Hz), 7.82(d, 2H, J = 8.8 Hz), 8.06(d, 2H, J = 8.4 Hz). |
| YJP-10 | H | 2-F | O | 4.28(s, 5H, η$^5$-C$_5$H$_5$), 4.31(t, 2H, J = 2.0 Hz), 4.56(t, 2H, J = 2.0 Hz), 5.52(s, 2H), 6.87(s, 1H), 7.20-7.29(m, 3H), 7.44-7.49(m, 1H), 7.58(d, 2H, J = 8.8 Hz), 8.06(d, 2H, J = 8.8 Hz). |
| YJP-11 | H | 4-Cl | O | 4.28(s, 5H, η$^5$-C$_5$H$_5$), 4.31(t, 2H, J = 1.6 Hz), 4.56(t, 2H, J = 2.0 Hz), 5.51(s, 2H), 6.71(s, 1H), 7.47(d, 2H, J = 8.4 Hz), 7.58(d, 2H, J = 8.4 Hz), 7.79(d, 2H, J = 8.4 Hz), 8.06(d, 2H, J = 8.4 Hz). |
| YJP-12 | H | 2-Cl | O | 4.28(s, 5H, η$^5$-C$_5$H$_5$), 4.31(t, 2H, J = 2.0 Hz), 4.55(t, 2H, J = 2.0 Hz), 5.53(s, 2H), 6.90(s, 1H), 7.37-7.45(m, 2H), 7.53(dd, 1H, J = 1.2, 1.6 Hz), 7.58(d, 2H, J = 8.8 Hz), 7.76-7.79(m, 1H), 8.07(d, 2H, J = 8.4 Hz). |
| YJP-13 | H | 2,4-diCl | O | 4.28(s, 5H, η$^5$-C$_5$H$_5$), 4.31(t, 2H, J = 2.0 Hz), 4.55(t, 2H, J = 2.0 Hz), 5.52(s, 2H), 6.90(s, 1H), 7.38(dd, 1H, J = 2.0, 2.0 Hz), 7.55(d, 1H, J = 2.0 Hz), 7.58(d, 2H, J = 8.4 Hz), 7.74(d, 1H, J = 8.4 Hz), 8.07(d, 2H, J = 8.4 Hz). |
| YJP-14 | H | 4-Br | O | 4.28(s, 5H, η$^5$-C$_5$H$_5$), 4.31(t, 2H, J = 1.6 Hz), 4.56(t, 2H, J = 2.0 Hz), 5.51(s, 2H), 6.71(s, 1H), 7.47(d, 2H, J = 8.4 Hz), 7.58(d, 2H, J = 8.4 Hz), 7.79(d, 2H, J = 8.4 Hz), 8.06(d, 2H, J = 8.4 Hz). |
| YJP-15 | H | 2-Br | O | 4.28(s, 5H, η$^5$-C$_5$H$_5$), 4.31(t, 2H, J = 2.0 Hz), 4.56(t, 2H, J = 2.0 Hz), 5.52(s, 2H), 6.86(s, 1H), 7.21(ddd, 1H, J = 0.8, 0.8, 1.2 Hz), 7.24(dd, 1H, J = 0.8, 1.2 Hz), 7.29(dd, 1H, J = 0.8, 1.2 Hz), 7.44-7.48(m, 1H), 7.55(d, 2H, J = 8.8 Hz), 8.07(d, 2H, J = 8.4 Hz). |
| YJP-16 | H | 3-Br | O | 4.28(s, 5H, η$^5$-C$_5$H$_5$), 4.31(t, 2H, J = 2.0 Hz), 4.55(t, 2H, J = 1.6 Hz), 5.53(s, 2H), 6.64(s, 1H), 7.69(d, 2H, J = 8.4 Hz), 7.63-7.68(m, 3H), 7.85(d, 1H, J = 7.6 Hz), 8.07(d, 2H, J = 8.4 Hz). |
| YJP-17 | H | 4-CF$_3$ | O | 4.28(s, 5H, η$^5$-C$_5$H$_5$), 4.31(t, 2H, J = 1.6 Hz), 4.55(t, 2H, J = 1.6 Hz), 5.52(s, 2H), 6.78(s, 1H), 7.58(d, 2H, J = 8.4 Hz), 7.76(d, 2H, J = 8.0 Hz), 7.98(d, 2H, J = 8.4 Hz), 8.06(d, 2H, J = 8.4 Hz). |
| YJP-18 | H | 2-CF$_3$ | O | 4.28(s, 5H, η$^5$-C$_5$H$_5$), 4.31(t, 2H, J = 2.0 Hz), 4.55(t, 2H, J = 2.0 Hz), 5.53(s, 2H), 6.64(s, 1H), 7.69(d, 2H, J = 8.4 Hz), 7.63-7.68(m, 3H), 7.85(d, 1H, J = 7.6 Hz), 8.07(d, 2H, J = 8.4 Hz). |
| YJP-19 | H | 4-NO$_2$ | O | 4.28(s, 5H, η$^5$-C$_5$H$_5$), 4.31(t, 2H, J = 2.0 Hz), 4.55(t, 2H, J = 2.0 Hz), 5.53(s, 2H), 6.81(s, 1H), 7.45(d, 2H, J = 8.4 Hz), 7.58(d, 2H, J = 8.4 Hz), 8.06(d, 2H, J = 8.4 Hz), 8.36(d, 2H, J = 8.4 Hz). |

TABLE 1-continued

¹H NMR of the compounds of formula I

| No. | R₁ | (R₂)ₙ | Z | ¹H NMR (400 MHz, CDCl₃) |
|---|---|---|---|---|
| YJP-20 | 3'-CH₃ | H | O | 2.49(s, 3H, CH₃), 4.28(s, 5H, η⁵-C₅H₅), 4.31(t, 2H, J = 1.6 Hz), 4.55(t, 2H, J = 1.6 Hz), 5.50(s, 2H), 6.71(s, 1H), 7.48-7.52 (m, 3H, Ph—H), 7.58(d, 1H, J = 6.5 Hz), 7.72(s, 1H), 7.82(d, 1H, J = 5.8 Hz), 7.83-7.85 (m, 2H, Ph—H). |
| YJP-21 | 3'-CH₃ | 4-CH₃ | O | 2.43(s, 3H, CH₃), 2.49(s, 3H, CH₃), 4.28(s, 5H, η⁵-C₅H₅), 4.31(t, 2H, J = 1.6 Hz), 4.55(t, 2H, J = 1.6 Hz), 5.50(s, 2H), 6.71(s, 1H), 7.31(d, 2H, J = 6.4 Hz), 7.58(d, 1H, J = 6.5 Hz), 7.72(s, 1H), 7.82(d, 1H, J = 5.8 Hz), 7.82(d, 1H, J = 5.8 Hz). |
| YJP-22 | 3'-CH₃ | 4-CH₂CH₃ | O | 1.30(t, 3H, CH₃, J = 7.6 Hz), 2.49(s, 3H, CH₃), 2.74(q, 2H, CH₂CH₃, J = 8.0 Hz), 4.28(s, 5H, η⁵-C₅H₅), 4.31(t, 2H, J = 2.0 Hz), 4.55(t, 2H, J = 2.0 Hz), 5.48(s, 2H), 6.71(s, 1H), 7.32(d, 2H, J = 8.0 Hz), 7.58(d, 1H, J = 6.5 Hz), 7.72(s, 1H), 7.82(d, 1H, J = 5.8 Hz), 7.76(d, 2H, J = 8.4 Hz). |
| YJP-23 | 3'-CH₃ | 4-C(CH₃)₃ | O | 1.38(s, 9H, 3CH₃), 2.49(s, 3H, CH₃), 4.28(s, 5H, η⁵-C₅H₅), 4.31(t, 2H, J = 1.6 Hz), 4.55(t, 2H, J = 1.6 Hz), 5.50(s, 2H), 6.71(s, 1H), 7.51(d, 2H, J = 8.4 Hz), 7.58(d, 1H, J = 6.5 Hz), 7.72(s, 1H), 7.82(d, 1H, J = 5.8 Hz), 7.79(d, 2H, J = 8.4 Hz). |
| YJP-24 | 3'-CH₃ | 2,4,6-TriCH₃ | O | 2.18(s, 6H, 2CH₃), 2.35(s, 3H, CH₃), 2.49(s, 3H, CH₃), 4.28(s, 5H, η⁵-C₅H₅), 4.31(t, 2H, J = 2.0 Hz), 4.56(t, 2H, J = 2.0 Hz), 5.54(s, 2H), 6.36(s, 1H), 6.97(s, 1H), 7.29(s, 1H), 7.58(d, 1H, J = 6.5 Hz), 7.72(s, 1H), 7.82(d, 1H, J = 5.8 Hz). |
| YJP-25 | 3'-CH₃ | 4-OCH₃ | O | 2.49(s, 3H, CH₃), 3.88(s, 3H, OCH₃), 4.28(s, 5H, η⁵-C₅H₅), 4.31(t, 2H, J = 2.0 Hz), 4.55(t, 2H, J = 1.6 Hz), 5.48(s, 2H), 6.68(s, 1H), 7.01(d, 2H, J = 7.2 Hz), 7.58(d, 1H, J = 6.5 Hz), 7.72(s, 1H), 7.79(d, 2H, J = 8.8 Hz), 7.82(d, 1H, J = 5.8 Hz). |
| YJP-26 | 3'-CH₃ | 2-OCH₃ | O | 2.49(s, 3H, CH₃), 3.94(s, 3H, OCH₃), 4.28(s, 5H, η⁵-C₅H₅), 4.31(t, 2H, J = 2.0 Hz), 4.56(t, 2H, J = 2.0 Hz), 5.50(s, 2H), 6.94(s, 1H), 7.02-7.09(m, 2H), 7.43-7.48(m, 1H), 7.58(d, 1H, J = 6.5 Hz), 7.72(s, 1H), 7.82(d, 1H, J = 5.8 Hz), 7.93(dd, 1H, J = 1.6, 2.0 Hz). |
| YJP-27 | 3'-CH₃ | 3-OCH₃ | O | 2.49(s, 3H, CH₃), 3.89(s, 3H, OCH₃), 4.28(s, 5H, η⁵-C₅H₅), 4.31(t, 2H, J = 2.0 Hz), 4.55(t, 2H, J = 2.0 Hz), 5.51(s, 2H), 6.72(s, 1H), 7.01-7.04(m, 1H), 7.39-7.41(m, 1H), 7.58(d, 1H, J = 6.5 Hz), 7.72(s, 1H), 7.82(d, 1H, J = 5.8 Hz). |
| YJP-28 | 3'-CH₃ | 4-F | O | 2.49(s, 3H, CH₃), 4.27(s, 5H, η⁵-C₅H₅), 4.31(t, 2H, J = 2.0 Hz), 4.55(t, 2H, J = 2.0 Hz), 5.51(s, 2H), 6.70(s, 1H), 7.18(d, 2H, J = 8.4 Hz), 7.58(d, 1H, J = 6.5 Hz), 7.72(s, 1H), 7.82(d, 1H, J = 5.8 Hz), 7.83(d, 2H, J = 8.8 Hz). |
| YJP-29 | 3'-CH₃ | 2-F | O | 2.49(s, 3H, CH₃), 4.28(s, 5H, η⁵-C₅H₅), 4.31(t, 2H, J = 2.0 Hz), 4.56(t, 2H, J = 2.0 Hz), 5.52(s, 2H), 6.87(s, 1H), 7.20-7.29(m, 3H), 7.44-7.49(m, 1H), 7.58(d, 1H, J = 6.5 Hz), 7.72(s, 1H), 7.82(d, 1H, J = 5.8 Hz). |
| YJP-30 | 3'-CH₃ | 4-Cl | O | 2.49(s, 3H, CH₃), 4.28(s, 5H, η⁵-C₅H₅), 4.31(t, 2H, J = 1.6 Hz), 4.56(t, 2H, J = 2.0 Hz), 5.51(s, 2H), 6.71(s, 1H), 7.47(d, 2H, J = 8.4 Hz), 7.58(d, 1H, J = 6.5 Hz), 7.72(s, 1H), 7.79(d, 2H, J = 8.4 Hz), 7.82(d, 1H, J = 5.8 Hz). |
| YJP-31 | 3'-CH₃ | 2-Cl | O | 2.49(s, 3H, CH₃), 4.28(s, 5H, η⁵-C₅H₅), 4.31(t, 2H, J = 2.0 Hz), 4.55(t, 2H, J = 2.0 Hz), 5.53(s, 2H), 6.90(s, 1H), 7.37-7.45(m, 2H), 7.53(dd, 1H, J = 1.2, 1.6 Hz), 7.58(d, 1H, J = 6.5 Hz), 7.72(s, 1H), 7.76-7.79(m, 1H), 7.82(d, 1H, J = 5.8 Hz). |
| YJP-32 | 3'-CH₃ | 2,4-diCl | O | 2.49(s, 3H, CH₃), 4.28(s, 5H, η⁵-C₅H₅), 4.31(t, 2H, J = 2.0 Hz), 4.55(t, 2H, J = 2.0 Hz), 5.52(s, 2H), 6.90(s, 1H), 7.38(dd, 1H, J = 2.0, 2.0 Hz), 7.55(d, 1H, J = 2.0 Hz), 7.58(d, 1H, J = 6.5 Hz), 7.72(s, 1H), 7.74(d, 1H, J = 8.4 Hz), 7.82(d, 1H, J = 5.8 Hz). |
| YJP-33 | 3'-CH₃ | 4-Br | O | 2.49(s, 3H, CH₃), 4.28(s, 5H, η⁵-C₅H₅), 4.31(t, 2H, J = 1.6 Hz), 4.56(t, 2H, J = 2.0 Hz), 5.51(s, 2H), 6.71(s, 1H), 7.47(d, 2H, J = 8.4 Hz), 7.58(d, 1H, J = 6.5 Hz), 7.72(s, 1H), 7.79(d, 2H, J = 8.4 Hz), 7.82(d, 1H, J = 5.8 Hz). |
| YJP-34 | 3'-CH₃ | 2-Br | O | 2.49(s, 3H, CH₃), 4.28(s, 5H, η⁵-C₅H₅), 4.31(t, 2H, J = 2.0 Hz), 4.56(t, 2H, J = 2.0 Hz), 5.52(s, 2H), 6.86(s, 1H), 7.21(ddd, 1H, J = 0.8, 0.8, 1.2 Hz), 7.24(dd, 1H, J = 0.8, 1.2 Hz), 7.29(dd, 1H, J = 0.8, 1.2 Hz), 7.44-7.48(m, 1H), 7.58(d, 1H, J = 6.5 Hz), 7.72(s, 1H), 7.82(d, 1H, J = 5.8 Hz). |

TABLE 1-continued

¹H NMR of the compounds of formula I

| No. | $R_1$ | $(R_2)_n$ | Z | ¹H NMR (400 MHz, CDCl₃) |
|---|---|---|---|---|
| YJP-35 | 3'-CH₃ | 3-Br | O | 2.49(s, 3H, CH₃), 4.28(s, 5H, $\eta^5$-C₅H₅), 4.31(t, 2H, J = 2.0 Hz), 4.55(t, 2H, J = 1.6 Hz), 5.53(s, 2H), 6.64(s, 1H), 7.58(d, 1H, J = 6.5 Hz), 7.63-7.68(m, 3H), 7.72(s, 1H), 7.82(d, 1H, J = 5.8 Hz), 7.85(d, 1H, J = 7.6 Hz). |
| YJP-36 | 3'-CH₃ | 4-CF₃ | O | 2.49(s, 3H, CH₃), 4.28(s, 5H, $\eta^5$-C₅H₅), 4.31(t, 2H, J = 1.6 Hz), 4.55(t, 2H, J = 1.6 Hz), 5.52(s, 2H), 6.78(s, 1H), 7.58(d, 1H, J = 6.5 Hz), 7.72(s, 1H), 7.76(d, 2H, J = 8.0 Hz), 7.85(d, 1H, J = 7.6 Hz), 7.98(d, 2H, J = 8.4 Hz). |
| YJP-37 | 3'-CH₃ | 2-CF₃ | O | 2.49(s, 3H, CH₃), 4.28(s, 5H, $\eta^5$-C₅H₅), 4.31(t, 2H, J = 2.0 Hz), 4.55(t, 2H, J = 1.6 Hz), 5.53(s, 2H), 6.64(s, 1H), 7.58(d, 1H, J = 6.5 Hz), 7.63-7.68(m, 3H), 7.72(s, 1H), 7.82(d, 1H, J = 5.8 Hz), 7.85(d, 1H, J = 7.6 Hz). |
| YJP-38 | 3'-CH₃ | 4-NO₂ | O | 2.49(s, 3H, CH₃), 4.28(s, 5H, $\eta^5$-C₅H₅), 4.31(t, 2H, J = 2.0 Hz), 4.55(t, 2H, J = 2.0 Hz), 5.53(s, 2H), 6.81(s, 1H), 7.45(d, 2H, J = 8.4 Hz), 7.58(d, 1H, J = 6.5 Hz), 7.72(s, 1H), 7.82(d, 1H, J = 5.8 Hz), 8.36(d, 2H, J = 8.4 Hz). |
| YJP-39 | 3'-Cl | H | O | 4.28(s, 5H, $\eta^5$-C₅H₅), 4.31(t, 2H, J = 1.6 Hz), 4.55(t, 2H, J = 1.6 Hz), 5.50(s, 2H), 6.71(s, 1H), 7.48-7.52 (m, 3H, Ph—H), 7.59(s, 1H), 7.68(d, 1H, J = 5.6 Hz), 7.78(d, 1H, J = 5.8 Hz), 7.83-7.85 (m, 2H, Ph—H). |
| YJP-40 | 3'-Cl | 4-CH₃ | O | 2.43(s, 3H, CH₃), 4.28(s, 5H, $\eta^5$-C₅H₅), 4.31(t, 2H, J = 1.6 Hz), 4.55(t, 2H, J = 1.6 Hz), 5.50(s, 2H), 6.71(s, 1H), 7.31(d, 2H, J = 6.4 Hz), 7.59(s, 1H), 7.68(d, 1H, J = 5.6 Hz), 7.74(d, 2H, J = 8.0 Hz), 7.78(d, 1H, J = 5.8 Hz). |
| YJP-41 | 3'-Cl | 4-CH₂CH₃ | O | 1.30(t, 3H, CH₃, J = 7.6 Hz), 2.74(q, 2H, CH₂CH₃, J = 8.0 Hz), 4.28(s, 5H, $\eta^5$-C₅H₅), 4.31(t, 2H, J = 2.0 Hz), 4.55(t, 2H, J = 2.0 Hz), 5.48(s, 2H), 6.71(s, 1H), 7.32(d, 2H, J = 8.0 Hz), 7.59(s, 1H), 7.68(d, 1H, J = 5.6 Hz), 7.76(d, 2H, J = 8.4 Hz), 7.78(d, 1H, J = 5.8 Hz). |
| YJP-42 | 3'-Cl | 4-C(CH₃)₃ | O | 1.38(s, 9H, 3CH₃), 4.28(s, 5H, $\eta^5$-C₅H₅), 4.31(t, 2H, J = 1.6 Hz), 4.55(t, 2H, J = 1.6 Hz), 5.50(s, 2H), 6.71(s, 1H), 7.51(d, 2H, J = 8.4 Hz), 7.59(s, 1H), 7.68(d, 1H, J = 5.6 Hz), 7.78(d, 1H, J = 5.8 Hz), 7.81(d, 2H, J = 8.4 Hz). |
| YJP-43 | 3'-Cl | 2,4,6-TriCH₃ | O | 2.18(s, 6H, 2CH₃), 2.35(s, 3H, CH₃), 4.28(s, 5H, $\eta^5$-C₅H₅), 4.31(t, 2H, J = 2.0 Hz), 4.56(t, 2H, J = 2.0 Hz), 5.54(s, 2H), 6.36(s, 1H), 6.97(s, 1H), 7.29(s, 1H), 7.59(s, 1H), 7.68(d, 1H, J = 5.6 Hz), 7.78(d, 1H, J = 5.8 Hz). |
| YJP-44 | 3'-Cl | 4-OCH₃ | O | 3.88(s, 3H, OCH₃), 4.28(s, 5H, $\eta^5$-C₅H₅), 4.31(t, 2H, J = 2.0 Hz), 4.55(t, 2H, J = 1.6 Hz), 5.48(s, 2H), 6.68(s, 1H), 7.01(d, 2H, J = 7.2 Hz), 7.59(s, 1H), 7.68(d, 1H, J = 5.6 Hz), 7.78(d, 1H, J = 5.8 Hz), 7.81(d, 2H, J = 8.8 Hz). |
| YJP-45 | 3'-Cl | 2-OCH₃ | O | 3.94(s, 3H, OCH₃), 4.28(s, 5H, $\eta^5$-C₅H₅), 4.31(t, 2H, J = 2.0 Hz), 4.56(t, 2H, J = 2.0 Hz), 5.50(s, 2H), 6.94(s, 1H), 7.02-7.09(m, 2H), 7.43-7.48(m, 1H), 7.59(s, 1H), 7.68(d, 1H, J = 5.6 Hz), 7.78(d, 1H, J = 5.8 Hz), 7.93(dd, 1H, J = 1.6, 2.0 Hz). |
| YJP-46 | 3'-Cl | 3-OCH₃ | O | 3.89(s, 3H, OCH₃), 4.28(s, 5H, $\eta^5$-C₅H₅), 4.31(t, 2H, J = 2.0 Hz), 4.55(t, 2H, J = 2.0 Hz), 5.51(s, 2H), 6.72(s, 1H), 7.01-7.04(m, 1H), 7.39-7.41(m, 1H), 7.59(s, 1H), 7.68(d, 1H, J = 5.6 Hz), 7.78(d, 1H, J = 5.8 Hz). |
| YJP-47 | 3'-Cl | 4-F | O | 4.27(s, 5H, $\eta^5$-C₅H₅), 4.31(t, 2H, J = 2.0 Hz), 4.55(t, 2H, J = 2.0 Hz), 5.51(s, 2H), 6.70(s, 1H), 7.18(d, 2H, J = 8.4 Hz), 7.59(s, 1H), 7.68(d, 1H, J = 5.6 Hz), 7.78(d, 1H, J = 5.8 Hz), 7.82(d, 2H, J = 8.8 Hz). |
| YJP-48 | 3'-Cl | 2-F | O | 4.28(s, 5H, $\eta^5$-C₅H₅), 4.31(t, 2H, J = 2.0 Hz), 4.56(t, 2H, J = 2.0 Hz), 5.52(s, 2H), 6.87(s, 1H), 7.20-7.29(m, 3H), 7.44-7.49(m, 1H), 7.59(s, 1H), 7.68(d, 1H, J = 5.6 Hz), 7.78(d, 1H, J = 5.8 Hz). |
| YJP-49 | 3'-Cl | 4-Cl | O | 4.28(s, 5H, $\eta^5$-C₅H₅), 4.31(t, 2H, J = 1.6 Hz), 4.56(t, 2H, J = 2.0 Hz), 5.51(s, 2H), 6.71(s, 1H), 7.47(d, 2H, J = 8.4 Hz), 7.59(s, 1H), 7.68(d, 1H, J = 5.6 Hz), 7.78(d, 1H, J = 5.8 Hz), 7.82(d, 2H, J = 8.4 Hz). |
| YJP-50 | 3'-Cl | 2-Cl | O | 4.28(s, 5H, $\eta^5$-C₅H₅), 4.31(t, 2H, J = 2.0 Hz), 4.55(t, 2H, J = 2.0 Hz), 5.53(s, 2H), 6.90(s, 1H), 7.37-7.45(m, 2H), 7.53(dd, 1H, J = 1.2, 1.6 Hz), 7.59(s, 1H), 7.68(d, 1H, J = 5.6 Hz), 7.78(d, 1H, J = 5.8 Hz), 7.79-7.81(m, 1H). |
| YJP-51 | 3'-Cl | 2,4-DiCl | O | 4.28(s, 5H, $\eta^5$-C₅H₅), 4.31(t, 2H, J = 2.0 Hz), 4.55(t, 2H, J = 2.0 Hz), 5.52(s, 2H), 6.90(s, 1H), 7.38(dd, 1H, J = 2.0, 2.0 Hz), 7.55(d, 1H, J = 2.0 Hz), 7.59(s, 1H), 7.68(d, 1H, J = 5.6 Hz), 7.74(d, 1H, J = 8.4 Hz), 7.78(d, 1H, J = 5.8 Hz). |
| YJP-52 | 3'-Cl | 4-Br | O | 4.28(s, 5H, $\eta^5$-C₅H₅), 4.31(t, 2H, J = 1.6 Hz), 4.56(t, 2H, J = 2.0 Hz), 5.51(s, 2H), 6.71(s, 1H), 7.47(d, 2H, J = 8.4 Hz), 7.59(s, 1H), 7.68(d, 1H, J = 5.6 Hz), 7.78(d, 1H, J = 5.8 Hz), 7.79(d, 2H, J = 8.4 Hz). |

TABLE 1-continued

¹H NMR of the compounds of formula I

| No. | R₁ | (R₂)ₙ | Z | ¹H NMR (400 MHz, CDCl₃) |
|---|---|---|---|---|
| YJP-53 | 3'-Cl | 2-Br | O | 4.28(s, 5H, $\eta^5$-C₅H₅), 4.31(t, 2H, J = 2.0 Hz), 4.56(t, 2H, J = 2.0 Hz), 5.52(s, 2H), 6.86(s, 1H), 7.21(ddd, 1H, J = 0.8, 0.8, 1.2 Hz), 7.24(dd, 1H, J = 0.8, 1.2 Hz), 7.29(dd, 1H, J = 0.8, 1.2 Hz), 7.44-7.48(m, 1H), 7.59(s, 1H), 7.68(d, 1H, J = 5.6 Hz), 7.78(d, 1H, J = 5.8 Hz). |
| YJP-54 | 3'-Cl | 3-Br | O | 4.28(s, 5H, $\eta^5$-C₅H₅), 4.31(t, 2H, J = 2.0 Hz), 4.55(t, 2H, J = 1.6 Hz), 5.53(s, 2H), 6.64(s, 1H), 7.69(d, 2H, J = 8.4 Hz), 7.63-7.68(m, 3H), 7.59(s, 1H), 7.68(d, 1H, J = 5.6 Hz), 7.78(d, 1H, J = 5.8 Hz). |
| YJP-55 | 3'-Cl | 4-CF₃ | O | 4.28(s, 5H, $\eta^5$-C₅H₅), 4.31(t, 2H, J = 1.6 Hz), 4.55(t, 2H, J = 1.6 Hz), 5.52(s, 2H), 6.78(s, 1H), 7.59(s, 1H), 7.68(d, 1H, J = 5.6 Hz), 7.76(d, 2H, J = 8.0 Hz), 7.78(d, 1H, J = 5.8 Hz), 7.98(d, 2H, J = 8.4 Hz). |
| YJP-56 | 3'-Cl | 2-CF₃ | O | 4.28(s, 5H, $\eta^5$-C₅H₅), 4.31(t, 2H, J = 2.0 Hz), 4.55(t, 2H, J = 1.6 Hz), 5.53(s, 2H), 6.64(s, 1H), 7.59(s, 1H), 7.68(d, 1H, J = 5.6 Hz), 7.63-7.68(m, 3H), 7.78(d, 1H, J = 5.8 Hz), 7.85(d, 1H, J = 7.6 Hz). |
| YJP-57 | 3'-Cl | 4-NO₂ | O | 4.28(s, 5H, $\eta^5$-C₅H₅), 4.31(t, 2H, J = 2.0 Hz), 4.55(t, 2H, J = 2.0 Hz), 5.53(s, 2H), 6.81(s, 1H), 7.45(d, 2H, J = 8.4 Hz), 7.59(s, 1H), 7.68(d, 1H, J = 5.6 Hz), 7.78(d, 1H, J = 5.8 Hz), 8.36(d, 2H, J = 8.4 Hz). |
| YJP-58 | 3'-F | H | O | 4.28(s, 5H, $\eta^5$-C₅H₅), 4.31(t, 2H, J = 1.6 Hz), 4.55(t, 2H, J = 1.6 Hz), 5.50(s, 2H), 6.71(s, 1H), 7.48-7.52 (m, 3H, Ph—H), 7.59(s, 1H), 7.68(d, 1H, J = 5.6 Hz), 7.78(d, 1H, J = 5.8 Hz), 7.83-7.85 (m, 2H, Ph—H). |
| YJP-59 | 3'-F | 4-CH₃ | O | 2.43(s, 3H, CH₃), 4.28(s, 5H, $\eta^5$-C₅H₅), 4.31(t, 2H, J = 1.6 Hz), 4.55(t, 2H, J = 1.6 Hz), 5.50(s, 2H), 6.71(s, 1H), 7.31(d, 2H, J = 6.4 Hz), 7.59(s, 1H), 7.68(d, 1H, J = 5.6 Hz), 7.74(d, 2H, J = 8.0 Hz), 7.78(d, 1H, J = 5.8 Hz). |
| YJP-60 | 3'-F | 4-CH₂CH₃ | O | 1.30(t, 3H, CH₃, J = 7.6 Hz), 2.74(q, 2H, CH₂CH₃, J = 8.0 Hz), 4.28(s, 5H, $\eta^5$-C₅H₅), 4.31(t, 2H, J = 2.0 Hz), 4.55(t, 2H, J = 2.0 Hz), 5.48(s, 2H), 6.71(s, 1H), 7.32(d, 2H, J = 8.0 Hz), 7.59(s, 1H), 7.68(d, 1H, J = 5.6 Hz), 7.76(d, 2H, J = 8.4 Hz), 7.78(d, 1H, J = 5.8 Hz). |
| YJP-61 | 3'-F | 4-C(CH₃)₃ | O | 1.38(s, 9H, 3CH₃), 4.28(s, 5H, $\eta^5$-C₅H₅), 4.31(t, 2H, J = 1.6 Hz), 4.55(t, 2H, J = 1.6 Hz), 5.50(s, 2H), 6.71(s, 1H), 7.51(d, 2H, J = 8.4 Hz), 7.59(s, 1H), 7.68(d, 1H, J = 5.6 Hz), 7.78(d, 1H, J = 5.8 Hz), 7.81(d, 2H, J = 8.4 Hz). |
| YJP-62 | 3'-F | 2,4,6-TriCH₃ | O | 2.18(s, 6H, 2CH₃), 2.35(s, 3H, CH₃), 4.28(s, 5H, $\eta^5$-C₅H₅), 4.31(t, 2H, J = 2.0 Hz), 4.56(t, 2H, J = 2.0 Hz), 5.54(s, 2H), 6.36(s, 1H), 6.97(s, 1H), 7.29(s, 1H), 7.59(s, 1H), 7.68(d, 1H, J = 5.6 Hz), 7.78(d, 1H, J = 5.8 Hz). |
| YJP-63 | 3'-F | 4-OCH₃ | O | 3.88(s, 3H, OCH₃), 4.28(s, 5H, $\eta^5$-C₅H₅), 4.31(t, 2H, J = 2.0 Hz), 4.55(t, 2H, J = 1.6 Hz), 5.48(s, 2H), 6.68(s, 1H), 7.01(d, 2H, J = 7.2 Hz), 7.59(s, 1H), 7.68(d, 1H, J = 5.6 Hz), 7.78(d, 1H, J = 5.8 Hz), 7.81(d, 2H, J = 8.8 Hz). |
| YJP-64 | 3'-F | 2-OCH₃ | O | 3.94(s, 3H, OCH₃), 4.28(s, 5H, $\eta^5$-C₅H₅), 4.31(t, 2H, J = 2.0 Hz), 4.56(t, 2H, J = 2.0 Hz), 5.50(s, 2H), 6.94(s, 1H), 7.02-7.09(m, 2H), 7.43-7.48(m, 1H), 7.59(s, 1H), 7.68(d, 1H, J = 5.6 Hz), 7.78(d, 1H, J = 5.8 Hz), 7.93(dd, 1H, J = 1.6, 2.0 Hz). |
| YJP-65 | 3'-F | 3-OCH₃ | O | 3.89(s, 3H, OCH₃), 4.28(s, 5H, $\eta^5$-C₅H₅), 4.31(t, 2H, J = 2.0 Hz), 4.55(t, 2H, J = 2.0 Hz), 5.51(s, 2H), 6.72(s, 1H), 7.01-7.04(m, 1H), 7.39-7.41(m, 1H), 7.59(s, 1H), 7.68(d, 1H, J = 5.6 Hz), 7.78(d, 1H, J = 5.8 Hz). |
| YJP-66 | 3'-F | 4-F | O | 4.27(s, 5H, $\eta^5$-C₅H₅), 4.31(t, 2H, J = 2.0 Hz), 4.55(t, 2H, J = 2.0 Hz), 5.51(s, 2H), 6.70(s, 1H), 7.18(d, 2H, J = 8.4 Hz), 7.59(s, 1H), 7.68(d, 1H, J = 5.6 Hz), 7.78(d, 1H, J = 5.8 Hz), 7.82(d, 2H, J = 8.8 Hz). |
| YJP-67 | 3'-F | 2-F | O | 4.28(s, 5H, $\eta^5$-C₅H₅), 4.31(t, 2H, J = 2.0 Hz), 4.56(t, 2H, J = 2.0 Hz), 5.52(s, 2H), 6.87(s, 1H), 7.20-7.29(m, 3H), 7.44-7.49(m, 1H), 7.59(s, 1H), 7.68(d, 1H, J = 5.6 Hz), 7.78(d, 1H, J = 5.8 Hz). |
| YJP-68 | 3'-F | 4-Cl | O | 4.28(s, 5H, $\eta^5$-C₅H₅), 4.31(t, 2H, J = 1.6 Hz), 4.56(t, 2H, J = 2.0 Hz), 5.51(s, 2H), 6.71(s, 1H), 7.47(d, 2H, J = 8.4 Hz), 7.59(s, 1H), 7.68(d, 1H, J = 5.6 Hz), 7.78(d, 1H, J = 5.8 Hz), 7.82(d, 2H, J = 8.4 Hz). |
| YJP-69 | 3'-F | 2-Cl | O | 4.28(s, 5H, $\eta^5$-C₅H₅), 4.31(t, 2H, J = 2.0 Hz), 4.55(t, 2H, J = 2.0 Hz), 5.53(s, 2H), 6.90(s, 1H), 7.37-7.45(m, 2H), 7.53(dd, 1H, J = 1.2, 1.6 Hz), 7.59(s, 1H), 7.68(d, 1H, J = 5.6 Hz), 7.78(d, 1H, J = 5.8 Hz), 7.79-7.81(m, 1H). |
| YJP-70 | 3'-F | 2,4-DiCl | O | 4.28(s, 5H, $\eta^5$-C₅H₅), 4.31(t, 2H, J = 2.0 Hz), 4.55(t, 2H, J = 2.0 Hz), 5.52(s, 2H), 6.90(s, 1H), 7.38(dd, 1H, J = 2.0, 2.0 Hz), 7.55(d, 1H, J = 2.0 Hz), 7.59(s, 1H), 7.68(d, 1H, J = 5.6 Hz), 7.74(d, 1H, J = 8.4 Hz), 7.78(d, 1H, J = 5.8 Hz). |

TABLE 1-continued

¹H NMR of the compounds of formula I

| No. | R₁ | (R₂)ₙ | Z | ¹H NMR (400 MHz, CDCl₃) |
|---|---|---|---|---|
| YJP-71 | 3'-F | 4-Br | O | 4.28(s, 5H, η⁵-C₅H₅), 4.31(t, 2H, J = 1.6 Hz), 4.56(t, 2H, J = 2.0 Hz), 5.51(s, 2H), 6.71(s, 1H), 7.47(d, 2H, J = 8.4 Hz), 7.59(s, 1H), 7.68(d, 1H, J = 5.6 Hz), 7.78(d, 1H, J = 5.8 Hz), 7.79(d, 2H, J = 8.4 Hz). |
| YJP-72 | 3'-F | 2-Br | O | 4.28(s, 5H, η⁵-C₅H₅), 4.31(t, 2H, J = 2.0 Hz), 4.56(t, 2H, J = 2.0 Hz), 5.52(s, 2H), 6.86(s, 1H), 7.21(ddd, 1H, J = 0.8, 0.8, 1.2 Hz), 7.24(dd, 1H, J = 0.8, 1.2 Hz), 7.29(dd, 1H, J = 0.8, 1.2 Hz), 7.44-7.48(m, 1H), 7.59(s, 1H), 7.68(d, 1H, J = 5.6 Hz), 7.78(d, 1H, J = 5.8 Hz). |
| YJP-73 | 3'-F | 3-Br | O | 4.28(s, 5H, η⁵-C₅H₅), 4.31(t, 2H, J = 2.0 Hz), 4.55(t, 2H, J = 1.6 Hz), 5.53(s, 2H), 6.64(s, 1H), 7.69(d, 2H, J = 8.4 Hz), 7.63-7.68(m, 3H), 7.59(s, 1H), 7.68(d, 1H, J = 5.6 Hz), 7.78(d, 1H, J = 5.8 Hz). |
| YJP-74 | 3'-F | 4-CF₃ | O | 4.28(s, 5H, η⁵-C₅H₅), 4.31(t, 2H, J = 1.6 Hz), 4.55(t, 2H, J = 1.6 Hz), 5.52(s, 2H), 6.78(s, 1H), 7.59(s, 1H), 7.68(d, 1H, J = 5.6 Hz), 7.76(d, 2H, J = 8.0 Hz), 7.78(d, 1H, J = 5.8 Hz), 7.98(d, 2H, J = 8.4 Hz). |
| YJP-75 | 3'-F | 2-CF₃ | O | 4.28(s, 5H, η⁵-C₅H₅), 4.31(t, 2H, J = 2.0 Hz), 4.55(t, 2H, J = 1.6 Hz), 5.53(s, 2H), 6.64(s, 1H), 7.59(s, 1H), 7.68(d, 1H, J = 5.6 Hz), 7.63-7.68(m, 3H), 7.78(d, 1H, J = 5.8 Hz), 7.85(d, 1H, J = 7.6 Hz). |
| YJP-76 | 3'-F | 4-NO₂ | O | 4.28(s, 5H, η⁵-C₅H₅), 4.31(t, 2H, J = 2.0 Hz), 4.55(t, 2H, J = 2.0 Hz), 5.53(s, 2H), 6.81(s, 1H), 7.45(d, 2H, J = 8.4 Hz), 7.59(s, 1H), 7.68(d, 1H, J = 5.6 Hz), 7.78(d, 1H, J = 5.8 Hz), 8.36(d, 2H, J = 8.4 Hz). |
| YJP-77 | H | H | NH | 4.28(s, 5H, η⁵-C₅H₅), 4.31(t, 2H, J = 1.6 Hz), 4.55(t, 2H, J = 1.6 Hz), 5.50(s, 2H), 5.66(t, 1H, NH—CO—, J = 4.6 Hz), 6.71(s, 1H), 7.48-7.52 (m, 3H, Ph—H), 7.83-7.85 (m, 2H, Ph—H), 7.59(d, 2H, J = 8.4 Hz), 8.09(d, 2H, J = 8.4 Hz). |
| YJP-78 | H | 4-CH₃ | NH | 2.43(s, 3H, CH₃), 4.28(s, 5H, η⁵-C₅H₅), 4.31(t, 2H, J = 1.6 Hz), 4.55(t, 2H, J = 1.6 Hz), 5.50(s, 2H), 5.66(t, 1H, NH—CO—, J = 4.6 Hz), 6.71(s, 1H), 7.31(d, 2H, J = 6.4 Hz), 7.58(d, 2H, J = 8.4 Hz), 7.74(d, 2H, J = 8.0 Hz), 8.07(d, 2H, J = 8.4 Hz). |
| YJP-79 | H | 4-CH₂CH₃ | NH | 1.30(t, 3H, CH₃, J = 7.6 Hz), 2.74(q, 2H, CH₂CH₃, J = 8.0 Hz), 4.28(s, 5H, η⁵-C₅H₅), 4.31(t, 2H, J = 2.0 Hz), 4.55(t, 2H, J = 2.0 Hz), 5.48(s, 2H), 5.66(t, 1H, NH—CO—, J = 4.6 Hz), 6.71(s, 1H), 7.32(d, 2H, J = 8.0 Hz), 7.58(d, 2H, J = 8.4 Hz), 7.76(d, 2H, J = 8.4 Hz), 8.07(d, 2H, J = 8.0 Hz). |
| YJP-80 | H | 4-C(CH₃)₃ | NH | 1.38(s, 9H, 3CH₃), 4.28(s, 5H, η⁵-C₅H₅), 4.31(t, 2H, J = 1.6 Hz), 4.55(t, 2H, J = 1.6 Hz), 5.50(s, 2H), 5.66(t, 1H, NH—CO—, J = 4.6 Hz), 6.71(s, 1H), 7.51(d, 2H, J = 8.4 Hz), 7.58(d, 2H, J = 8.8 Hz), 7.79(d, 2H, J = 8.4 Hz), 8.07(d, 2H, J = 8.4 Hz). |
| YJP-81 | H | 2,4,6-TriCH₃ | NH | 2.18(s, 6H, 2CH₃), 2.35(s, 3H, CH₃), 4.28(s, 5H, η⁵-C₅H₅), 4.31(t, 2H, J = 2.0 Hz), 4.56(t, 2H, J = 2.0 Hz), 5.54(s, 2H), 5.66(t, 1H, NH—CO—, J = 4.6 Hz), 6.36(s, 1H), 6.97(s, 1H), 7.29(s, 1H), 7.59(d, 2H, J = 8.4 Hz), 8.07(d, 2H, J = 8.4 Hz). |
| YJP-82 | H | 4-OCH₃ | NH | 3.88(s, 3H, OCH₃), 4.28(s, 5H, η⁵-C₅H₅), 4.31(t, 2H, J = 2.0 Hz), 4.55(t, 2H, J = 1.6 Hz), 5.48(s, 2H), 5.66(t, 1H, NH—CO—, J = 4.6 Hz), 6.68(s, 1H), 7.01(d, 2H, J = 7.2 Hz), 7.58(d, 2H, J = 8.4 Hz), 7.79(d, 2H, J = 8.8 Hz), 8.06(d, 2H, J = 8.4 Hz). |
| YJP-83 | H | 2-OCH₃ | NH | 3.94(s, 3H, OCH₃), 4.28(s, 5H, η⁵-C₅H₅), 4.31(t, 2H, J = 2.0 Hz), 4.56(t, 2H, J = 2.0 Hz), 5.50(s, 2H), 5.66(t, 1H, NH—CO—, J = 4.6 Hz), 6.94(s, 1H), 7.02-7.09(m, 2H), 7.43-7.48(m, 1H), 7.57(d, 2H, J = 8.8 Hz), 7.93(dd, 1H, J = 1.6, 2.0 Hz), 8.06 (d, 2H, J = 8.4 Hz). |
| YJP-84 | H | 3-OCH₃ | NH | 3.89(s, 3H, OCH₃), 4.28(s, 5H, η⁵-C₅H₅), 4.31(t, 2H, J = 2.0 Hz), 4.55(t, 2H, J = 2.0 Hz), 5.51(s, 2H), 5.66(t, 1H, NH—CO—, J = 4.6 Hz), 6.72(s, 1H), 7.01-7.04(m, 1H), 7.39-7.41(m, 1H), 7.58(d, 2H, J = 8.4 Hz), 8.06(d, 2H, J = 8.4 Hz). |
| YJP-85 | H | 4-F | NH | 4.27(s, 5H, η⁵-C₅H₅), 4.31(t, 2H, J = 2.0 Hz), 4.55(t, 2H, J = 2.0 Hz), 5.51(s, 2H), 5.66(t, 1H, NH—CO—, J = 4.6 Hz), 6.70(s, 1H), 7.18(d, 2H, J = 8.4 Hz), 7.58(d, 2H, J = 8.8 Hz), 7.82(d, 2H, J = 8.8 Hz), 8.06(d, 2H, J = 8.4 Hz). |
| YJP-86 | H | 2-F | NH | 4.28(s, 5H, η⁵-C₅H₅), 4.31(t, 2H, J = 2.0 Hz), 4.56(t, 2H, J = 2.0 Hz), 5.52(s, 2H), 5.66(t, 1H, NH—CO—, J = 4.6 Hz), 6.87(s, 1H), 7.20-7.29(m, 3H), 7.44-7.49(m, 1H), 7.58(d, 2H, J = 8.8 Hz), 8.06(d, 2H, J = 8.8 Hz). |

TABLE 1-continued

| No. | $R_1$ | $(R_2)_n$ | Z | $^1$H NMR (400 MHz, CDCl$_3$) |
|---|---|---|---|---|
| YJP-87 | H | 4-Cl | NH | 4.28(s, 5H, η$^5$-C$_5$H$_5$), 4.31(t, 2H, J = 1.6 Hz), 4.56(t, 2H, J = 2.0 Hz), 5.51(s, 2H), 5.66(t, 1H, NH—CO—, J = 4.6 Hz), 6.71(s, 1H), 7.47(d, 2H, J = 8.4 Hz), 7.58(d, 2H, J = 8.4 Hz), 7.79(d, 2H, J = 8.4 Hz), 8.06(d, 2H, J = 8.4 Hz). |
| YJP-88 | H | 2-Cl | NH | 4.28(s, 5H, η$^5$-C$_5$H$_5$), 4.31(t, 2H, J = 2.0 Hz), 4.55(t, 2H, J = 2.0 Hz), 5.53(s, 2H), 5.66(t, 1H, NH—CO—, J = 4.6 Hz), 6.90(s, 1H), 7.37-7.45(m, 2H), 7.53(dd, 1H, J = 1.2, 1.6 Hz), 7.58(d, 2H, J = 8.8 Hz), 7.76-7.79(m, 1H), 8.07(d, 2H, J = 8.4 Hz). |
| YJP-89 | H | 2,4-DiCl | NH | 4.28(s, 5H, η$^5$-C$_5$H$_5$), 4.31(t, 2H, J = 2.0 Hz), 4.55(t, 2H, J = 2.0 Hz), 5.52(s, 2H), 5.66(t, 1H, NH—CO—, J = 4.6 Hz), 6.90(s, 1H), 7.38(dd, 1H, J = 2.0, 2.0 Hz), 7.55(d, 1H, J = 2.0 Hz), 7.58(d, 2H, J = 8.4 Hz), 7.74(d, 1H, J = 8.4 Hz), 8.07(d, 2H, J = 8.4 Hz). |
| YJP-90 | H | 4-Br | NH | 4.28(s, 5H, η$^5$-C$_5$H$_5$), 4.31(t, 2H, J = 1.6 Hz), 4.56(t, 2H, J = 2.0 Hz), 5.51(s, 2H), 5.66(t, 1H, NH—CO—, J = 4.6 Hz), 6.71(s, 1H), 7.47(d, 2H, J = 8.4 Hz), 7.58(d, 2H, J = 8.4 Hz), 7.79(d, 2H, J = 8.4 Hz), 8.06(d, 2H, J = 8.4 Hz). |
| YJP-91 | H | 2-Br | NH | 4.28(s, 5H, η$^5$-C$_5$H$_5$), 4.31(t, 2H, J = 2.0 Hz), 4.56(t, 2H, J = 2.0 Hz), 5.52(s, 2H), 5.66(t, 1H, NH—CO—, J = 4.6 Hz), 6.86(s, 1H), 7.21(ddd, 1H, J = 0.8, 0.8, 1.2 Hz), 7.24(dd, 1H, J = 0.8, 1.2 Hz), 7.29(dd, 1H, J = 0.8, 1.2 Hz), 7.44-7.48(m, 1H), 7.55(d, 2H, J = 8.8 Hz), 8.07(d, 2H, J = 8.4 Hz). |
| YJP-92 | H | 3-Br | NH | 4.28(s, 5H, η$^5$-C$_5$H$_5$), 4.31(t, 2H, J = 2.0 Hz), 4.55(t, 2H, J = 1.6 Hz), 5.53(s, 2H), 5.66(t, 1H, NH—CO—, J = 4.6 Hz), 6.64(s, 1H), 7.69(d, 2H, J = 8.4 Hz), 7.63-7.68(m, 3H), 7.85(d, 1H, J = 7.6 Hz), 8.07(d, 2H, J = 8.4 Hz). |
| YJP-93 | H | 4-CF$_3$ | NH | 4.28(s, 5H, η$^5$-C$_5$H$_5$), 4.31(t, 2H, J = 1.6 Hz), 4.55(t, 2H, J = 1.6 Hz), 5.52(s, 2H), 5.66(t, 1H, NH—CO—, J = 4.6 Hz), 6.78(s, 1H), 7.58(d, 2H, J = 8.4 Hz), 7.76(d, 2H, J = 8.0 Hz), 7.98(d, 2H, J = 8.4 Hz), 8.06(d, 2H, J = 8.4 Hz). |
| YJP-94 | H | 2-CF$_3$ | NH | 4.28(s, 5H, η$^5$-C$_5$H$_5$), 4.31(t, 2H, J = 2.0 Hz), 4.55(t, 2H, J = 1.6 Hz), 5.53(s, 2H), 5.66(t, 1H, NH—CO—, J = 4.6 Hz), 6.64(s, 1H), 7.69(d, 2H, J = 8.4 Hz), 7.63-7.68(m, 3H), 7.85(d, 1H, J = 7.6 Hz), 8.07(d, 2H, J = 8.4 Hz). |
| YJP-95 | H | 4-NO$_2$ | NH | 4.28(s, 5H, η$^5$-C$_5$H$_5$), 4.31(t, 2H, J = 2.0 Hz), 4.55(t, 2H, J = 2.0 Hz), 5.53(s, 2H), 5.66(t, 1H, NH—CO—, J = 4.6 Hz), 6.81(s, 1H), 7.45(d, 2H, J = 8.4 Hz), 7.58(d, 2H, J = 8.4 Hz), 8.06(d, 2H, J = 8.4 Hz), 8.36(d, 2H, J = 8.4 Hz). |
| YJP-96 | 3'-CH$_3$ | H | NH | 2.49(s, 5H, η$^5$-C$_5$H$_5$), 4.28(s, 5H, C$_5$H$_5$), 4.31(t, 2H, J = 1.6 Hz), 4.55(t, 2H, J = 1.6 Hz), 5.50(s, 2H), 5.66(t, 1H, NH—CO—, J = 4.6 Hz), 6.71(s, 1H), 7.48-7.52 (m, 3H, Ph—H), 7.58(d, 1H, J = 6.5 Hz), 7.72(s, 1H), 7.82(d, 1H, J = 5.8 Hz), 7.83-7.85 (m, 2H, Ph—H). |
| YJP-97 | 3'-CH$_3$ | 4-CH$_3$ | NH | 2.43(s, 3H, CH$_3$), 2.49(s, 3H, CH$_3$), 4.28(s, 5H, η$^5$-C$_5$H$_5$), 4.31(t, 2H, J = 1.6 Hz), 4.55(t, 2H, J = 1.6 Hz), 5.50(s, 2H), 5.66(t, 1H, NH—CO—, J = 4.6 Hz), 6.71(s, 1H), 7.31(d, 2H, J = 6.4 Hz), 7.58(d, 1H, J = 6.5 Hz), 7.72(s, 1H), 7.82(d, 1H, J = 5.8 Hz), 7.82(d, 1H, J = 5.8 Hz). |
| YJP-98 | 3'-CH$_3$ | 4-CH$_2$CH$_3$ | NH | 1.30(t, 3H, CH$_3$, J = 7.6 Hz), 2.49(s, 3H, CH$_3$), 2.74(q, 2H, CH$_2$CH$_3$, J = 8.0 Hz), 4.28(s, 5H, η$^5$-C$_5$H$_5$), 4.31(t, 2H, J = 2.0 Hz), 4.55(t, 2H, J = 2.0 Hz), 5.48(s, 2H), 5.66(t, 1H, NH—CO—, J = 4.6 Hz), 6.71(s, 1H), 7.32(d, 2H, J = 8.0 Hz), 7.58(d, 1H, J = 6.5 Hz), 7.72(s, 1H), 7.82(d, 1H, J = 5.8 Hz), 7.76(d, 2H, J = 8.4 Hz). |
| YJP-99 | 3'-CH$_3$ | 4-C(CH$_3$)$_3$ | NH | 1.38(s, 9H, 3CH$_3$), 2.49(s, 3H, CH$_3$), 4.28(s, 5H, η$^5$-C$_5$H$_5$), 4.31(t, 2H, J = 1.6 Hz), 4.55(t, 2H, J = 1.6 Hz), 5.50(s, 2H), 5.66(t, 1H, NH—CO—, J = 4.6 Hz), 6.71(s, 1H), 7.51(d, 2H, J = 8.4 Hz), 7.58(d, 1H, J = 6.5 Hz), 7.72(s, 1H), 7.82(d, 1H, J = 5.8 Hz), 7.79(d, 2H, J = 8.4 Hz). |
| YJP-100 | 3'-CH$_3$ | 2,4,6-TriCH$_3$ | NH | 2.18(s, 6H, 2CH$_3$), 2.35(s, 3H, CH$_3$), 2.49(s, 3H, CH$_3$), 4.28(s, 5H, η$^5$-C$_5$H$_5$), 4.31(t, 2H, J = 2.0 Hz), 4.56(t, 2H, J = 2.0 Hz), 5.54(s, 2H), 5.66(t, 1H, NH—CO—, J = 4.6 Hz), 6.36(s, 1H), 6.97(s, 1H), 7.29(s, 1H), 7.58(d, 1H, J = 6.5 Hz), 7.72(s, 1H), 7.82(d, 1H, J = 5.8 Hz). |
| YJP-101 | 3'-CH$_3$ | 4-OCH$_3$ | NH | 2.49(s, 3H, CH$_3$), 3.88(s, 3H, OCH$_3$), 4.28(s, 5H, η$^5$-C$_5$H$_5$), 4.31(t, 2H, J = 2.0 Hz), 4.55(t, 2H, J = 1.6 Hz), 5.48(s, 2H), 5.66(t, 1H, NH—CO—, J = 4.6 Hz), 6.68(s, 1H), 7.01(d, 2H, J = 7.2 Hz), 7.58(d, 1H, J = 6.5 Hz), 7.72(s, 1H), 7.79(d, 2H, J = 8.8 Hz), 7.82(d, 1H, J = 5.8 Hz). |

TABLE 1-continued

¹H NMR of the compounds of formula I

| No. | R₁ | (R₂)ₙ | Z | ¹H NMR (400 MHz, CDCl₃) |
|---|---|---|---|---|
| YJP-102 | 3'-CH₃ | 2-OCH₃ | NH | 2.49(s, 3H, CH₃), 3.94(s, 3H, OCH₃), 4.28(s, 5H, η⁵-C₅H₅), 4.31(t, 2H, J = 2.0 Hz), 4.56(t, 2H, J = 2.0 Hz), 5.50(s, 2H), 5.66(t, 1H, NH—CO—, J = 4.6 Hz), 6.94(s, 1H), 7.02-7.09(m, 2H), 7.43-7.48(m, 1H), 7.58(d, 1H, J = 6.5 Hz), 7.72(s, 1H), 7.82(d, 1H, J = 5.8 Hz), 7.93(dd, 1H, J = 1.6, 2.0 Hz). |
| YJP-103 | 3'-CH₃ | 3-OCH₃ | NH | 2.49(s, 3H, CH₃), 3.89(s, 3H, OCH₃), 4.28(s, 5H, η⁵-C₅H₅), 4.31(t, 2H, J = 2.0 Hz), 4.55(t, 2H, J = 2.0 Hz), 5.51(s, 2H), 5.66(t, 1H, NH—CO—, J = 4.6 Hz), 6.72(s, 1H), 7.01-7.04(m, 1H), 7.39-7.41(m, 1H), 7.58(d, 1H, J = 6.5 Hz), 7.72(s, 1H), 7.82(d, 1H, J = 5.8 Hz). |
| YJP-104 | 3'-CH₃ | 4-F | NH | 2.49(s, 3H, CH₃), 4.27(s, 5H, η⁵-C₅H₅), 4.31(t, 2H, J = 2.0 Hz), 4.55(t, 2H, J = 2.0 Hz), 5.51(s, 2H), 5.66(t, 1H, NH—CO—, J = 4.6 Hz), 6.70(s, 1H), 7.18(d, 2H, J = 8.4 Hz), 7.58(d, 1H, J = 6.5 Hz), 7.72(s, 1H), 7.82(d, 1H, J = 5.8 Hz), 7.83(d, 2H, J = 8.8 Hz). |
| YJP-105 | 3'-CH₃ | 2-F | NH | 2.49(s, 3H, CH₃), 4.28(s, 5H, η⁵-C₅H₅), 4.31(t, 2H, J = 2.0 Hz), 4.56(t, 2H, J = 2.0 Hz), 5.52(s, 2H), 5.66(t, 1H, NH—CO—, J = 4.6 Hz), 6.87(s, 1H), 7.20-7.29(m, 3H), 7.44-7.49(m, 1H), 7.58(d, 1H, J = 6.5 Hz), 7.72(s, 1H), 7.82(d, 1H, J = 5.8 Hz). |
| YJP-106 | 3'-CH₃ | 4-Cl | NH | 2.49(s, 3H, CH₃), 4.28(s, 5H, η⁵-C₅H₅), 4.31(t, 2H, J = 1.6 Hz), 4.56(t, 2H, J = 2.0 Hz), 5.51(s, 2H), 5.66(t, 1H, NH—CO—, J = 4.6 Hz), 6.71(s, 1H), 7.47(d, 2H, J = 8.4 Hz), 7.58(d, 1H, J = 6.5 Hz), 7.72(s, 1H), 7.79(d, 2H, J = 8.4 Hz), 7.82(d, 1H, J = 5.8 Hz). |
| YJP-107 | 3'-CH₃ | 2-Cl | NH | 2.49(s, 3H, CH₃), 4.28(s, 5H, η⁵-C₅H₅), 4.31(t, 2H, J = 2.0 Hz), 4.55(t, 2H, J = 2.0 Hz), 5.53(s, 2H), 5.66(t, 1H, NH—CO—, J = 4.6 Hz), 6.90(s, 1H), 7.37-7.45(m, 2H), 7.53(dd, 1H, J = 1.2, 1.6 Hz), 7.58(d, 1H, J = 6.5 Hz), 7.72(s, 1H), 7.76-7.79(m, 1H), 7.82(d, 1H, J = 5.8 Hz). |
| YJP-108 | 3'-CH₃ | 2,4-DiCl | NH | 2.49(s, 3H, CH₃), 4.28(s, 5H, η⁵-C₅H₅), 4.31(t, 2H, J = 2.0 Hz), 4.55(t, 2H, J = 2.0 Hz), 5.52(s, 2H), 5.66(t, 1H, NH—CO—, J = 4.6 Hz), 6.90(s, 1H), 7.38(dd, 1H, J = 2.0, 2.0 Hz), 7.55(d, 1H, J = 2.0 Hz), 7.58(d, 1H, J = 6.5 Hz), 7.72(s, 1H), 7.74(d, 1H, J = 8.4 Hz), 7.82(d, 1H, J = 5.8 Hz). |
| YJP-109 | 3'-CH₃ | 4-Br | NH | 2.49(s, 3H, CH₃), 4.28(s, 5H, η⁵-C₅H₅), 4.31(t, 2H, J = 1.6 Hz), 4.56(t, 2H, J = 2.0 Hz), 5.51(s, 2H), 5.66(t, 1H, NH—CO—, J = 4.6 Hz), 6.71(s, 1H), 7.47(d, 2H, J = 8.4 Hz), 7.58(d, 1H, J = 6.5 Hz), 7.72(s, 1H), 7.79(d, 2H, J = 8.4 Hz), 7.82(d, 1H, J = 5.8 Hz). |
| YJP-110 | 3'-CH₃ | 2-Br | NH | 2.49(s, 3H, CH₃), 4.28(s, 5H, η⁵-C₅H₅), 4.31(t, 2H, J = 2.0 Hz), 4.56(t, 2H, J = 2.0 Hz), 5.52(s, 2H), 5.66(t, 1H, NH—CO—, J = 4.6 Hz), 6.86(s, 1H), 7.21(ddd, 1H, J = 0.8, 0.8, 1.2 Hz), 7.24(dd, 1H, J = 0.8, 1.2 Hz), 7.29(dd, 1H, J = 0.8, 1.2 Hz), 7.44-7.48(m, 1H), 7.58(d, 1H, J = 6.5 Hz), 7.72(s, 1H), 7.82(d, 1H, J = 5.8 Hz). |
| YJP-111 | 3'-CH₃ | 3-Br | NH | 2.49(s, 3H, CH₃), 4.28(s, 5H, η⁵-C₅H₅), 4.31(t, 2H, J = 2.0 Hz), 4.55(t, 2H, J = 1.6 Hz), 5.53(s, 2H), 5.66(t, 1H, NH—CO—, J = 4.6 Hz), 6.64(s, 1H), 7.58(d, 1H, J = 6.5 Hz), 7.63-7.68(m, 3H), 7.72(s, 1H), 7.82(d, 1H, J = 5.8 Hz), 7.85(d, 1H, J = 7.6 Hz). |
| YJP-112 | 3'-CH₃ | 4-CF₃ | NH | 2.49(s, 3H, CH₃), 4.28(s, 5H, η⁵-C₅H₅), 4.31(t, 2H, J = 1.6 Hz), 4.55(t, 2H, J = 1.6 Hz), 5.52(s, 2H), 5.66(t, 1H, NH—CO—, J = 4.6 Hz), 6.78(s, 1H), 7.58(d, 1H, J = 6.5 Hz), 7.72(s, 1H), 7.76(d, 2H, J = 8.0 Hz), 7.85(d, 1H, J = 7.6 Hz), 7.98(d, 2H, J = 8.4 Hz). |
| YJP-113 | 3'-CH₃ | 2-CF₃ | NH | 2.49(s, 3H, CH₃), 4.28(s, 5H, η⁵-C₅H₅), 4.31(t, 2H, J = 2.0 Hz), 4.55(t, 2H, J = 1.6 Hz), 5.53(s, 2H), 5.66(t, 1H, NH—CO—, J = 4.6 Hz), 6.64(s, 1H), 7.58(d, 1H, J = 6.5 Hz), 7.63-7.68(m, 3H), 7.72(s, 1H), 7.82(d, 1H, J = 5.8 Hz), 7.85(d, 1H, J = 7.6 Hz). |
| YJP-114 | 3'-CH₃ | 4-NO₂ | NH | 2.49(s, 3H, CH₃), 4.28(s, 5H, η⁵-C₅H₅), 4.31(t, 2H, J = 2.0 Hz), 4.55(t, 2H, J = 2.0 Hz), 5.53(s, 2H), 5.66(t, 1H, NH—CO—, J = 4.6 Hz), 6.81(s, 1H), 7.45(d, 2H, J = 8.4 Hz), 7.58(d, 1H, J = 6.5 Hz), 7.72(s, 1H), 7.82(d, 1H, J = 5.8 Hz), 8.36(d, 2H, J = 8.4 Hz). |
| YJP-115 | 3'-Cl | H | NH | 4.28(s, 5H, η⁵-C₅H₅), 4.31(t, 2H, J = 1.6 Hz), 4.55(t, 2H, J = 1.6 Hz), 5.50(s, 2H), 5.66(t, 1H, NH—CO—, J = 4.6 Hz), 6.71(s, 1H), 7.48-7.52 (m, 3H, Ph—H), 7.59(s, 1H), 7.68(d, 1H, J = 5.6 Hz), 7.78(d, 1H, J = 5.8 Hz), 7.83-7.85 (m, 2H, Ph—H). |
| YJP-116 | 3'-Cl | 4-CH₃ | NH | 2.43(s, 3H, CH₃), 4.28(s, 5H, η⁵-C₅H₅), 4.31(t, 2H, J = 1.6 Hz), 4.55(t, 2H, J = 1.6 Hz), 5.50(s, 2H), 5.66(t, 1H, NH—CO—, J = 4.6 Hz), 6.71(s, 1H), 7.31(d, 2H, J = 6.4 Hz), |

TABLE 1-continued $^1$H NMR of the compounds of formula I

| No. | R$_1$ | (R$_2$)$_n$ | Z | $^1$H NMR (400 MHz, CDCl$_3$) |
|---|---|---|---|---|
| | | | | 7.59(s, 1H), 7.68(d, 1H, J = 5.6 Hz), 7.74(d, 2H, J = 8.0 Hz), 7.78(d, 1H, J = 5.8 Hz). |
| YJP-117 | 3'-Cl | 4-CH$_2$CH$_3$ | NH | 1.30(t, 3H, CH$_3$, J = 7.6 Hz), 2.74(q, 2H, CH$_2$CH$_3$, J = 8.0 Hz), 4.28(s, 5H, η$^5$-C$_5$H$_5$), 4.31(t, 2H, J = 2.0 Hz), 4.55(t, 2H, J = 2.0 Hz), 5.48(s, 2H), 5.66(t, 1H, NH—CO—, J = 4.6 Hz), 6.71(s, 1H), 7.32(d, 2H, J = 8.0 Hz), 7.59(s, 1H), 7.68(d, 1H, J = 5.6 Hz), 7.76(d, 2H, J = 8.4 Hz), 7.78(d, 1H, J = 5.8 Hz). |
| YJP-118 | 3'-Cl | 4-C(CH$_3$)$_3$ | NH | 1.38(s, 9H, 3CH$_3$), 4.28(s, 5H, η$^5$-C$_5$H$_5$), 4.31(t, 2H, J = 1.6 Hz), 4.55(t, 2H, J = 1.6 Hz), 5.50(s, 2H), 5.66(t, 1H, NH—CO—, J = 4.6 Hz), 6.71(s, 1H), 7.51(d, 2H, J = 8.4 Hz), 7.59(s, 1H), 7.68(d, 1H, J = 5.6 Hz), 7.78(d, 1H, J = 5.8 Hz), 7.81(d, 2H, J = 8.4 Hz). |
| YJP-119 | 3'-Cl | 2,4,6-TriCH$_3$ | NH | 2.18(s, 6H, 2CH$_3$), 2.35(s, 3H, CH$_3$), 4.28(s, 5H, η$^5$-C$_5$H$_5$), 4.31(t, 2H, J = 2.0 Hz), 4.56(t, 2H, J = 2.0 Hz), 5.54(s, 2H), 5.66(t, 1H, NH—CO—, J = 4.6 Hz), 6.36(s, 1H), 6.97(s, 1H), 7.29(s, 1H), 7.59(s, 1H), 7.68(d, 1H, J = 5.6 Hz), 7.78(d, 1H, J = 5.8 Hz). |
| YJP-120 | 3'-Cl | 4-OCH$_3$ | NH | 3.88(s, 3H, OCH$_3$), 4.28(s, 5H, η$^5$-C$_5$H$_5$), 4.31(t, 2H, J = 2.0 Hz), 4.55(t, 2H, J = 1.6 Hz), 5.48(s, 2H), 5.66(t, 1H, NH—CO—, J = 4.6 Hz), 6.68(s, 1H), 7.01(d, 2H, J = 7.2 Hz), 7.59(s, 1H), 7.68(d, 1H, J = 5.6 Hz), 7.78(d, 1H, J = 5.8 Hz), 7.81(d, 2H, J = 8.8 Hz). |
| YJP-121 | 3'-Cl | 3-OCH$_3$ | NH | 3.94(s, 3H, OCH$_3$), 4.28(s, 5H, η$^5$-C$_5$H$_5$), 4.31(t, 2H, J = 2.0 Hz), 4.56(t, 2H, J = 2.0 Hz), 5.50(s, 2H), 5.66(t, 1H, NH—CO—, J = 4.6 Hz), 6.94(s, 1H), 7.02-7.09(m, 2H), 7.43-7.48(m, 1H), 7.59(s, 1H), 7.68(d, 1H, J = 5.6 Hz), 7.78(d, 1H, J = 5.8 Hz), 7.93(dd, 1H, J = 1.6, 2.0 Hz). |
| YJP-122 | 3'-Cl | 2-OCH$_3$ | NH | 3.89(s, 3H, OCH$_3$), 4.28(s, 5H, η$^5$-C$_5$H$_5$), 4.31(t, 2H, J = 2.0 Hz), 4.55(t, 2H, J = 2.0 Hz), 5.51(s, 2H), 5.66(t, 1H, NH—CO—, J = 4.6 Hz), 6.72(s, 1H), 7.01-7.04(m, 1H), 7.39-7.41(m, 1H), 7.59(s, 1H), 7.68(d, 1H, J = 5.6 Hz), 7.78(d, 1H, J = 5.8 Hz). |
| YJP-123 | 3'-Cl | 4-F | NH | 4.27(s, 5H, η$^5$-C$_5$H$_5$), 4.31(t, 2H, J = 2.0 Hz), 4.55(t, 2H, J = 2.0 Hz), 5.51(s, 2H), 5.66(t, 1H, NH—CO—, J = 4.6 Hz), 6.70(s, 1H), 7.18(d, 2H, J = 8.4 Hz), 7.59(s, 1H), 7.68(d, 1H, J = 5.6 Hz), 7.78(d, 1H, J = 5.8 Hz), 7.82(d, 2H, J = 8.8 Hz). |
| YJP-124 | 3'-Cl | 2-F | NH | 4.28(s, 5H, η$^5$-C$_5$H$_5$), 4.31(t, 2H, J = 2.0 Hz), 4.56(t, 2H, J = 2.0 Hz), 5.52(s, 2H), 5.66(t, 1H, NH—CO—, J = 4.6 Hz), 6.87(s, 1H), 7.20-7.29(m, 3H), 7.44-7.49(m, 1H), 7.59(s, 1H), 7.68(d, 1H, J = 5.6 Hz), 7.78(d, 1H, J = 5.8 Hz). |
| YJP-125 | 3'-Cl | 4-Cl | NH | 4.28(s, 5H, η$^5$-C$_5$H$_5$), 4.31(t, 2H, J = 1.6 Hz), 4.56(t, 2H, J = 2.0 Hz), 5.51(s, 2H), 5.66(t, 1H, NH—CO—, J = 4.6 Hz), 6.71(s, 1H), 7.47(d, 2H, J = 8.4 Hz), 7.59(s, 1H), 7.68(d, 1H, J = 5.6 Hz), 7.78(d, 1H, J = 5.8 Hz), 7.82(d, 2H, J = 8.4 Hz). |
| YJP-126 | 3'-Cl | 2-Cl | NH | 4.28(s, 5H, η$^5$-C$_5$H$_5$), 4.31(t, 2H, J = 2.0 Hz), 4.55(t, 2H, J = 2.0 Hz), 5.53(s, 2H), 5.66(t, 1H, NH—CO—, J = 4.6 Hz), 6.90(s, 1H), 7.37-7.45(m, 2H), 7.53(dd, 1H, J = 1.2, 1.6 Hz), 7.59(s, 1H), 7.68(d, 1H, J = 5.6 Hz), 7.78(d, 1H, J = 5.8 Hz), 7.79-7.81(m, 1H). |
| YJP-127 | 3'-Cl | 2,4-DiCl | NH | 4.28(s, 5H, η$^5$-C$_5$H$_5$), 4.31(t, 2H, J = 2.0 Hz), 4.55(t, 2H, J = 2.0 Hz), 5.52(s, 2H), 5.66(t, 1H, NH—CO—, J = 4.6 Hz), 6.90(s, 1H), 7.38(dd, 1H, J = 2.0, 2.0 Hz), 7.55(d, 1H, J = 2.0 Hz), 7.59(s, 1H), 7.68(d, 1H, J = 5.6 Hz), 7.74(d, 1H, J = 8.4 Hz), 7.78(d, 1H, J = 5.8 Hz). |
| YJP-128 | 3'-Cl | 4-Br | NH | 4.28(s, 5H, η$^5$-C$_5$H$_5$), 4.31(t, 2H, J = 1.6 Hz), 4.56(t, 2H, J = 2.0 Hz), 5.51(s, 2H), 5.66(t, 1H, NH—CO—, J = 4.6 Hz), 6.71(s, 1H), 7.47(d, 2H, J = 8.4 Hz), 7.59(s, 1H), 7.68(d, 1H, J = 5.6 Hz), 7.78(d, 1H, J = 5.8 Hz), 7.79(d, 2H, J = 8.4 Hz). |
| YJP-129 | 3'-Cl | 2-Br | NH | 4.28(s, 5H, η$^5$-C$_5$H$_5$), 4.31(t, 2H, J = 2.0 Hz), 4.56(t, 2H, J = 2.0 Hz), 5.52(s, 2H), 5.66(t, 1H, NH—CO—, J = 4.6 Hz), 6.86(s, 1H), 7.21(ddd, 1H, J = 0.8, 0.8, 1.2 Hz), 7.24(dd, 1H, J = 0.8, 1.2 Hz), 7.29(dd, 1H, J = 0.8, 1.2 Hz), 7.44-7.48(m, 1H), 7.59(s, 1H), 7.68(d, 1H, J = 5.6 Hz), 7.78(d, 1H, J = 5.8 Hz). |
| YJP-130 | 3'-Cl | 3-Br | NH | 4.28(s, 5H, η$^5$-C$_5$H$_5$), 4.31(t, 2H, J = 2.0 Hz), 4.55(t, 2H, J = 1.6 Hz), 5.53(s, 2H), 5.66(t, 1H, NH—CO—, J = 4.6 Hz), 6.64(s, 1H), 7.69(d, 2H, J = 8.4 Hz), 7.63-7.68(m, 3H), 7.59(s, 1H), 7.68(d, 1H, J = 5.6 Hz), 7.78(d, 1H, J = 5.8 Hz). |
| YJP-131 | 3'-Cl | 4-CF$_3$ | NH | 4.28(s, 5H, η$^5$-C$_5$H$_5$), 4.31(t, 2H, J = 1.6 Hz), 4.55(t, 2H, J = 1.6 Hz), 5.52(s, 2H), 5.66(t, 1H, NH—CO—, J = 4.6 Hz), |

TABLE 1-continued

¹H NMR of the compounds of formula I

| No. | R₁ | (R₂)ₙ | Z | ¹H NMR (400 MHz, CDCl₃) |
|---|---|---|---|---|
| | | | | 6.78(s, 1H), 7.59(s, 1H), 7.68(d, 1H, J = 5.6 Hz), 7.76(d, 2H, J = 8.0 Hz), 7.78(d, 1H, J = 5.8 Hz), 7.98(d, 2H, J = 8.4 Hz). |
| YJP-132 | 3'-Cl | 2-CF₃ | NH | 4.28(s, 5H, η⁵-C₅H₅), 4.31(t, 2H, J = 2.0 Hz), 4.55(t, 2H, J = 1.6 Hz), 5.53(s, 2H), 5.66(t, 1H, NH—CO—, J = 4.6 Hz), 6.64(s, 1H), 7.59(s, 1H), 7.68(d, 1H, J = 5.6 Hz), 7.63-7.68(m, 3H), 7.78(d, 1H, J = 5.8 Hz), 7.85(d, 1H, J = 7.6 Hz). |
| YJP-133 | 3'-Cl | 4-NO₂ | NH | 4.28(s, 5H, η⁵-C₅H₅), 4.31(t, 2H, J = 2.0 Hz), 4.55(t, 2H, J = 2.0 Hz), 5.53(s, 2H), 5.66(t, 1H, NH—CO—, J = 4.6 Hz), 6.81(s, 1H), 7.45(d, 2H, J = 8.4 Hz), 7.59(s, 1H), 7.68(d, 1H, J = 5.6 Hz), 7.78(d, 1H, J = 5.8 Hz), 8.36(d, 2H, J = 8.4 Hz). |
| YJP-134 | 3'-F | H | NH | 4.28(s, 5H, η⁵-C₅H₅), 4.31(t, 2H, J = 1.6 Hz), 4.55(t, 2H, J = 1.6 Hz), 5.50(s, 2H), 5.66(t, 1H, NH—CO—, J = 4.6 Hz), 6.71(s, 1H), 7.48-7.52 (m, 3H, Ph—H), 7.59(s, 1H), 7.68(d, 1H, J = 5.6 Hz), 7.78(d, 1H, J = 5.8 Hz), 7.83-7.85 (m, 2H, Ph—H). |
| YJP-135 | 3'-F | 4-CH₃ | NH | 2.43(s, 3H, CH₃), 4.28(s, 5H, η⁵-C₅H₅), 4.31(t, 2H, J = 1.6 Hz), 4.55(t, 2H, J = 1.6 Hz), 5.50(s, 2H), 5.66(t, 1H, NH—CO—, J = 4.6 Hz), 6.71(s, 1H), 7.31(d, 2H, J = 6.4 Hz), 7.59(s, 1H), 7.68(d, 1H, J = 5.6 Hz), 7.74(d, 2H, J = 8.0 Hz), 7.78(d, 1H, J = 5.8 Hz). |
| YJP-136 | 3'-F | 4-CH₂CH₃ | NH | 1.30(t, 3H, CH₃, J = 7.6 Hz), 2.74(q, 2H, CH₂CH₃, J = 8.0 Hz), 4.28(s, 5H, η⁵-C₅H₅), 4.31(t, 2H, J = 2.0 Hz), 4.55(t, 2H, J = 2.0 Hz), 5.48(s, 2H), 5.66(t, 1H, NH—CO—, J = 4.6 Hz), 6.71(s, 1H), 7.32(d, 2H, J = 8.0 Hz), 7.59(s, 1H), 7.68(d, 1H, J = 5.6 Hz), 7.76(d, 2H, J = 8.4 Hz), 7.78(d, 1H, J = 5.8 Hz). |
| YJP-137 | 3'-F | 4-C(CH₃)₃ | NH | 1.38(s, 9H, 3CH₃), 4.28(s, 5H, η⁵-C₅H₅), 4.31(t, 2H, J = 1.6 Hz), 4.55(t, 2H, J = 1.6 Hz), 5.50(s, 2H), 5.66(t, 1H, NH—CO—, J = 4.6 Hz), 6.71(s, 1H), 7.51(d, 2H, J = 8.4 Hz), 7.59(s, 1H), 7.68(d, 1H, J = 5.6 Hz), 7.78(d, 1H, J = 5.8 Hz), 7.81(d, 2H, J = 8.4 Hz). |
| YJP-138 | 3'-F | 2,4,6-TriCH₃ | NH | 2.18(s, 6H, 2CH₃), 2.35(s, 3H, CH₃), 4.28(s, 5H, η⁵-C₅H₅), 4.31(t, 2H, J = 2.0 Hz), 4.56(t, 2H, J = 2.0 Hz), 5.54(s, 2H), 5.66(t, 1H, NH—CO—, J = 4.6 Hz), 6.36(s, 1H), 6.97(s, 1H), 7.29(s, 1H), 7.59(s, 1H), 7.68(d, 1H, J = 5.6 Hz), 7.78(d, 1H, J = 5.8 Hz). |
| YJP-139 | 3'-F | 4-OCH₃ | NH | 3.88(s, 3H, OCH₃), 4.28(s, 5H, η⁵-C₅H₅), 4.31(t, 2H, J = 2.0 Hz), 4.55(t, 2H, J = 1.6 Hz), 5.48(s, 2H), 5.66(t, 1H, NH—CO—, J = 4.6 Hz), 6.68(s, 1H), 7.01(d, 2H, J = 7.2 Hz), 7.59(s, 1H), 7.68(d, 1H, J = 5.6 Hz), 7.78(d, 1H, J = 5.8 Hz), 7.81(d, 2H, J = 8.8 Hz). |
| YJP-140 | 3'-F | 2-OCH₃ | NH | 3.94(s, 3H, OCH₃), 4.28(s, 5H, η⁵-C₅H₅), 4.31(t, 2H, J = 2.0 Hz), 4.56(t, 2H, J = 2.0 Hz), 5.50(s, 2H), 5.66(t, 1H, NH—CO—, J = 4.6 Hz), 6.94(s, 1H), 7.02-7.09(m, 2H), 7.43-7.48(m, 1H), 7.59(s, 1H), 7.68(d, 1H, J = 5.6 Hz), 7.78(d, 1H, J = 5.8 Hz), 7.93(dd, 1H, J = 1.6, 2.0 Hz). |
| YJP-141 | 3'-F | 3-OCH₃ | NH | 3.89(s, 3H, OCH₃), 4.28(s, 5H, η⁵-C₅H₅), 4.31(t, 2H, J = 2.0 Hz), 4.55(t, 2H, J = 2.0 Hz), 5.51(s, 2H), 5.66(t, 1H, NH—CO—, J = 4.6 Hz), 6.72(s, 1H), 7.01-7.04(m, 1H), 7.39-7.41(m, 1H), 7.59(s, 1H), 7.68(d, 1H, J = 5.6 Hz), 7.78(d, 1H, J = 5.8 Hz). |
| YJP-142 | 3'-F | 4-F | NH | 4.27(s, 5H, η⁵-C₅H₅), 4.31(t, 2H, J = 2.0 Hz), 4.55(t, 2H, J = 2.0 Hz), 5.51(s, 2H), 5.66(t, 1H, NH—CO—, J = 4.6 Hz), 6.70(s, 1H), 7.18(d, 2H, J = 8.4 Hz), 7.59(s, 1H), 7.68(d, 1H, J = 5.6 Hz), 7.78(d, 1H, J = 5.8 Hz), 7.82(d, 2H, J = 8.8 Hz). |
| YJP-143 | 3'-F | 2-F | NH | 4.28(s, 5H, η⁵-C₅H₅), 4.31(t, 2H, J = 2.0 Hz), 4.56(t, 2H, J = 2.0 Hz), 5.52(s, 2H), 5.66(t, 1H, NH—CO—, J = 4.6 Hz), 6.87(s, 1H), 7.20-7.29(m, 3H), 7.44-7.49(m, 1H), 7.59(s, 1H), 7.68(d, 1H, J = 5.6 Hz), 7.78(d, 1H, J = 5.8 Hz). |
| YJP-144 | 3'-F | 4-Cl | NH | 4.28(s, 5H, η⁵-C₅H₅), 4.31(t, 2H, J = 1.6 Hz), 4.56(t, 2H, J = 2.0 Hz), 5.51(s, 2H), 5.66(t, 1H, NH—CO—, J = 4.6 Hz), 6.71(s, 1H), 7.47(d, 2H, J = 8.4 Hz), 7.59(s, 1H), 7.68(d, 1H, J = 5.6 Hz), 7.78(d, 1H, J = 5.8 Hz), 7.82(d, 2H, J = 8.4 Hz). |
| YJP-145 | 3'-F | 2-Cl | NH | 4.28(s, 5H, η⁵-C₅H₅), 4.31(t, 2H, J = 2.0 Hz), 4.55(t, 2H, J = 2.0 Hz), 5.53(s, 2H), 5.66(t, 1H, NH—CO—, J = 4.6 Hz), 6.90(s, 1H), 7.37-7.45(m, 2H), 7.53(dd, 1H, J = 1.2, 1.6 Hz), 7.59(s, 1H), 7.68(d, 1H, J = 5.6 Hz), 7.78(d, 1H, J = 5.8 Hz), 7.79-7.81(m, 1H). |
| YJP-146 | 3'-F | 2,4-DiCl | NH | 4.28(s, 5H, η⁵-C₅H₅), 4.31(t, 2H, J = 2.0 Hz), 4.55(t, 2H, J = 2.0 Hz), 5.52(s, 2H), 5.66(t, 1H, NH—CO—, J = 4.6 Hz), |

TABLE 1-continued

¹H NMR of the compounds of formula I

| No. | R₁ | (R₂)ₙ | Z | ¹H NMR (400 MHz, CDCl₃) |
|---|---|---|---|---|
| | | | | 6.90(s, 1H), 7.38(dd, 1H, J = 2.0, 2.0 Hz), 7.55(d, 1H, J = 2.0 Hz), 7.59(s, 1H), 7.68(d, 1H, J = 5.6 Hz), 7.74(d, 1H, J = 8.4 Hz), 7.78(d, 1H, J = 5.8 Hz). |
| YJP-147 | 3'-F | 4-Br | NH | 4.28(s, 5H, η⁵-C₅H₅), 4.31(t, 2H, J = 1.6 Hz), 4.56(t, 2H, J = 2.0 Hz), 5.51(s, 2H), 5.66(t, 1H, NH—CO—, J = 4.6 Hz), 6.71(s, 1H), 7.47(d, 2H, J = 8.4 Hz), 7.59(s, 1H), 7.68(d, 1H, J = 5.6 Hz), 7.78(d, 1H, J = 5.8 Hz), 7.79(d, 2H, J = 8.4 Hz). |
| YJP-148 | 3'-F | 2-Br | NH | 4.28(s, 5H, η⁵-C₅H₅), 4.31(t, 2H, J = 2.0 Hz), 4.56(t, 2H, J = 2.0 Hz), 5.52(s, 2H), 5.66(t, 1H, NH—CO—, J = 4.6 Hz), 6.86(s, 1H), 7.21(ddd, 1H, J = 0.8, 0.8, 1.2 Hz), 7.24(dd, 1H, J = 0.8, 1.2 Hz), 7.29(dd, 1H, J = 0.8, 1.2 Hz), 7.44-7.48(m, 1H), 7.59(s, 1H), 7.68(d, 1H, J = 5.6 Hz), 7.78(d, 1H, J = 5.8 Hz). |
| YJP-149 | 3'-F | 3-Br | NH | 4.28(s, 5H, η⁵-C₅H₅), 4.31(t, 2H, J = 2.0 Hz), 4.55(t, 2H, J = 1.6 Hz), 5.53(s, 2H), 5.66(t, 1H, NH—CO—, J = 4.6 Hz), 6.64(s, 1H), 7.69(d, 2H, J = 8.4 Hz), 7.63-7.68(m, 3H), 7.59(s, 1H), 7.68(d, 1H, J = 5.6 Hz), 7.78(d, 1H, J = 5.8 Hz). |
| YJP-150 | 3'-F | 4-CF₃ | NH | 4.28(s, 5H, η⁵-C₅H₅), 4.31(t, 2H, J = 1.6 Hz), 4.55(t, 2H, J = 1.6 Hz), 5.52(s, 2H), 5.66(t, 1H, NH—CO—, J = 4.6 Hz), 6.78(s, 1H), 7.59(s, 1H), 7.68(d, 1H, J = 5.6 Hz), 7.76(d, 2H, J = 8.0 Hz), 7.78(d, 1H, J = 5.8 Hz), 7.98(d, 2H, J = 8.4 Hz). |
| YJP-151 | 3'-F | 2-CF₃ | NH | 4.28(s, 5H, η⁵-C₅H₅), 4.31(t, 2H, J = 2.0 Hz), 4.55(t, 2H, J = 1.6 Hz), 5.53(s, 2H), 5.66(t, 1H, NH—CO—, J = 4.6 Hz), 6.64(s, 1H), 7.59(s, 1H), 7.68(d, 1H, J = 5.6 Hz), 7.63-7.68(m, 3H), 7.78(d, 1H, J = 5.8 Hz), 7.85(d, 1H, J = 7.6 Hz). |
| YJP-152 | 3'-F | 4-NO₂ | NH | 4.28(s, 5H, η⁵-C₅H₅), 4.31(t, 2H, J = 2.0 Hz), 4.55(t, 2H, J = 2.0 Hz), 5.53(s, 2H), 5.66(t, 1H, NH—CO—, J = 4.6 Hz), 6.81(s, 1H), 7.45(d, 2H, J = 8.4 Hz), 7.59(s, 1H), 7.68(d, 1H, J = 5.6 Hz), 7.78(d, 1H, J = 5.8 Hz), 8.36(d, 2H, J = 8.4 Hz). |

Example 5. In Vitro Anti-Tumor Activity Assay

The compounds in the above examples were tested for in vitro anti-tumor activity using the CCK-8 method. The in vitro inhibitory activity of the compounds against breast cancer cell line (MCF-7), lung adenocarcinoma cell line (A549) and cervical cancer cell line (Hela) were mainly studied in this example. The breast cancer cell line (MCF-7), the lung adenocarcinoma cell line (A549) and the cervical cancer cell line (Hela) were obtained from cell lines stored in Ningxia Medical University. The specific test process was illustrated by the process for testing the breast cancer MCF-7 cell line:

(1) Process for Incubating Breast Cancer Cell Line (MCF-7) and Testing Inhibitory Activities.

The breast cancer cell line MCF-7 was incubated in an incubator for 24 h under the condition (37° C., 5% $CO_2$, saturated humidity). When the cells were in logarithmic growth phase, the culture supernatant was removed, and the residue was digested with 0.25% trypsin-EDTA solution, and added with high glucose medium to terminate the digestion. The cells were seeded in a 96-well plate with a cell density of 5000 cells/well. The 96-well plate was incubated in an incubator for 24 h. Then the cell culture supernatant in the 96-well plate was removed. 100 μL of fresh high glucose medium was added to the 96-well plate, and samples at different concentrations were added to wells at 1 μL/well Subsequently, 1 μL solution of different concentrations were added to each well (every concentration was repeated for 5 times). After the plate was incubated for another 48 h at 37° C., 10 μL of CCK8 was added to each well, and the plate was then incubated at 37° C. for another 1-4 h. The absorbance of each well at 450 nm was measured on a multifunctional microplate reader. Inhibition rate %=[($OD_{control\ cells}$−$OD_{treatment\ cells}$)/($OD_{control\ cells}$−$OD_{blank}$)]×100. Negative control was a mixed solution of high glucose medium and DMSO at a ratio of $V_{high\ glucose\ medium}$ and $V_{DMSO}$=10:1.

(2) Process for Incubating Lung Adenocarcinoma Cell Line (A549) and Cervical Cancer Cell Line (Hela) and Testing Inhibitory Activities The experiment process for inhibiting the lung adenocarcinoma cell line (A549) and the cervical cancer cell line (Hela) was the same as the screening process of the breast cancer cell line (MCF-7). The results of activities of the preferred compounds for inhibiting breast cancer cell line MCF-7, human lung adenocarcinoma cell line A549 and cervical cancer cell line Hela are shown in the following Tables 2, 3 and 4 respectively.

TABLE 2

Test results of the activities of some example compounds of formula (I) for inhibiting breast cancer cell line MCF-7

| Compound no. | Concentration (μM) | Inhibition rate (%) |
|---|---|---|
| YJP-2 | 14.37 | 85.39 |
| YJP-3 | 10.68 | 91.74 |
| YJP-4 | 10.68 | 94.48 |
| YJP-6 | 16.05 | 77.46 |
| YJP-7 | 16.63 | 57.41 |
| YJP-8 | 19.34 | 80.48 |
| YJP-14 | 16.22 | 86.13 |
| YJP-18 | 11.35 | 88.12 |

TABLE 3

Test results of the activities of some example compounds of formula (I) for inhibiting human lung adenocarcinoma cell line A549

| Compound no. | Concentration (μM) | Inhibition rate (%) |
|---|---|---|
| YJP-14 | 16.22 | 57.00 |
| YJP-17 | 12.43 | 60.42 |
| YJP-18 | 11.35 | 79.29 |

TABLE 4

Test results of the activities of some example compounds of formula (I) for inhibiting cervical cancer cell line Hela

| Compound no. | Concentration (μM) | Inhibition rate (%) |
|---|---|---|
| YJP-4  | 10.68 | 60.10 |
| YJP-13 |  9.91 | 74.80 |
| YJP-14 | 16.22 | 68.26 |
| YJP-17 | 12.43 | 57.62 |
| YJP-18 | 11.35 | 63.99 |
| YJP-19 | 10.53 | 88.94 |

The examples of the present invention have been described above. However, the present invention is not limited to the above examples. Any modification, equivalent, improvement and the like made without departing from the spirit and principle of the present invention shall fall within the protection scope of the present invention.

The invention claimed is:

1. A ferrocene derivative of formula (I), a pharmaceutically acceptable salt thereof or a solvate thereof:

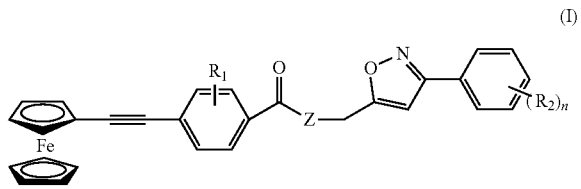

(I)

wherein Z is selected from NH, O and S;

$R_1$ is selected from hydrogen, methyl, F and Cl;

$R_2$ is independently selected from hydrogen, halogen, $C_1$-$C_6$ alkyl, $C_1$-$C_6$ alkoxy, $C_1$-$C_6$ haloalkoxy, $C_1$-$C_6$ haloalkyl and nitro; and n is an integer from 0 to 5.

2. The ferrocene derivative of formula (I), the pharmaceutically acceptable salt thereof or the solvate thereof according to claim 1, wherein $R_2$ is independently selected from fluoro, chloro, bromo, methyl, ethyl, methoxy, trifluoromethyl, tert-butyl, cyano and nitro; and n is 1, 2 or 3.

3. The ferrocene derivative of formula (I), the pharmaceutically acceptable salt thereof or the solvate thereof according to claim 1, wherein the ferrocene derivative of formula (I) is selected from the following compounds:

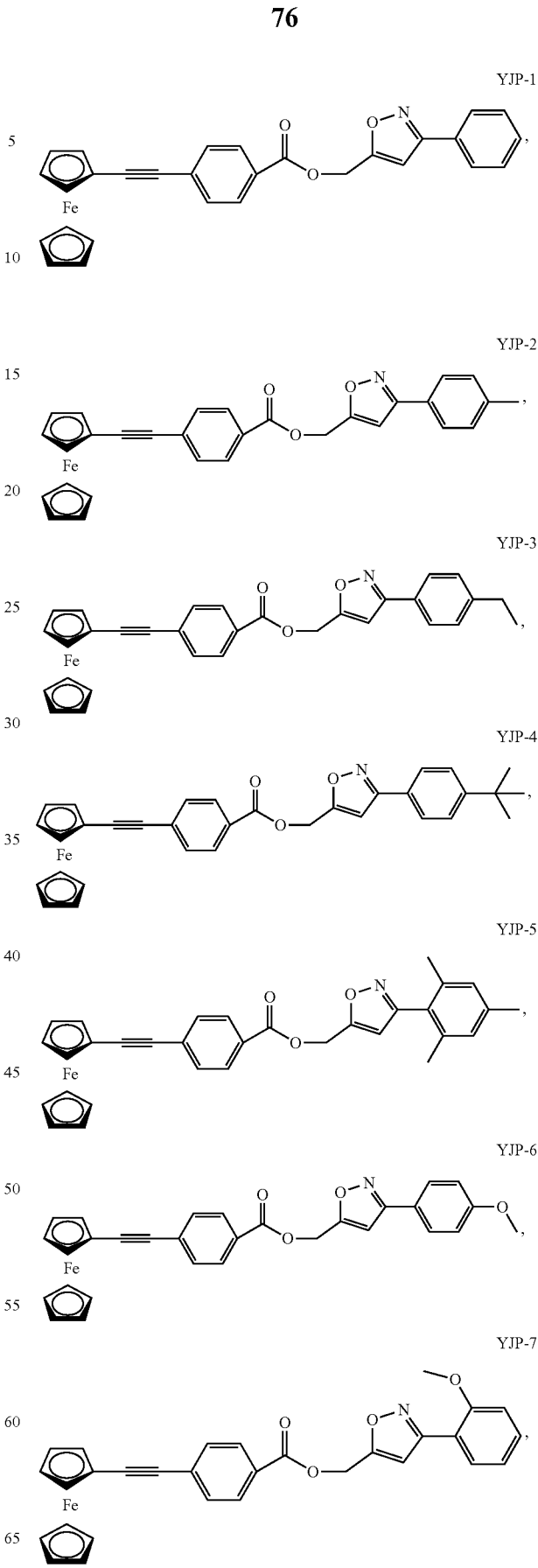

-continued
YJP-8
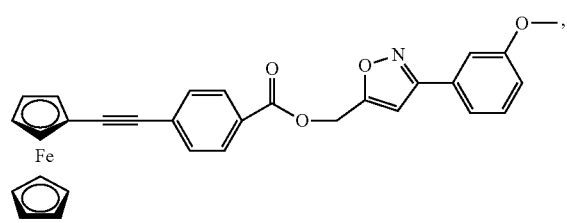
YJP-9
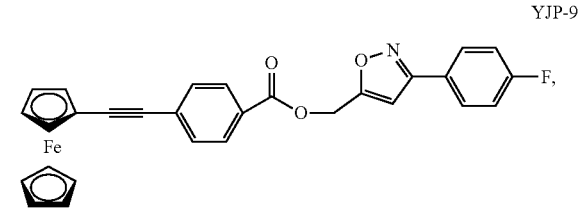
YJP-10
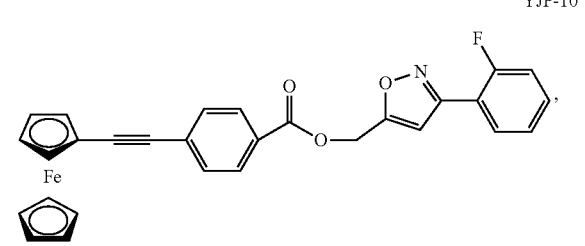
YJP-11
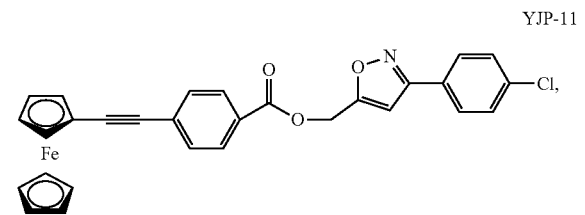
YJP-12
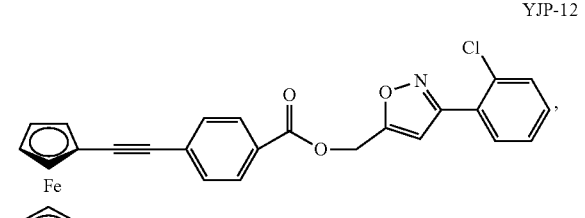
YJP-13
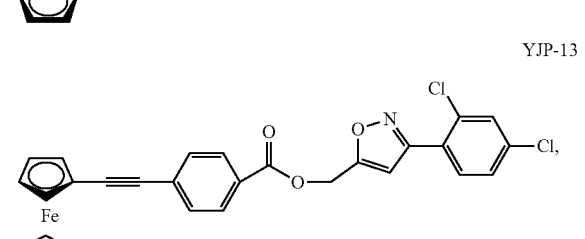
YJP-14
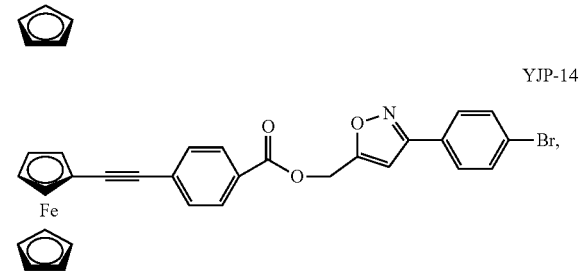
-continued
YJP-15
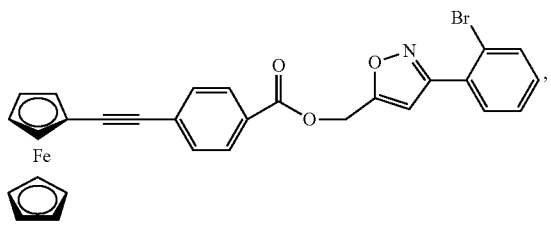
YJP-16
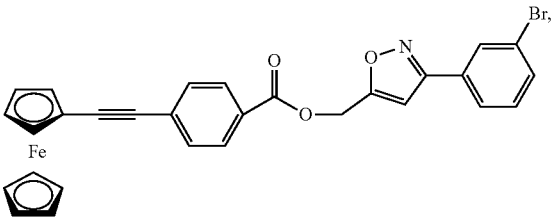
YJP-17
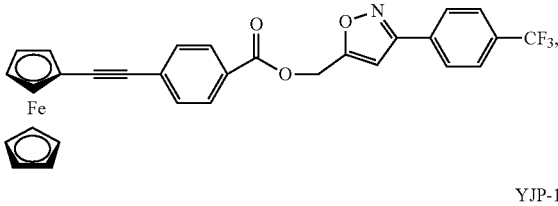
YJP-18
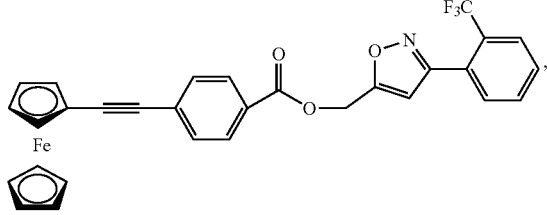
YJP-19
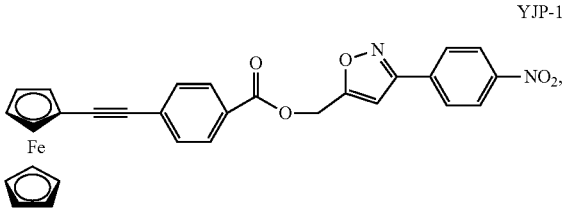
YJP-20
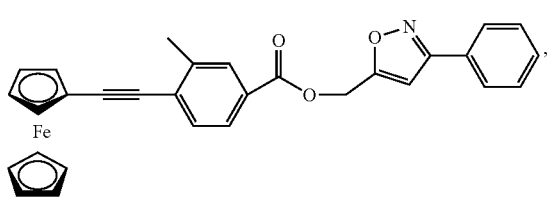
YJP-21

YJP-22
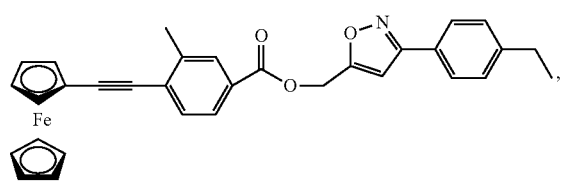
YJP-23
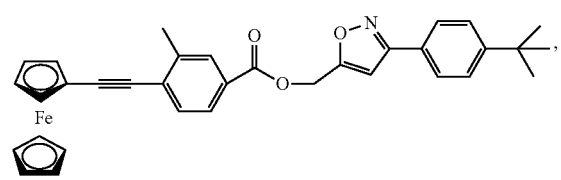
YJP-24
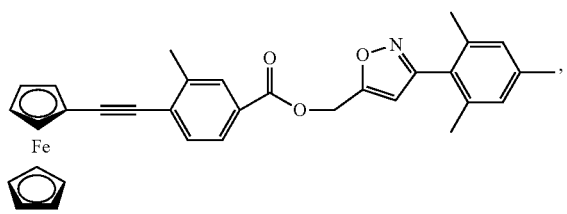
YJP-25
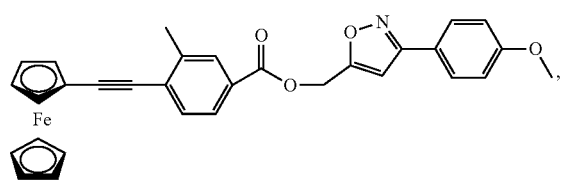
YJP-26
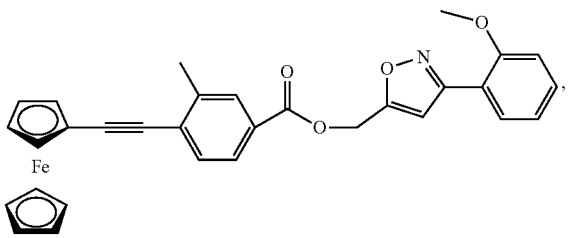
YJP-27
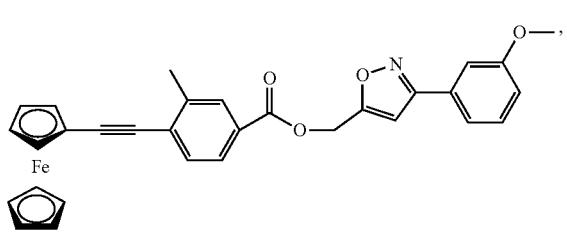
YJP-28
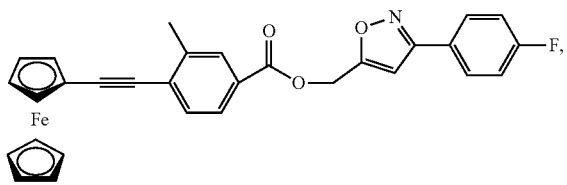
YJP-29
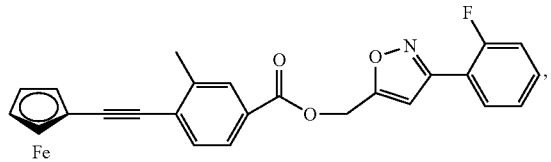
YJP-30
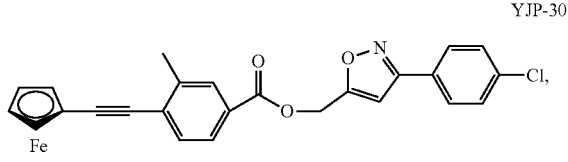
YJP-31
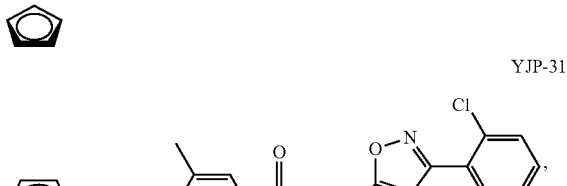
YJP-32
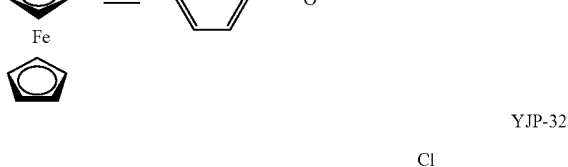
YJP-33
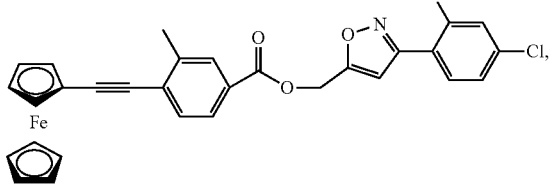
YJP-34
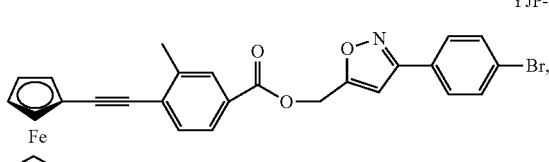
YJP-35
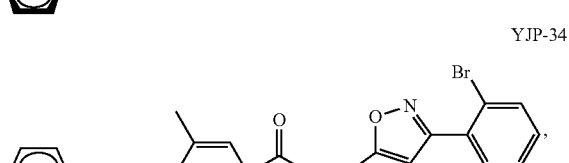

-continued
YJP-36
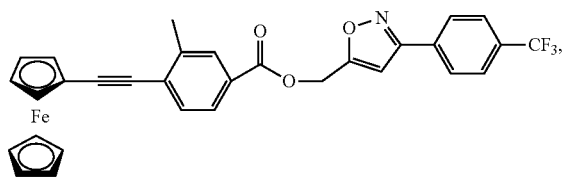
YJP-37
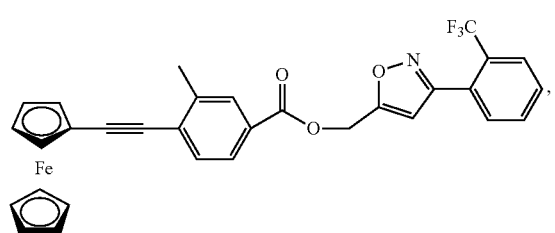
YJP-38
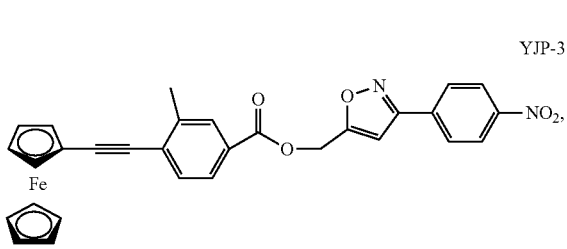
YJP-39
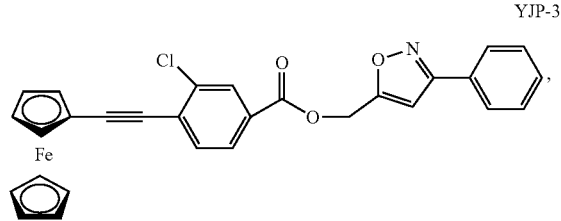
YJP-40
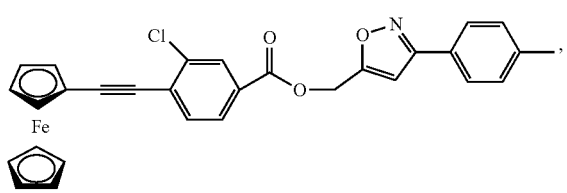
YJP-41
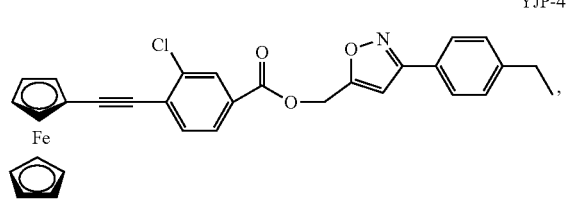
YJP-42
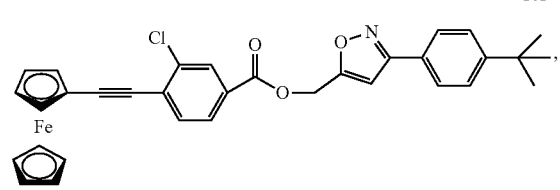
-continued
YJP-43
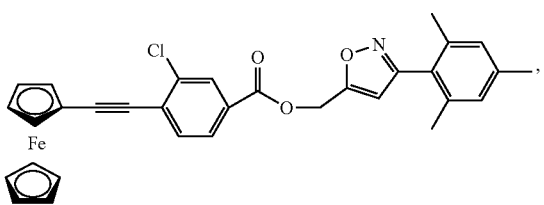
YJP-44
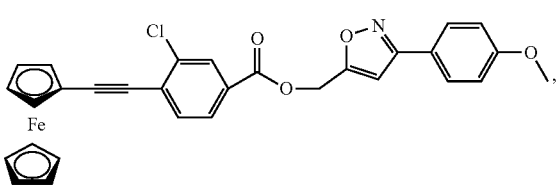
YJP-45
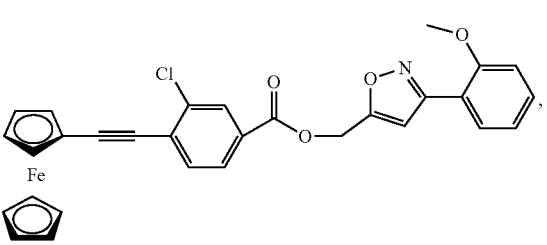
YJP-46
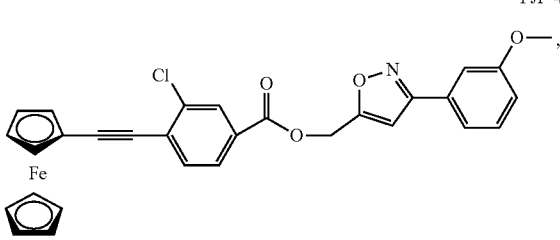
YJP-47
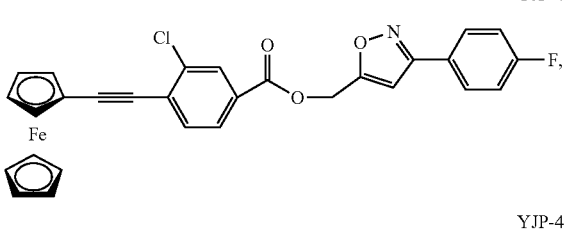
YJP-48
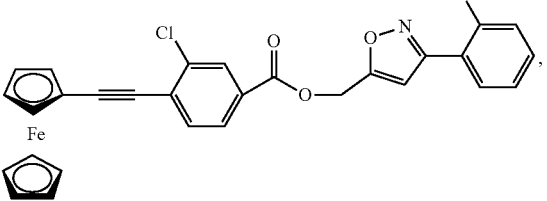
YJP-49
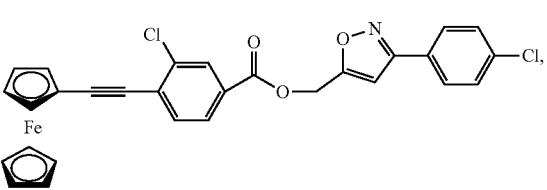

YJP-50
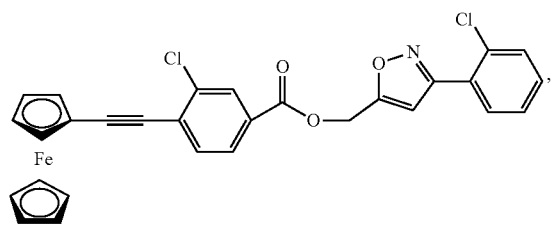
YJP-51
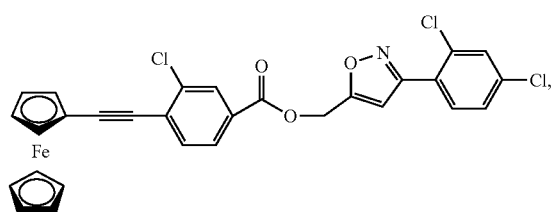
YJP-52
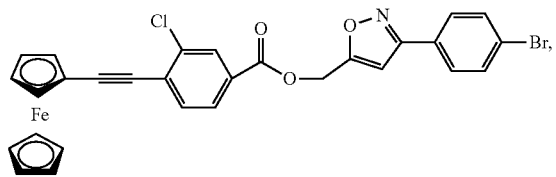
YJP-53
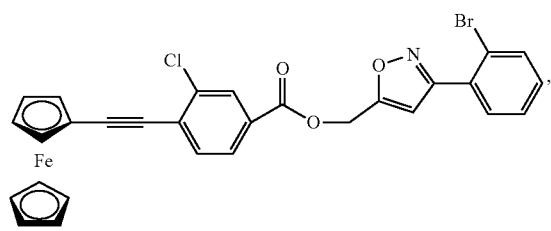
YJP-54
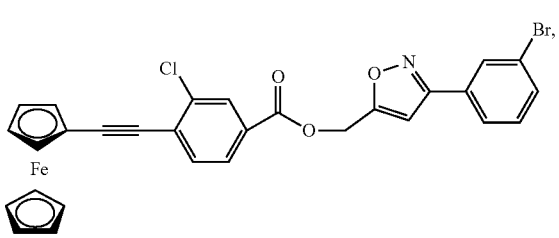
YJP-55
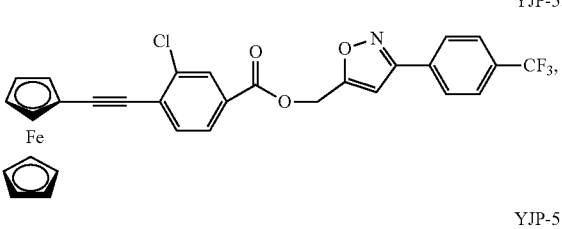
YJP-56
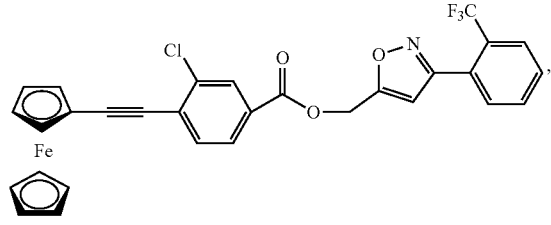
YJP-57
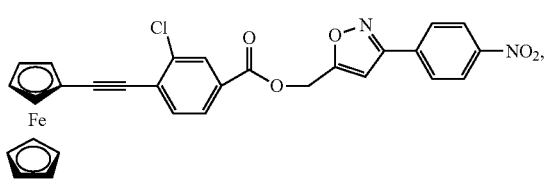
YJP-58
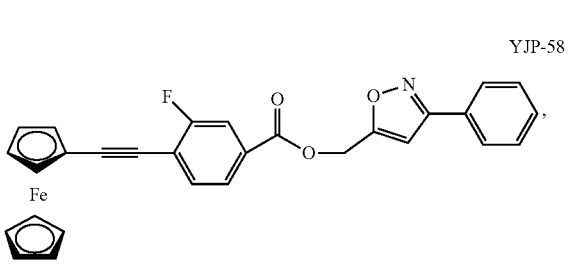
YJP-59
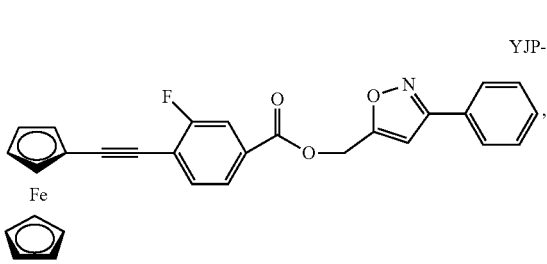
YJP-60
YJP-61
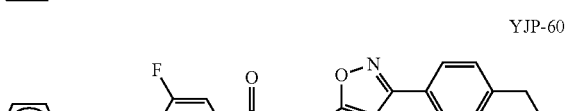
YJP-62
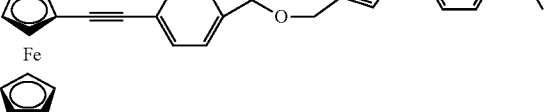
YJP-63
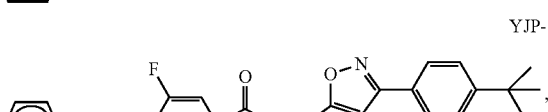

YJP-64
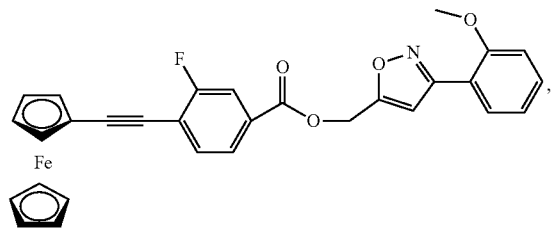
YJP-65
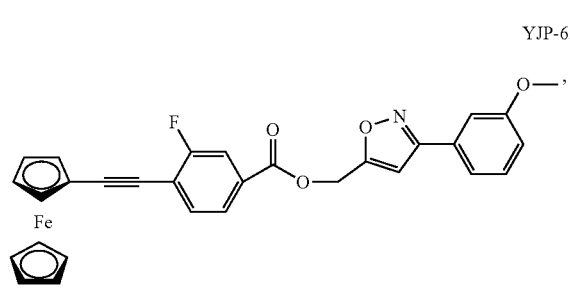
YJP-66
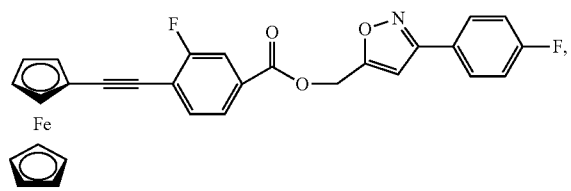
YJP-67
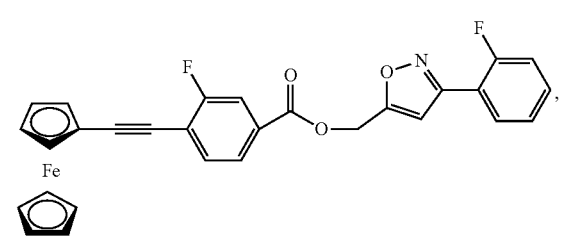
YJP-68
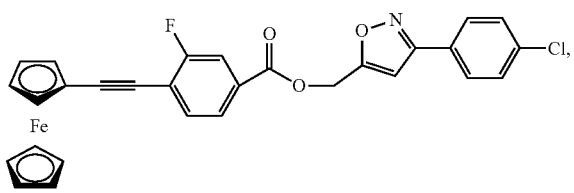
YJP-69
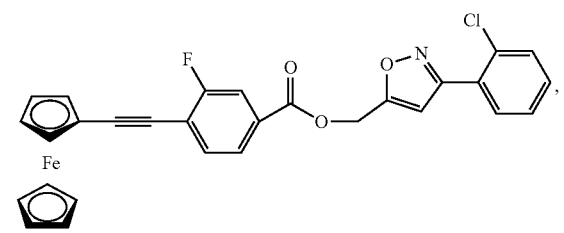
YJP-70
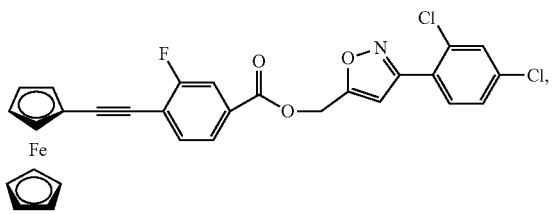
YJP-71
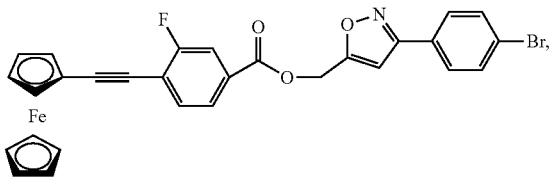
YJP-72
YJP-73
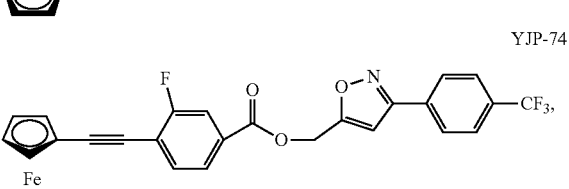
YJP-74
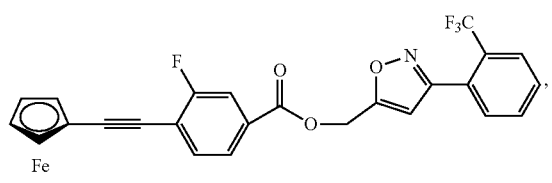
YJP-75
YJP-76
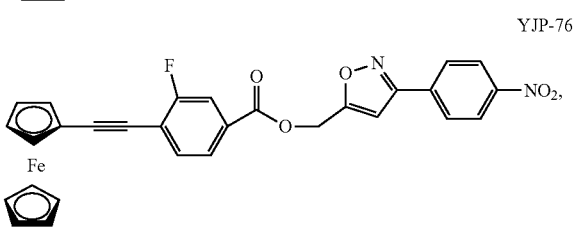

YJP-77
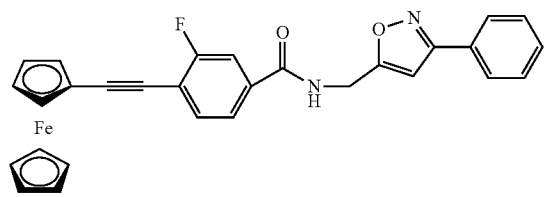
YJP-78
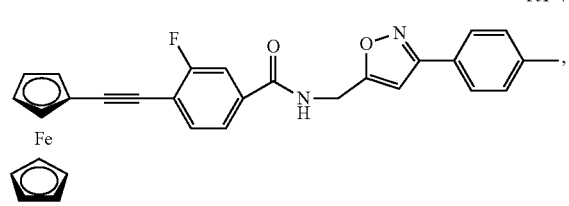
YJP-79
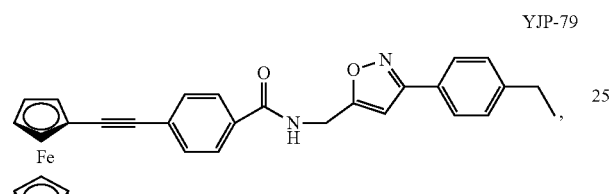
YJP-80
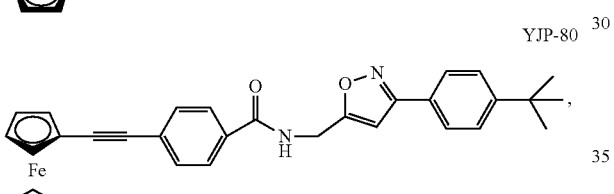
YJP-81
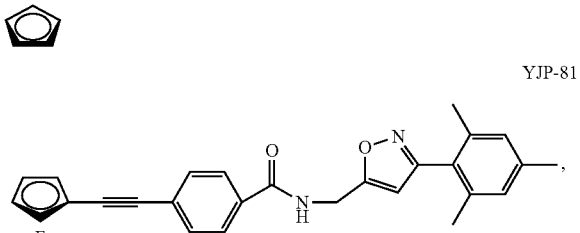
YJP-82
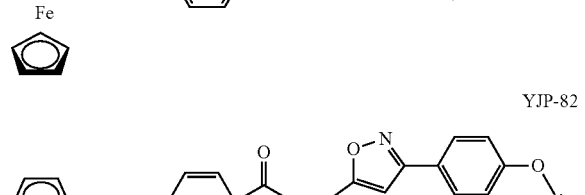
YJP-83
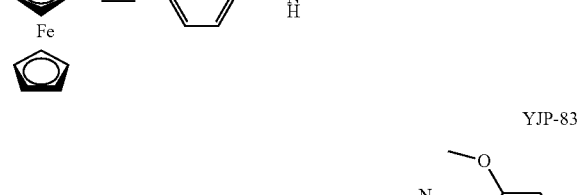
YJP-84
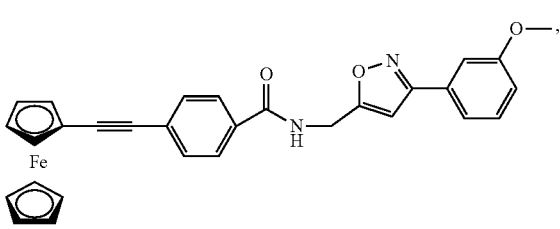
YJP-85
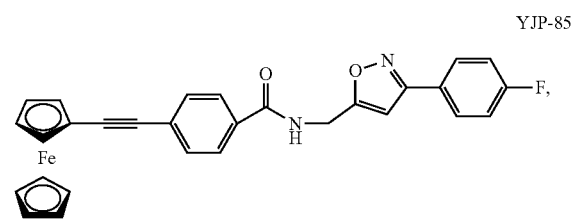
YJP-86
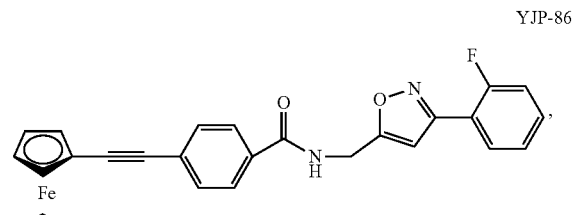
YJP-87
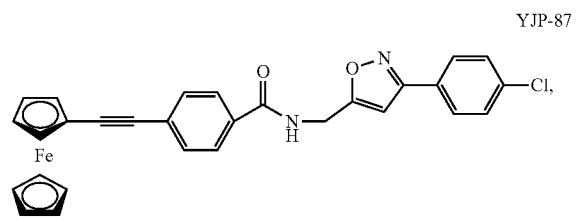
YJP-88
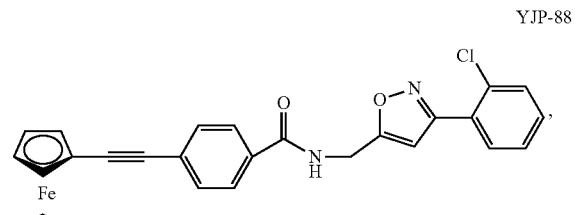
YJP-89
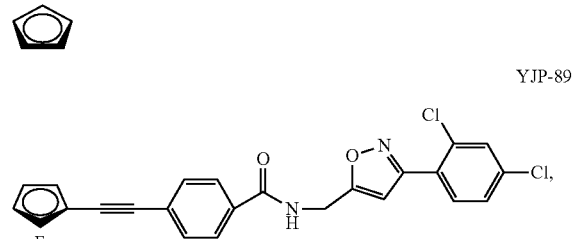
YJP-90
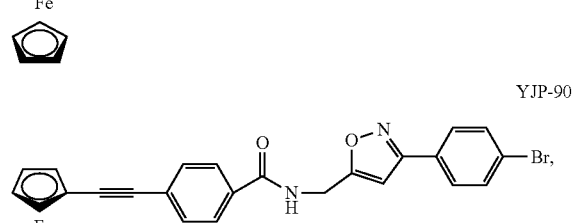

YJP-91
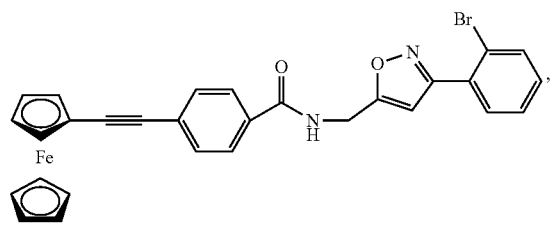
YJP-92
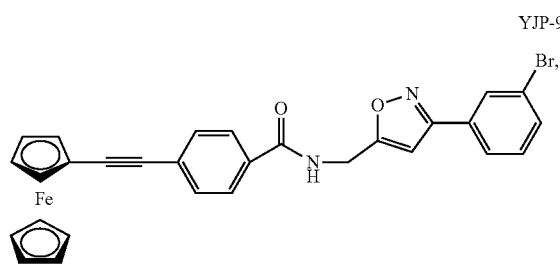
YJP-93
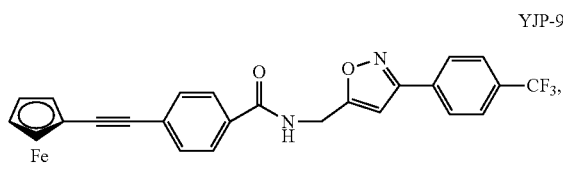
YJP-94
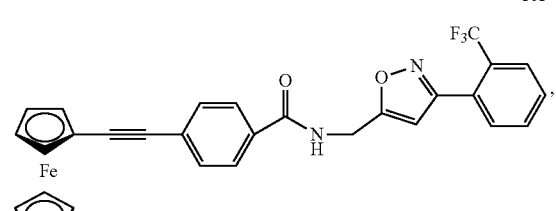
YJP-95
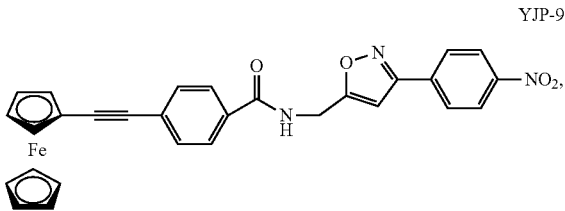
YJP-96
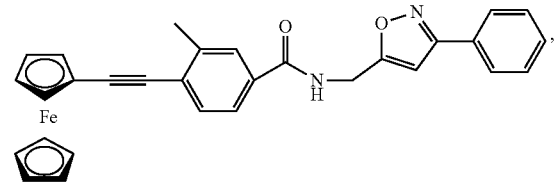
YJP-97
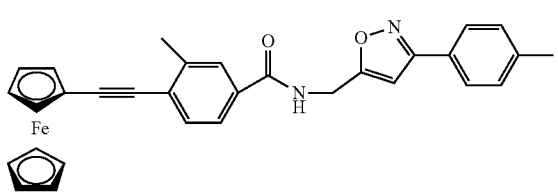
YJP-98
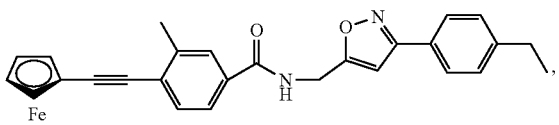
YJP-99
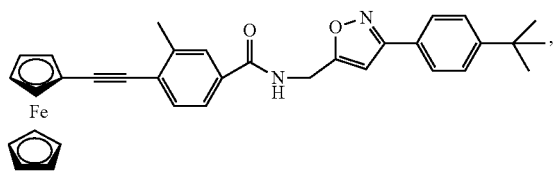
YJP-100
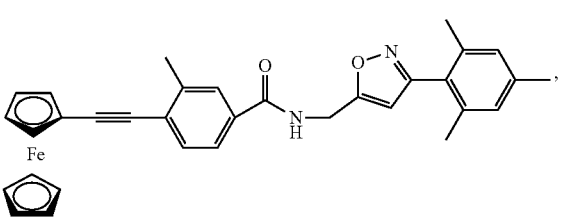
YJP-101
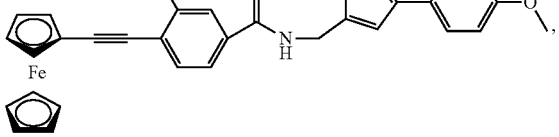
YJP-102
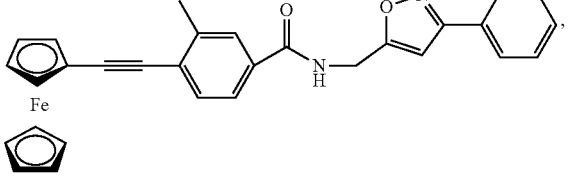
YJP-103
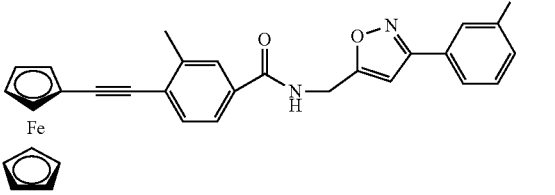
YJP-104
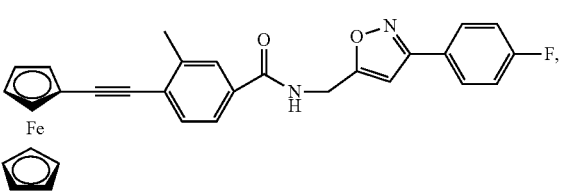

YJP-105
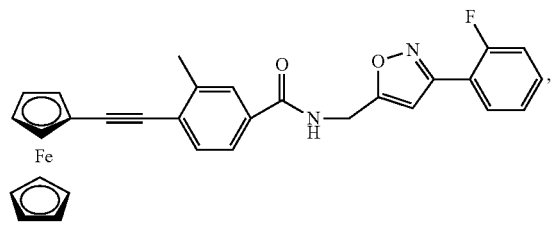
YJP-106
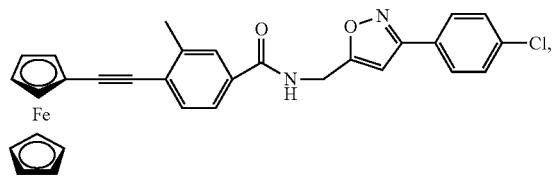
YJP-107
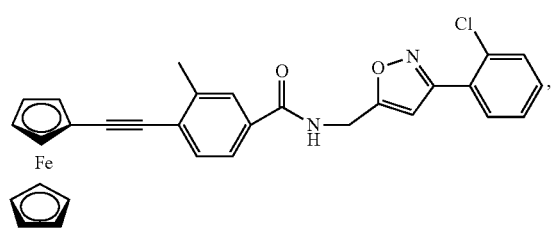
YJP-108
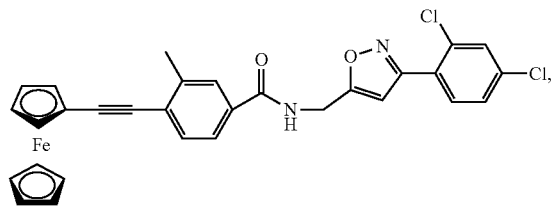
YJP-109
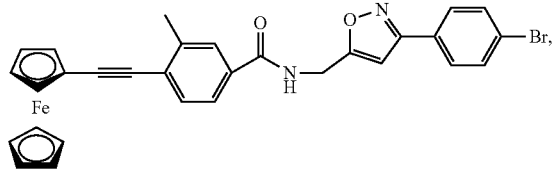
YJP-110
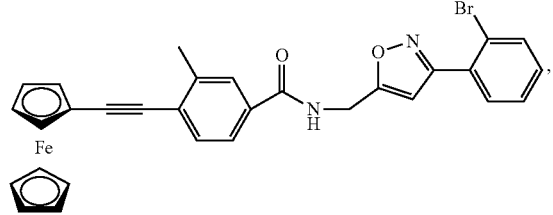
YJP-111
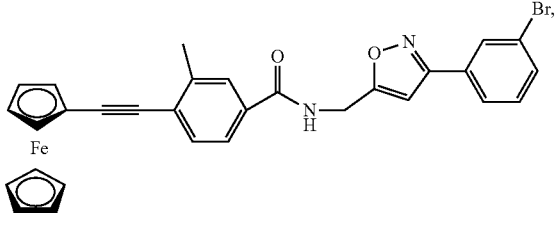
YJP-112
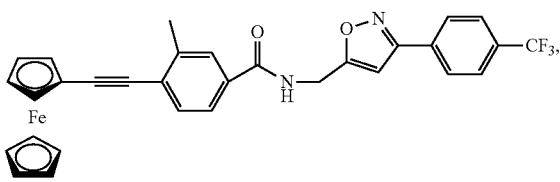
YJP-113
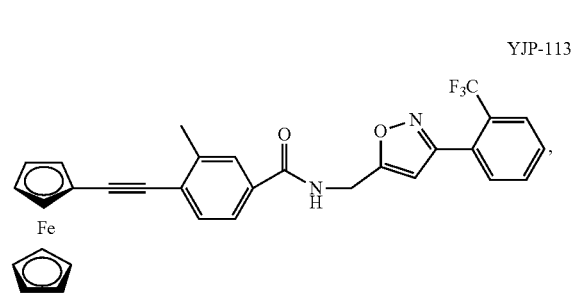
YJP-114
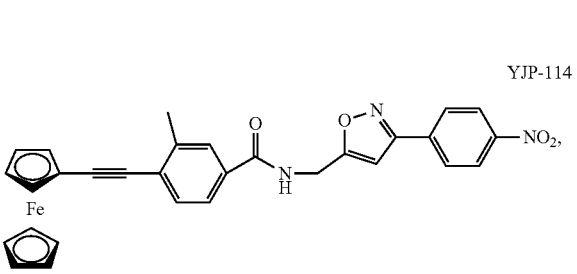
YJP-115
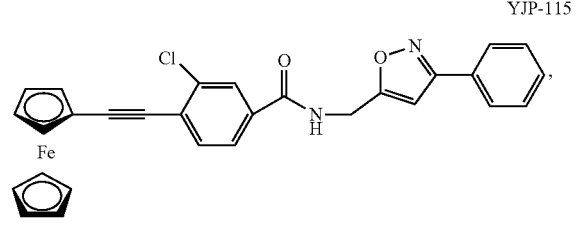
YJP-116
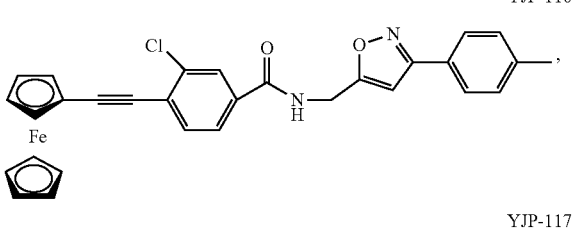
YJP-117
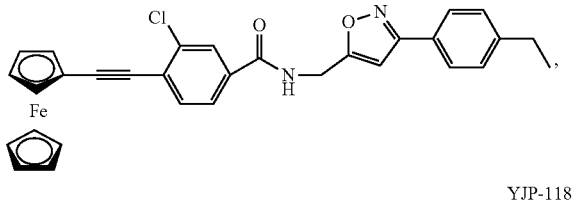
YJP-118
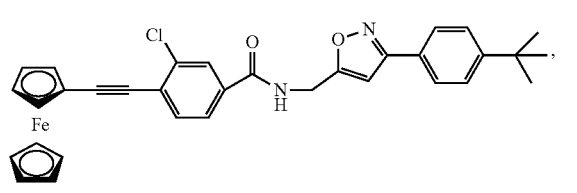

YJP-119
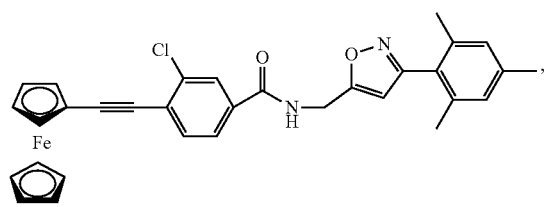
YJP-126
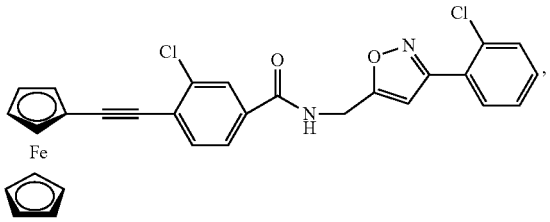
YJP-120
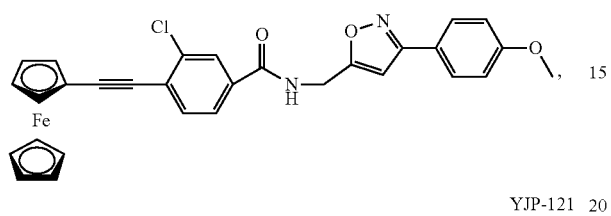
YJP-127
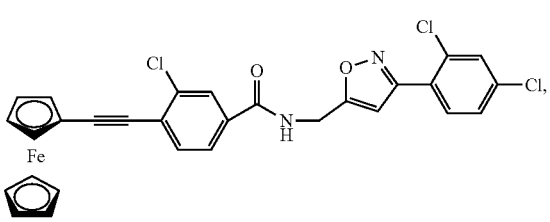
YJP-121
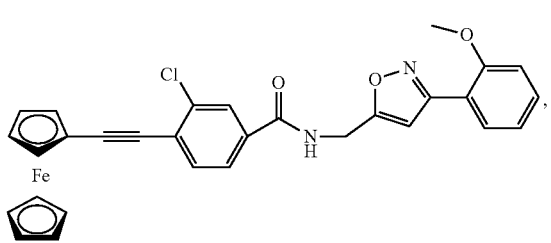
YJP-128
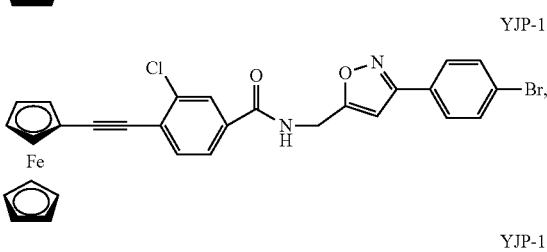
YJP-122
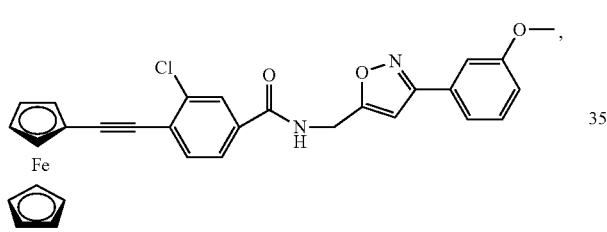
YJP-129
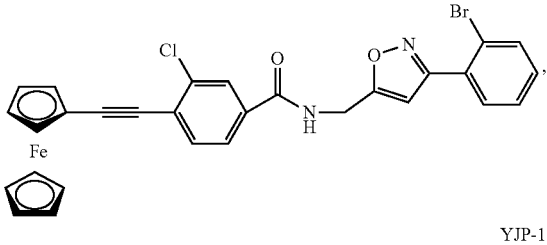
YJP-123
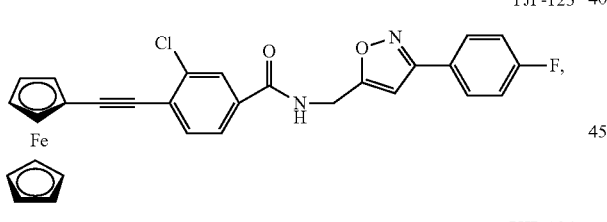
YJP-130
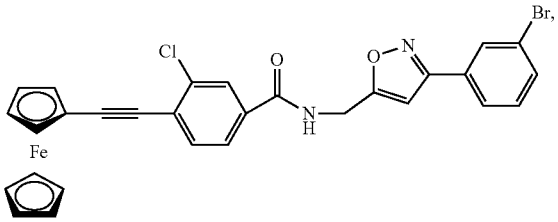
YJP-124
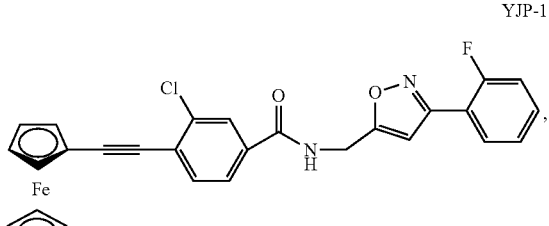
YJP-131
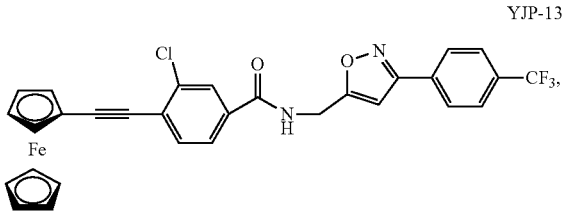
YJP-125
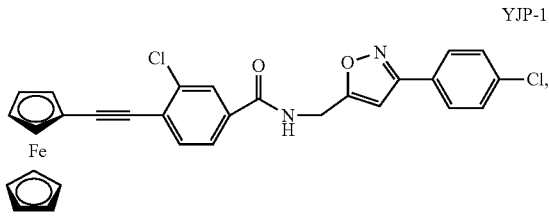
YJP-132
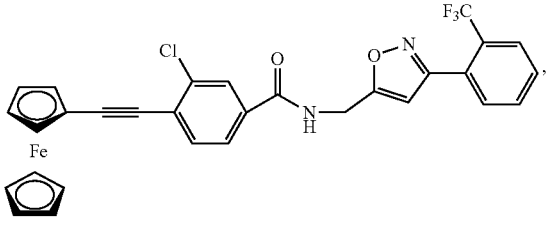

YJP-133
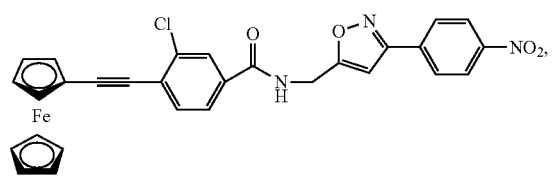
YJP-134
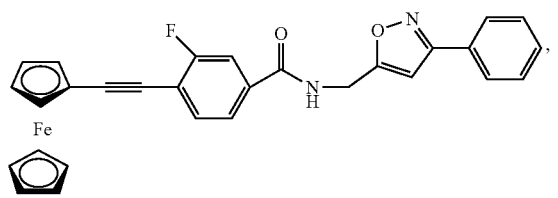
YJP-135
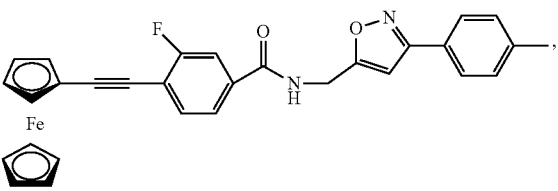
YJP-136
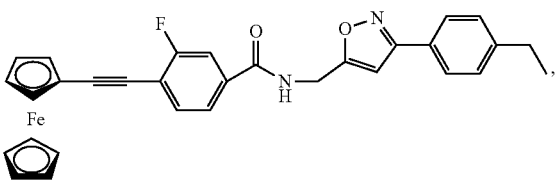
YJP-137
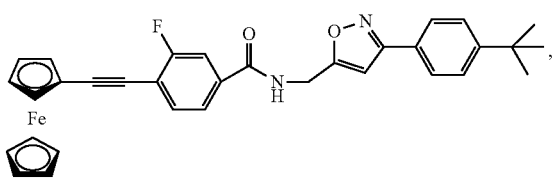
YJP-138
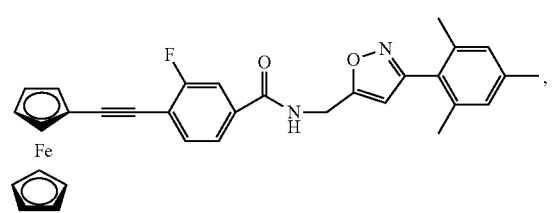
YJP-139
YJP-140
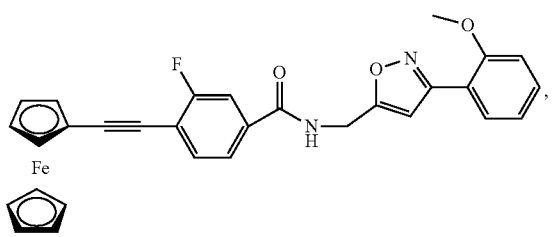
YJP-141
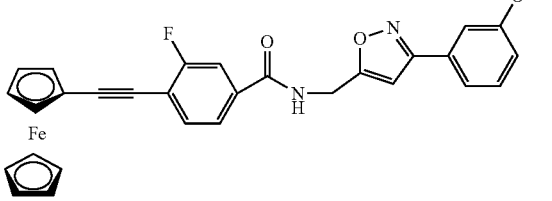
YJP-142
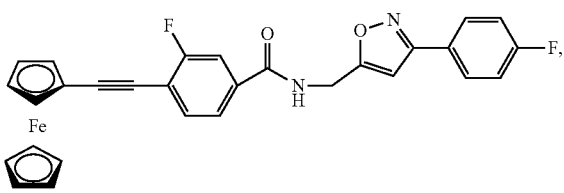
YJP-143
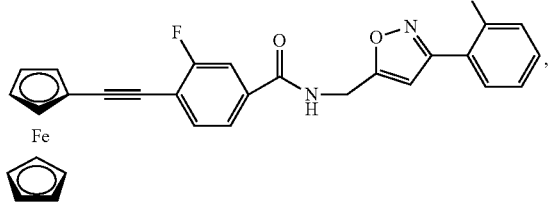
YJP-144
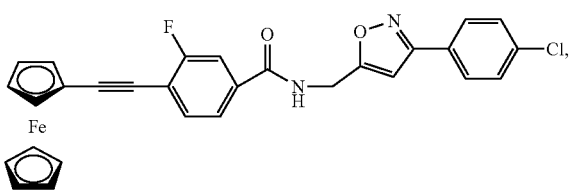
YJP-145
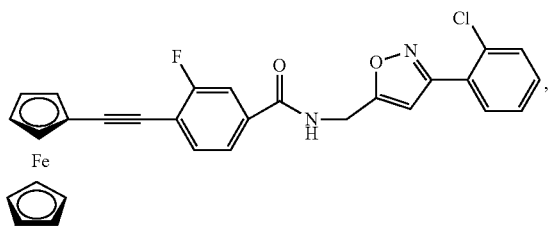

-continued

YJP-146
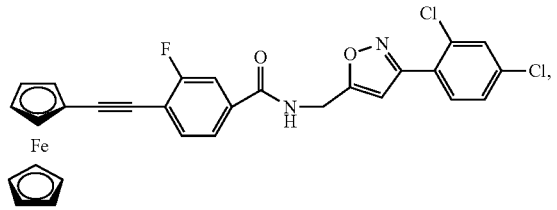

YJP-147
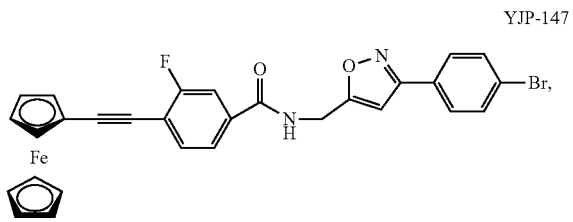

YJP-148
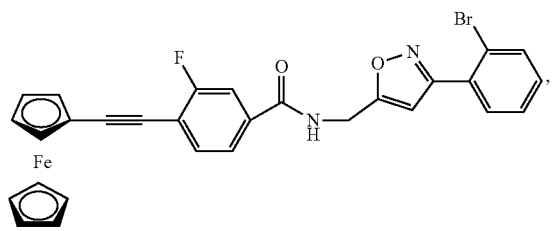

YJP-149
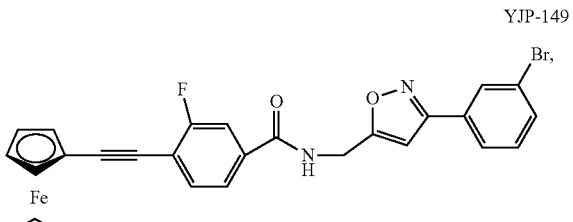

YJP-150
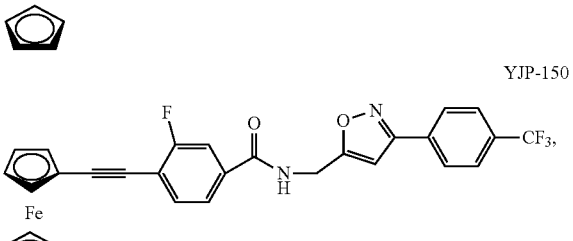

YJP-151
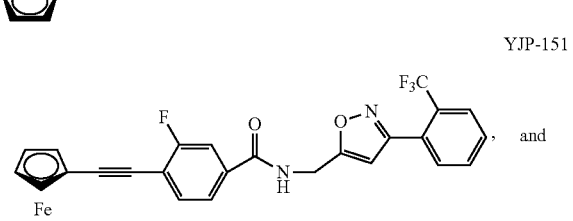
and

YJP-152
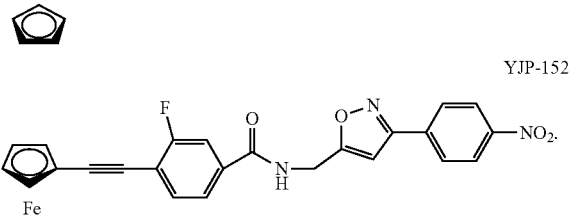

4. A preparation method for the ferrocene derivative of formula (I) according to claim 1, comprising the following steps:
  (1) reacting ferrocenylethyne with a compound of formula A to give a ferrocene-containing intermediate of formula B,
  wherein the compound of formula A is 3-($R_1$)-4-bromobenzoic acid with a structural formula of

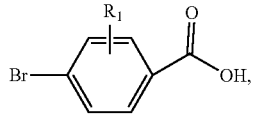
A and
the intermediate of formula B has a structural formula of

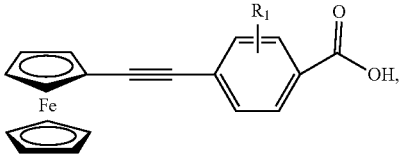
B wherein $R_1$ is defined as in claim 1;
  (2) reacting the intermediate of formula B with a compound of formula C to give the ferrocene derivative of formula (I),
  wherein the compound of formula C has a structural formula of

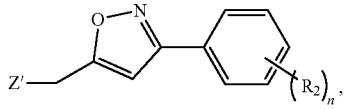
C and wherein $R_2$ and n are defined as in claim 1, and Z' represents $NH_2$, OH or SH.

5. The preparation method according to claim 4, wherein the compound of formula C is 3-substituted phenyl-5-hydroxymethyl-isoxazole (II), 3-substituted phenyl-5-mercaptomethyl-isoxazole, or 3-substituted phenyl-5-aminomethyl-isoxazole (III).

6. The preparation method according to claim 4, wherein the reaction in step (2) is carried out in the presence of a condensing agent.

7. A pharmaceutical composition comprising the ferrocene derivative of formula (I), the pharmaceutically acceptable salt thereof or the solvate thereof according to claim 1.

8. A pharmaceutical preparation comprising the ferrocene derivative of formula (I), the pharmaceutically acceptable salt thereof or the solvate thereof according to claim 1, wherein the pharmaceutical preparation is a solid oral preparation, a liquid oral preparation or an injection.

9. A method for treating breast cancer, lung adenocarcinoma, or cervical cancer, comprising administering to a patient the ferrocene derivative of formula (I), the pharmaceutically acceptable salt thereof or the solvate thereof according to claim 1.

10. A pharmaceutical composition comprising the ferrocene derivative of formula (I), the pharmaceutically acceptable salt thereof or the solvate thereof according to claim 2.

11. A pharmaceutical composition comprising the ferrocene derivative of formula (I), the pharmaceutically acceptable salt thereof or the solvate thereof according to claim 3.

12. A method for treating breast cancer, lung adenocarcinoma, or cervical cancer, comprising administering to a patient the ferrocene derivative of formula (I), the pharmaceutically acceptable salt thereof or the solvate thereof according to claim 2.

13. A method for treating breast cancer, lung adenocarcinoma, or cervical cancer, comprising administering to a patient the ferrocene derivative of formula (I), the pharmaceutically acceptable salt thereof or the solvate thereof according to claim 3.

14. The preparation method according to claim 4, wherein step (1) is carried out in the presence of a palladium(II) compound, an organophosphorus compound and a copper(I) compound in a dried organic solvent in the presence of an alkaline deacid reagent; and the alkaline deacid reagent is selected from organic bases and inorganic bases.

15. The preparation method according to claim 14, wherein the organic base is selected from triethylamine, tripropylamine, DMAP, DMF, N-methylmorpholine, and mixtures thereof, and the inorganic base is selected from potassium carbonate, sodium hydride, sodium carbonate, and mixtures thereof.

16. The preparation method according to claim 14, wherein step (1) comprises the dispersing ferrocenylethyne and the compound of formula A in a mixture of the dried organic solvent and the alkaline deacid reagent, adding the palladium (II) compound, the organophosphorus compound and the copper (I) compound to the mixture while stirring to form a reaction system, stirring the reaction system, refluxing the reaction system, filtering the reaction system, and concentrating the filtrate to give the intermediate of formula B.

17. The preparation method according to claim 6, wherein the condensing agent is selected from DCC, DMAP, NMM, HOBt, HATU, and mixtures thereof.

18. The preparation method according to claim 4, wherein step (2) comprises adding the intermediate of formula B to a dried organic solvent, then adding a condensing agent for reaction, followed by adding the compound of formula C for reaction to give the ferrocene derivative of formula (I).

* * * * *